(12) United States Patent
Wei

(10) Patent No.: US 12,207,647 B2
(45) Date of Patent: *Jan. 28, 2025

(54) SUPERCOOLING METHODS FOR PRESERVATION OF BIOLOGICAL SAMPLES

(71) Applicant: X-Therma, Inc., Richmond, CA (US)

(72) Inventor: Xiaoxi Wei, El Cerrito, CA (US)

(73) Assignee: X-Therma, Inc., Hercules, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 18/076,785

(22) Filed: Dec. 7, 2022

(65) Prior Publication Data
US 2023/0292741 A1 Sep. 21, 2023

Related U.S. Application Data

(63) Continuation of application No. 16/583,895, filed on Sep. 26, 2019, now Pat. No. 11,564,388, which is a continuation of application No. PCT/US2018/027095, filed on Apr. 11, 2018.

(60) Provisional application No. 62/484,704, filed on Apr. 12, 2017.

(51) Int. Cl.
*A01N 1/02* (2006.01)

(52) U.S. Cl.
CPC ......... *A01N 1/0221* (2013.01); *A01N 1/0284* (2013.01)

(58) Field of Classification Search
None
See application file for complete search history.

(56) References Cited

U.S. PATENT DOCUMENTS

| | | | |
|---|---|---|---|
| 5,358,931 A | 10/1994 | Rubinsky et al. | |
| 11,564,388 B2 | 1/2023 | Wei | |
| 2012/0046443 A1 | 2/2012 | Zuckermann et al. | |
| 2013/0196369 A1 | 8/2013 | Hikita et al. | |
| 2016/0309706 A1 | 10/2016 | Matsumura et al. | |

FOREIGN PATENT DOCUMENTS

| | | |
|---|---|---|
| JP | 05503706 A | 6/1993 |
| JP | 2017043551 A | 3/2017 |
| WO | 2017017445 A1 | 2/2017 |
| WO | 2017066454 A2 | 4/2017 |
| WO | 2018191371 A1 | 10/2018 |
| WO | 2018191411 A1 | 10/2018 |
| WO | 2018232110 A1 | 12/2018 |

OTHER PUBLICATIONS

Claim set from copending U.S. Appl. No. 18/161,773, filed 2023.*
Merriam-Webster—Comprise definition, Available Online at URL: https://www.merriam-webster.com/dictionary/comprise (Year: 2022) 7 pages.
Brittanica Online Encyclopedia—Cryopreservation, retrieved from the internet Mar. 8, 2022: Available Online at URL: https://www.britannica.com/print/article/1452607 (Year:, 2022) 3 pages.
Ahn et al., "Synthesis of Cyclic Antifreeze Glycopeptide and Glycopeptoids and Their Ice Recrystallization Inhibition Activity," Bulletin of the Korean Chemical Society, vol. 33, No. 11, 2012, pp. 3565-3570.
Berendsen et al., "Supercooling Enables Long-Term Transplantation Survival Following 4 Days of Liver Preservation," Nature Medicine, vol. 20, No. 7, Jun. 2014, pp. 790-794.
Bruinsma et al., "Subzero Organ Preservation: the Dawn of a New Ice Age?," Current Opinion in Organ Transplantation, vol. 22, No. 3, Jun. 2017, pp. 281-286.
Bruinsma et al., "Supercooling Preservation of the Rat Liver for Transplantation," Nature Protocols, vol. 10, No. 3, Feb. 18, 2015, pp. 484-494.
De Vries et al., "Supercooling Extends Preservation Time of Human Livers," Nature Biotechnology, vol. 37, Sep. 9, 2019, pp. 1131-1136.
Deller et al., "Synthetic Polymers Enable Non-Vitreous Cellular Cryopreservation by Reducing Ice Crystal Growth During Thawing," Nature Communications, vol. 5, Article No. 3244, Feb. 3, 2014, 7 pages.
Application No. EP18783980.8, Extended European Search Report, Mailed On Jan. 18, 2021, 12 pages.
Huang et al., "Biomimetic Peptoid Oligomers as Dual-Action Antifreeze Agents," Proceedings of the National Academy of Sciences, vol. 109, No. 49, Dec. 4, 2012, pp. 19922-19927.
Huang et al., "Long-Term Deep-Supercooling of Large-Volume Water and Red Cell Suspensions via Surface Sealing with Immiscible Liquids," Nature Communications, vol. 9, No. 1, Aug. 10, 2018, pp. 1-10.
Norgren et al., "On-Resin Click-Glycoconjugation of Peptoids," Synthesis, No. 3, Jan. 9, 2009, pp. 488-494.
Okamoto et al., "Successful Sub-zero Non-freezing Preservation of Rat Lungs at −2° C. Utilizing a New Supercooling Technology," The Journal of Heart and Lung Transplantation, vol. 27, No. 10, Oct. 2008, pp. 1150-1157.

(Continued)

*Primary Examiner* — Evelyn Y Pyla
(74) *Attorney, Agent, or Firm* — Kilpatrick Townsend & Stockton LLP

(57) ABSTRACT

The present invention provides methods for cryopreserving a population of cells with improved cell viability. In some aspects, the method comprises contacting a population of cells with a peptoid polymer comprising one or more polar peptoid monomers, e.g., formulated in a cryoprotectant solution, and cooling the population of cells at a temperature of from 0° C. to about −20° C. for a time period of at least about 3 hours to produce a population of supercooled cells. The supercooling methods of the present invention provide excellent post-thaw cell survival and recovery. In certain embodiments, the population of cells is present in a tissue or an organ that is cryopreserved by performing the supercooling methods of the present invention.

21 Claims, 19 Drawing Sheets

(56) References Cited

OTHER PUBLICATIONS

Application No. PCT/US2018/027095, International Preliminary Report on Patentability, Mailed On Oct. 24, 2019, 9 pages.
Application No. PCT/US2018/027095, International Search Report and Written Opinion, Mailed On Sep. 12, 2018, 14 pages.
Prickett et al., "Effect of Supercooling and Cell Volume on Intracellular Ice Formation," Cryobiology, vol. 70, 2015, pp. 156-163.
Tessier et al., "Effect of Ice Nucleation and Cryoprotectants During High Subzero-Preservation in Endothelialized Microchannels," ACS Biomaterials Science & Engineering, vol. 4, No. 8, Jun. 26, 2018, pp. 1-25.
Usta et al., "Supercooling as a Viable Non-Freezing Cell Preservation Method of Rat Hepatocytes," PLoS ONE, vol. 8, No. 7, e69334, Jul. 2013, pp. 1-15.
Weiwen et al., "Ice Recrystallization Inhibition Activity of Protein Mimetic Peptoids," Journal of Inorganic and Organometallic Polymers and Materials, vol. 31, No. 1, Jul. 31, 2020, pp. 203-208.

* cited by examiner

Water　　　Cmpd. 1　　　EG　　　Cmpd. 10

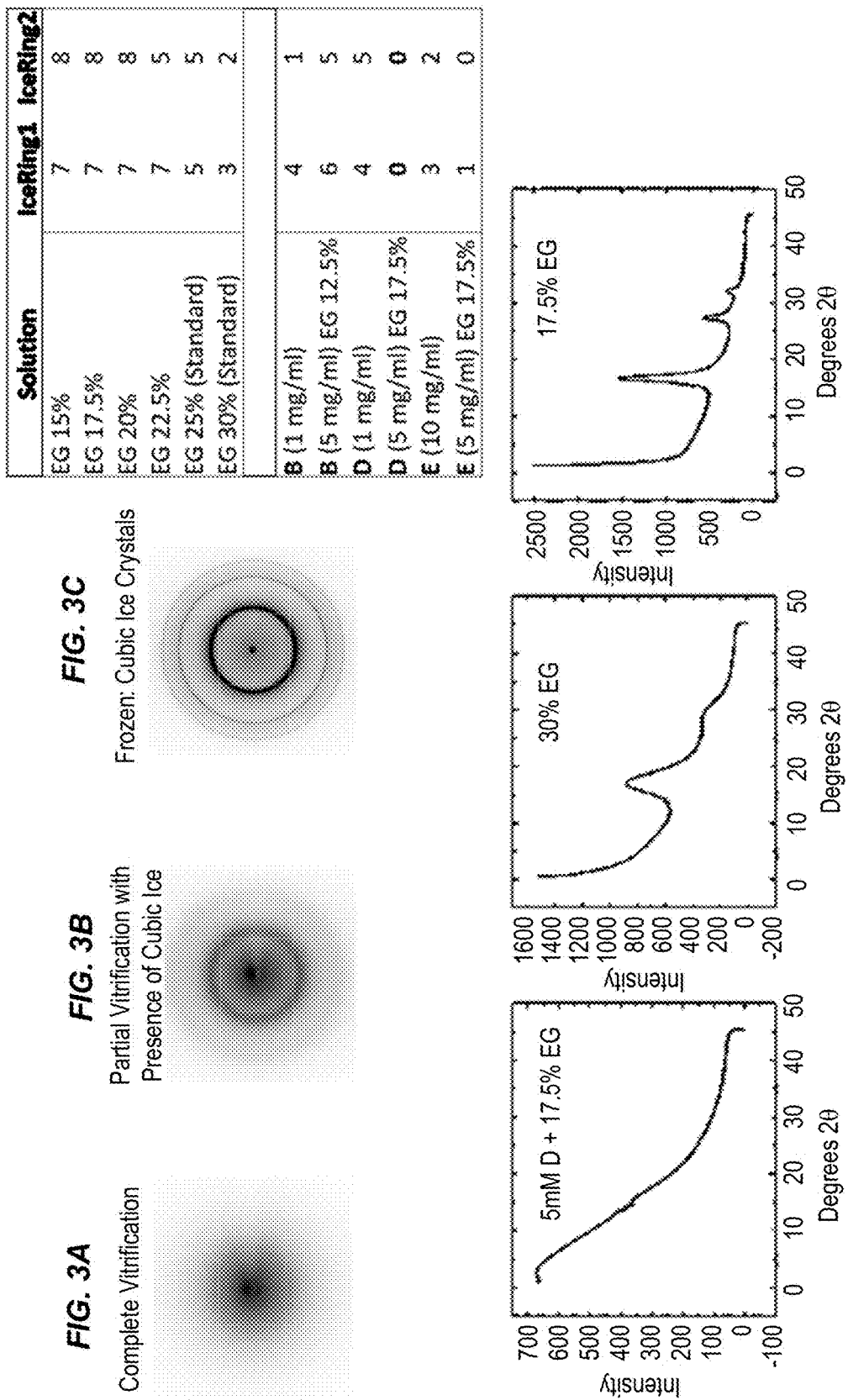

FIG. 4A
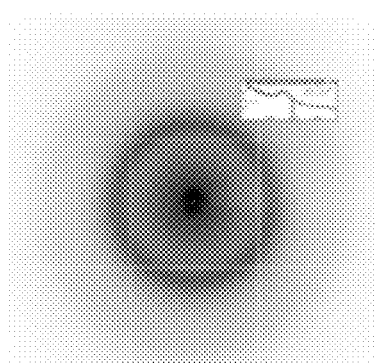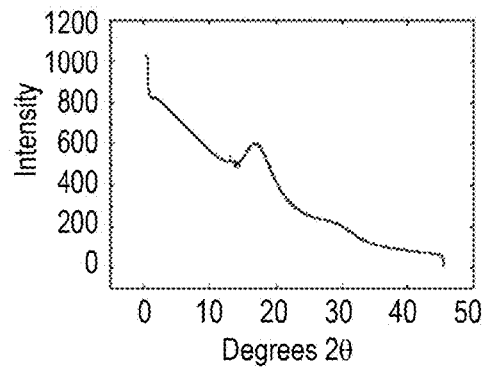
Compound 10
5 mg/mL
FIG. 4B
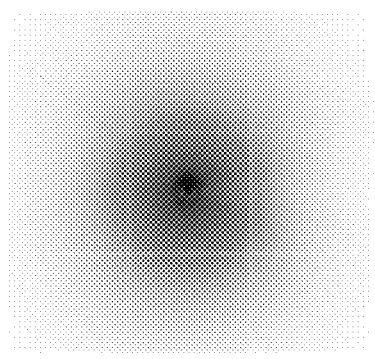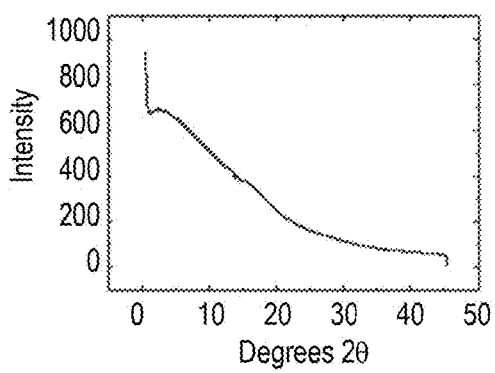
Compound 12
5 mg/mL
FIG. 4C
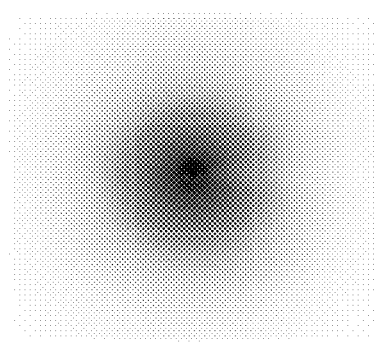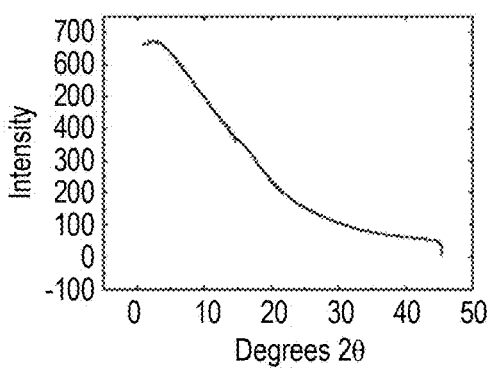
Compound 8
5 mg/mL
FIG. 4D
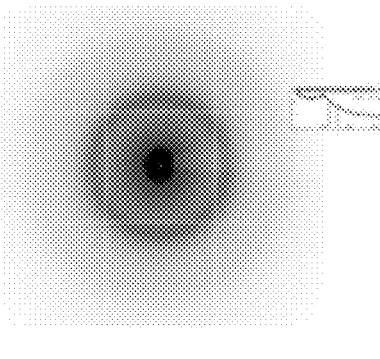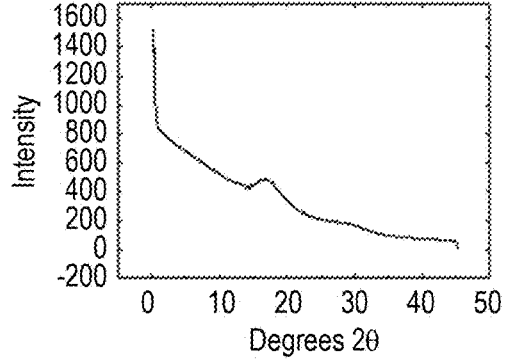
Compound 13
5 mg/mL Compound 11
5 mg/mL Compound 58
5 mg/mL Control
15% EG

*FIG. 5A*
*Compound 10*
*1 mg/mL*
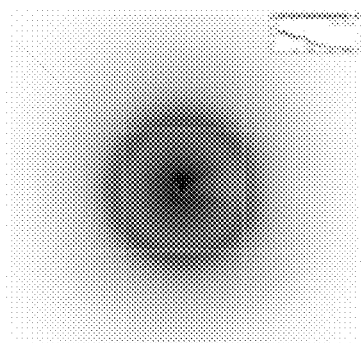 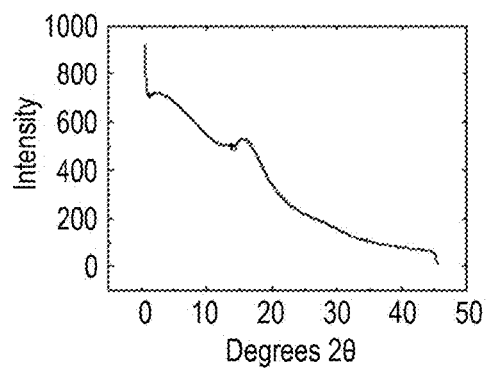
*FIG. 5B*
*Compound 12*
*1 mg/mL*
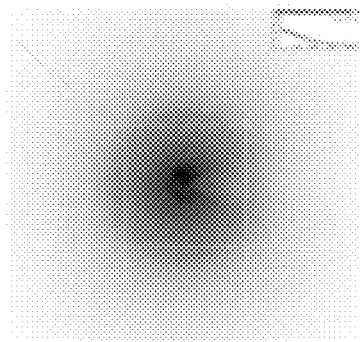 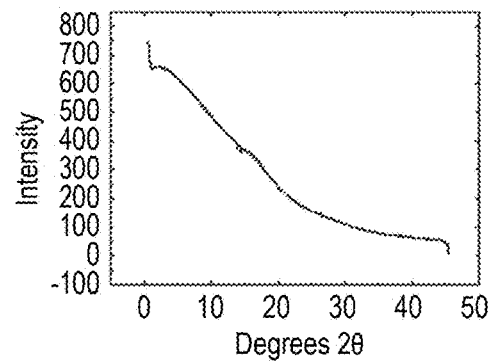
*FIG. 5C*
*Compound 8*
*1 mg/mL*
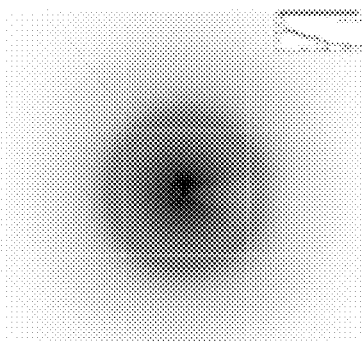 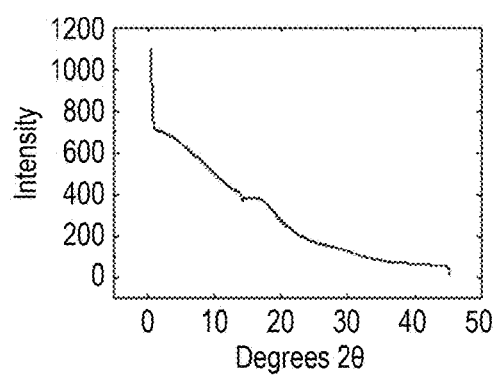
*FIG. 5D*
*Compound 13*
*1 mg/mL*
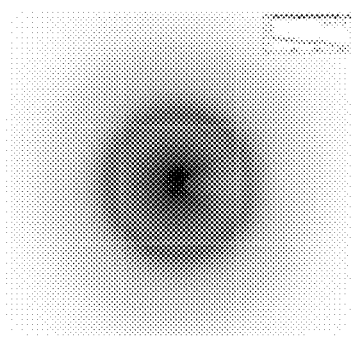 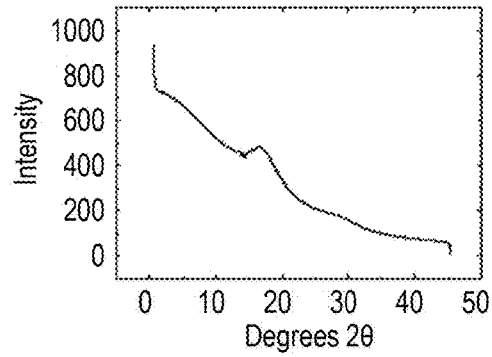

Compound 11
1 mg/mL

Compound 58
1 mg/mL

Control
17.5% EG

Control  Compound 12

Control  Compound 12

Control  Compound 12

SUPERCOOLING METHODS FOR PRESERVATION OF BIOLOGICAL SAMPLES

CROSS-REFERENCE TO RELATED APPLICATIONS

This application is a continuation of U.S. patent application Ser. No. 16/583,895 filed Sep. 26, 2019, which is a continuation of International Application No. PCT/US2018/027095 filed on Apr. 11, 2018, which claims priority to U.S. Provisional Application No. 62/484,704 filed on Apr. 12, 2017, the disclosures of which are hereby incorporated by reference in their entirety for all purposes.

STATEMENT REGARDING FEDERALLY SPONSORED RESEARCH OR DEVELOPMENT

This invention was made with Government support under Contract Nos. W81XWH17C0212 and W81XWH16C0058 awarded by the Department of Defense, Defense Health Agency. The Government has certain rights in the invention.

BACKGROUND OF THE INVENTION

A key bottleneck to be addressed in regenerative medicine is poor cryopreservation. As cell and tissue therapies transition to pivotal trials and commercial manufacturing, the logistics of shipping fresh starting biological materials and final drug products has proven to be a critical hurdle. Central to the success of these therapies are systems that provide high and reproducible levels of survival and recovery after prolonged storage at sub-zero temperature. Hypothermic preservation (or cryopreservation) of cell and tissue therapies is necessary for early phase clinical trials, long-term storage prior to administration, and for late-phase therapies manufactured centrally and distributed over a large patient network. Such therapies administered as a cell suspension or grafted tissue demand the use of a cryopreservation solution as vehicle that is compatible with the cells, non-toxic to the recipient, and suitable for storage of the therapy for a sufficient time prior to administration with high viability and function.

Cryopreservation technology is aged, toxic and ineffective with typical cell survival post-thaw below 50% and unreliable potency, which greatly hinders standardized shipping, batch manufacturing, scheduling, and final product release testing. The widespread use of cryoprotective agents (CPAs), such as DMSO, improve post-thaw viability of cryopreserved biological specimens by blocking ice growth, but prevents the realization of on-demand biobanking and advanced regenerative medicine offerings because DMSO is toxic to the cell product and subsequently to the treated patient. See, Sauer-Heilborn et al., *Transfusion*, 44 (6):907-16 (20040; Hubel, *Transfusion*, 41 (5):579-580 (2001). Removing DMSO post-thaw has been inefficient and recovery remains at less than 60%. See, Calmels et al., *Bone Marrow Transplant*, 31 (9):823-828 (2000). As a strong solvent, DMSO dissolves and leaches transfusion tubing and containers, which increases risk for cGMP processes. Animal and human derived serum (e.g., fetal bovine serum, FBS) as a natural product with undefined structure and composition, introduces batch-to-batch variation, additional biohazards, and is greatly influenced by supply chain issues, and geographic restrictions. Other freezing media may contain protein that is unstable leading to reduced shelf-life, or polymers that are not chemically-defined as a single product. The FDA seeks to restrain the use of DMSO and serum via suitable alternatives, which are needed to enable a robust infrastructure for highly effective and off-the-shelf cell and tissue products.

As such, there is a need in the art for non-toxic and hyperactive ice prevention materials and methods for preserving cell- and tissue-based samples with high viability and function. The present disclosure satisfies this need and provides other advantages as well.

SUMMARY OF THE INVENTION

In some aspects, provided herein is a method for cryopreserving a population of cells with improved cell viability, the method comprising:
  (a) contacting a population of cells with a peptoid polymer or a salt thereof comprising one or more polar peptoid monomers; and
  (b) cooling the population of cells to a temperature of from $0°$ C. to about $-20°$ C. for a time period of at least about 3 hours to produce a population of supercooled cells,
  wherein at least about 50% of the population of supercooled cells survive after warming to above $0°$ C.

In some embodiments, the percent of the population of supercooled cells that survive after warming is calculated by comparing the number of cells that survive the cryopreservation method to the starting number of cells. In some embodiments, the percent of the population of supercooled cells that survive after warming is calculated by normalizing the number of cells that survive the cryopreservation method to a pre-determined cell count of non-frozen cells (e.g., the starting cell number). In certain embodiments, the percent of the population of supercooled cells is calculated by determining the number of cells that survive the cryopreservation method at about 1 day or less (e.g., about 4, 8, 12, 16, or 20 hours) after warming.

In some embodiments, the population of cells is cooled to a temperature of from about $-5°$ C. to about $-20°$ C., about $-6°$ C. to about $-20°$ C., about $-7°$ C. to about $-20°$ C., about $-10°$ C. to about $-20°$ C., or about $-15°$ C. to about $-20°$ C. In other embodiments, the population of cells is cooled to a temperature of from $0°$ C. to about $-15°$ C., $0°$ C. to about $-10°$ C., or $0°$ C. to about $-5°$ C. In further embodiments, the population of cells is cooled to a temperature of from about $-5°$ C. to about $-15°$ C., about $-5°$ C. to about $-10°$ C., about $-6°$ C. to about $-15°$ C., about $-7°$ C. to about $-15°$ C., or about $-10°$ C. to about $-15°$ C. In certain embodiments, the population of cells is cooled to a temperature of about $0°$ C., $-1°$ C., $-2°$ C., $-3°$ C., $-4°$ C., $-5°$ C., $-6°$ C., $-7°$ C., $-8°$ C., $-9°$ C., $-10°$ C., $-11°$ C., $-12°$ C., $-13°$ C., $-14°$ C., $-15°$ C., $-16°$ C., $-17°$ C., $-18°$ C., $-19°$ C., or $-20°$ C. In some embodiments, the cooled population of cells is unfrozen (e.g., in a liquid, ice-free suspension) at the temperature.

In some embodiments, the population of cells is cooled for a time period of at least about 4, 8, 12, 16, 20, 24, 28, 32, 36, 40, 44, 48, 52, 56, 60, 64, 68, 72, 76, 80, 84, 88, 92, 96, 100, 104, 108, 112, 116, or 120 hours. In other embodiments, the population of cells is cooled for a time period of from about 1 to about 10 days, about 2 to about 10 days, about 3 to about 10 days, about 4 to about 10 days, about 5 to about 10 days, about 1 to about 8 days, about 2 to about 8 days, about 3 to about 8 days, about 4 to about 8 days, about 5 to about 8 days, about 1 to about 5 days, about 2 to about 5 days, about 3 to about 5 days, about 4 to about 5 days, about 2 to about 4 days, about 2 to about 3 days, or about 3 to about 4 days. In further embodiments, the population of cells is cooled for a time period of at least about 5 days (e.g., at least about 6, 7, 8, 9, or 10 days). In certain embodiments, the population of cells is cooled for a time period of about 1, 2, 3, 4, 5, 6, 7, 8, 9, 10, 11, 12, 13, 14, 15, 16, 17, 18, 19, 20, 21, 22, 23, or 24 days.

In some embodiments, at least about 50% of the population of supercooled cells survive after warming to a temperature above about 5° C., 10° C., 15° C., 20° C., 25° C., 30° C., or 35° C. In other embodiments, at least about 50% of the population of supercooled cells survive after warming to a temperature of from about 1° C. to about 37° C., about 5° C. to about 37° C., about 10° C. to about 37° C., about 15° C. to about 37° C., about 20° C. to about 37° C., about 25° C. to about 37° C., about 30° C. to about 37° C., about 35° C. to about 37° C., about 1° C. to about 35° C., about 10° C. to about 35° C., about 20° C. to about 35° C., about 30° C. to about 35° C., about 1° C. to about 30° C., about 10° C. to about 30° C., about 20° C. to about 30° C., about 1° C. to about 25° C., about 10° C. to about 25° C., about 20° C. to about 25° C., about 1° C. to about 20° C., about 10° C. to about 20° C., about 1° C. to about 15° C., about 10° C. to about 15° C., about 1° C. to about 10° C., about 5° C. to about 10° C., or about 1° C. to about 5° C. In certain embodiments, at least about 50% of the population of supercooled cells survive after warming to a temperature of about 1° C., 2° C., 3° C., 4° C., 5° C., 6° C., 7° C., 8° C., 9° C., 10° C., 11° C., 12° C., 13° C., 14° C., 15° C. 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., or 37° C.

In some embodiments, at least about 55% of the population of supercooled cells survive after warming. In some embodiments, at least about 60% of the population of supercooled cells survive after warming. In some embodiments, at least about 65% of the population of supercooled cells survive after warming. In some embodiments, at least about 70% of the population of supercooled cells survive after warming. In some embodiments, at least about 75% of the population of supercooled cells survive after warming. In some embodiments, at least about 80% of the population of supercooled cells survive after warming. In some embodiments, at least about 85% of the population of supercooled cells survive after warming. In some embodiments, at least about 90% of the population of supercooled cells survive after warming. In some embodiments, at least about 95% of the population of supercooled cells survive after warming.

In some embodiments, at least about 50% (e.g., at least about 55%, 60%, 65%, 70%, 75%, 80%, 85%, 90%, or 95%) of the population of supercooled cells survive for at least about 1 day after warming. In other embodiments, at least about 50% (e.g., at least about 55%, 60%, 65%, 70%, 75%, 80%, 85%, 90%, or 95%) of the population of supercooled cells survive for a time period of from about 1 to about 10 days, about 2 to about 10 days, about 3 to about 10 days, about 4 to about 10 days, about 5 to about 10 days, about 1 to about 8 days, about 2 to about 8 days, about 3 to about 8 days, about 4 to about 8 days, about 5 to about 8 days, about 1 to about 5 days, about 2 to about 5 days, about 3 to about 5 days, about 4 to about 5 days, about 2 to about 4 days, about 2 to about 3 days, or about 3 to about 4 days after warming. In further embodiments, at least about 50% (e.g., at least about 55%, 60%, 65%, 70%, 75%, 80%, 85%, 90%, or 95%) of the population of supercooled cells survive for at least about 2 days (e.g., at least about 3, 4, 5, 6, or 7 days) after warming. In certain embodiments, at least about 50% (e.g., at least about 55%, 60%, 65%, 70%, 75%, 80%, 85%, 90%, or 95%) of the population of supercooled cells survive for about 1, 2, 3, 4, 5, 6, 7, 8, 9, 10, 11, 12, 13, 14, 15, 16, 17, 18, 19, 20, 21, 22, 23, or 24 days after warming.

In some embodiments, the improved cell viability comprises enhanced proliferation of the population of supercooled cells that survive after warming compared to a control population of supercooled cells. In some embodiments, the control population of supercooled cells has not been contacted with the peptoid polymer (e.g., the control population was contacted with cryoprotectant solution only, a solution containing DMSO, or cell culture media only). In certain embodiments, the number of cells in the population of supercooled cells at a specific time point after warming (e.g., about 1, 2, 3, 4, 5, 6, 7, or more days after warming) is at least about 1-fold greater (e.g., at least about 1.5-fold, 2-fold, 2.5-fold, 3-fold, 4-fold, 5-fold, 6-fold, 7-fold, 8-fold, 9-fold, or 10-fold greater) than the number of cells in the control population of supercooled cells at that time point. As a non-limiting example, the number of cells in the population of supercooled cells at about 3 days after warming can be at least about 1-fold greater than the number of cells in the control population of supercooled cells. As another non-limiting example, the number of cells in the population of supercooled cells at about 6 days after warming can be at least about 2-fold greater than the number of cells in the control population of supercooled cells.

In related aspects, provided herein is a method for cryopreserving a population of cells with improved cell viability, the method comprising:

(a) contacting a population of cells with a peptoid polymer or a salt thereof comprising one or more polar peptoid monomers; and (b) cooling the population of cells to a temperature of from 0° C. to about −20° C. for a time period of at least about 3 hours to produce a population of supercooled cells, wherein the improved cell viability comprises enhanced proliferation of the population of supercooled cells that survive after warming compared to a control population of supercooled cells.

In some embodiments, the control population of supercooled cells has not been contacted with the peptoid polymer (e.g., the control population was contacted with cryoprotectant solution only, a solution containing DMSO, or cell culture media only). In certain embodiments, the number of cells in the population of supercooled cells at a specific time point after warming (e.g., about 1, 2, 3, 4, 5, 6, 7, or more days after warming) is at least about 1-fold greater (e.g., at least about 1.5-fold, 2-fold, 2.5-fold, 3-fold, 4-fold, 5-fold, 6-fold, 7-fold, 8-fold, 9-fold, or 10-fold greater) than the number of cells in the control population of supercooled cells at that time point. Further embodiments related to these aspects of the present invention are described above.

In some embodiments, the peptoid polymer is present in an amount sufficient to reduce or inhibit ice crystal formation at the temperature to which the population of cells is cooled. In certain instances, the peptoid polymer is present in amount between about 100 nM and about 1000 mM, e.g., between about 100 nM and about 100 mM.

In some embodiments, the population of cells comprises a tissue or an organ. In some embodiments, the population of cells comprises primary cells. In certain embodiments, the population of cells is selected from the group consisting of heart cells, liver cells, lung cells, kidney cells, pancreatic cells, gastric cells, intestinal cells, muscle cells, skin cells, neural cells, blood cells, immune cells, fibroblasts, genitourinary cells, bone cells, stem cells, sperm cells, oocytes, embryonic cells, epithelial cells, endothelial cells, and a combination thereof. Non-limiting examples of genitourinary cells include corpus cavernosum cells such as, e.g., smooth muscle corpus cavernosum cells, epithelial corpus cavernosum cells, and combinations thereof.

In some embodiments, the method further comprises:
(c) warming the population of supercooled cells to above 0° C.

In some embodiments, the peptoid polymer comprises at least 2, 3, 4, 5, 6, 7, 8, 9, 10, 15, 20, 25, or more polar peptoid monomers. In some embodiments, the polar peptoid monomers have independently selected side chains comprising a hydroxyl group. In some embodiments, the independently selected side chains are optionally substituted $C_{1-18}$ hydroxyalkyl groups. In some embodiments, the $C_{1-18}$ hydroxyalkyl groups are independently selected optionally substituted $C_{1-6}$ hydroxyalkyl groups. In certain instances, one or more or all of the side chains of the polar peptoid monomers have the following structure:

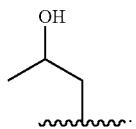 [SMILES: *CC(C)O]

Non-limiting examples of polar peptoid monomers include:

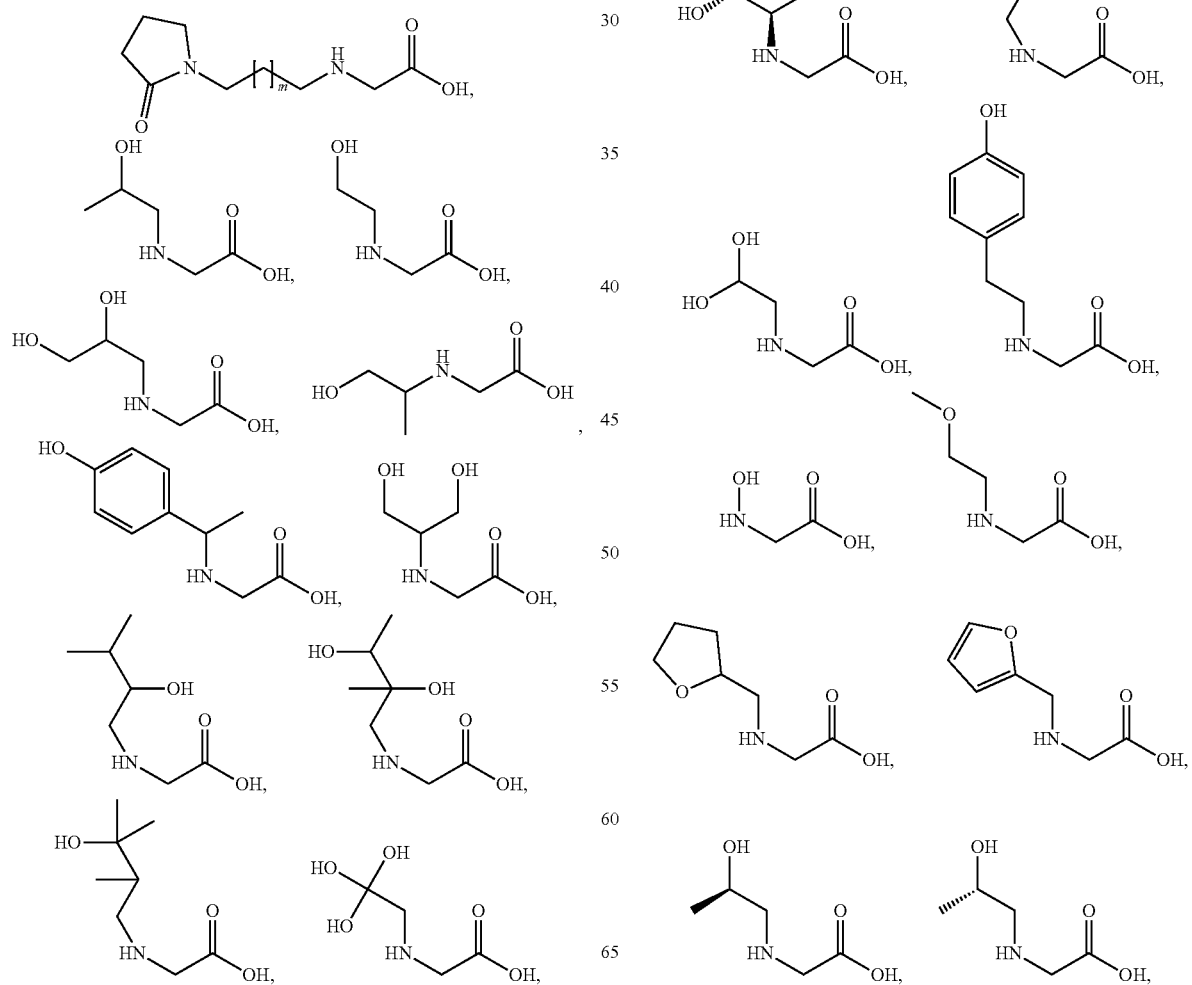

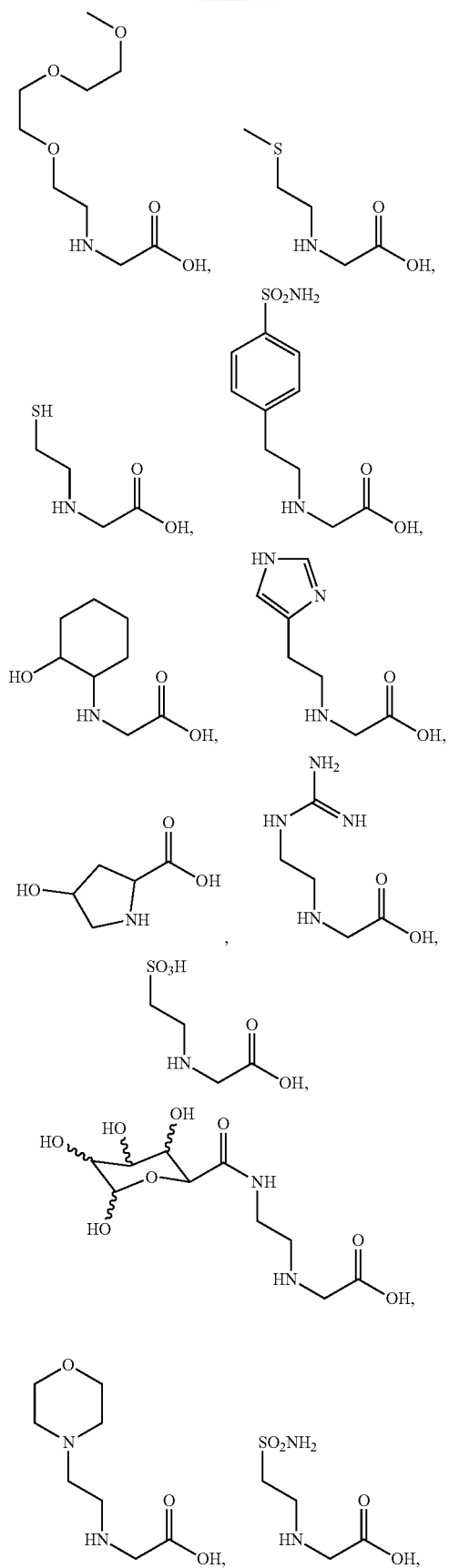
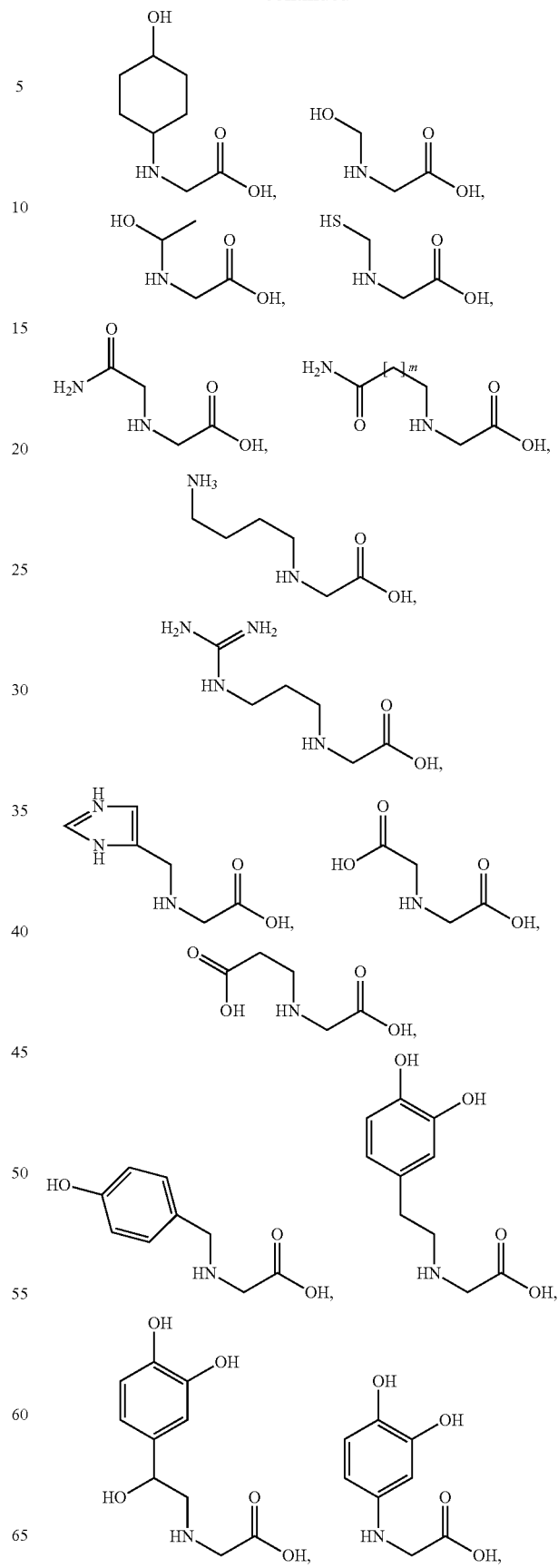

-continued

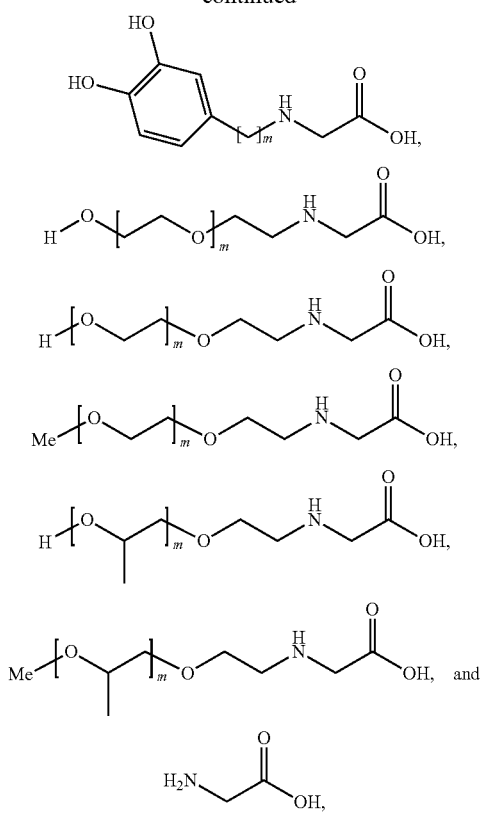

wherein the subscript m is the number of repeat units and is between 1 and 10 (e.g., m is 1, 2, 3, 4, 5, 6, 7, 8, 9, or 10). In some embodiments, the repeating unit, m, can be between 1 and 2, 1 and 3, 1 and 4, 1 and 5, 1 and 6, 1 and 7, 1 and 8, 1 and 9, or 1 and 10.

In some embodiments, the peptoid polymer further comprises at least 1, 2, 3, 4, 5, 6, 7, 8, 9, 10, 15, 20, 25, or more hydrophobic peptoid monomers. Non-limiting examples of hydrophobic peptoid monomers include:

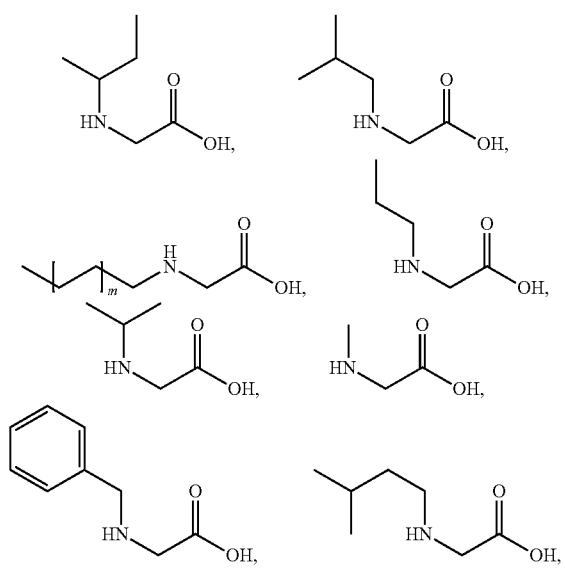

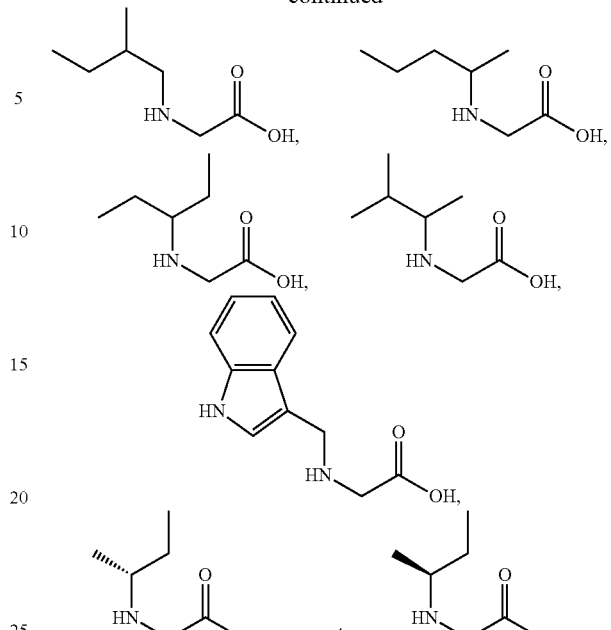

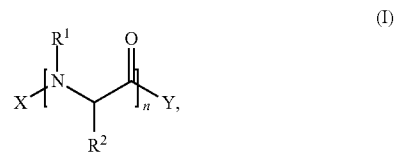

wherein the subscript m is the number of repeat units and is between 1 and 10 (e.g., m is 1, 2, 3, 4, 5, 6, 7, 8, 9, or 10). In some embodiments, the repeating unit, m, can be between 1 and 2, 1 and 3, 1 and 4, 1 and 5, 1 and 6, 1 and 7, 1 and 8, 1 and 9, or 1 and 10.

In some embodiments, the peptoid polymer is a peptoid-peptide hybrid or a salt thereof comprising the peptoid polymer and one or more amino acids, wherein the one or more amino acids are located at one or both ends of the peptoid polymer and/or between one or more peptoid monomers.

In some embodiments, the peptoid polymer has a structure of formula (I):

$$X\underset{R^2}{\overset{R^1}{{\left[\underset{}{\overset{}{N}}\right]}_n}}Y,$$

(I)

a tautomer thereof or stereoisomer thereof,
wherein:
each $R^1$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl;
wherein at least one instance of $R^1$ is $C_{1-18}$ hydroxyalkyl, and
wherein any of the cycloalkyl, heterocycloalkyl, aryl, and heteroaryl groups is optionally and independently substituted with one or more $R^3$ groups;

each R² is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted $C_{1-18}$ alkylamino, optionally substituted $C_{1-18}$ alkylthio, and optionally substituted carboxyalkyl;

each R³ is independently selected from the group consisting of halogen, oxo, thioxo, —OH, —SH, amino, $C_{1-8}$ alkyl, $C_{1-8}$ hydroxyalkyl, $C_{1-8}$ alkylamino, and $C_{1-8}$ alkylthio;

X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH₂, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond; and the subscript n, representing the number of monomers in the polymer, is between 2 and 50.

In some embodiments, at least 2, 3, 4, 5, 6, 7, 8, 9, 10, 15, 20, 25, or more instances of R¹ are independently selected optionally substituted $C_{1-18}$ hydroxyalkyl groups. In some embodiments, the $C_{1-18}$ hydroxyalkyl groups are independently selected optionally substituted $C_{1-6}$ hydroxyalkyl groups.

In some embodiments, one or more R¹ has a structure according to $R^{1b}$:

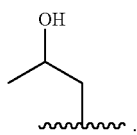

In some embodiments, each instance of R¹ in the peptoid polymer is selected from the group consisting of:

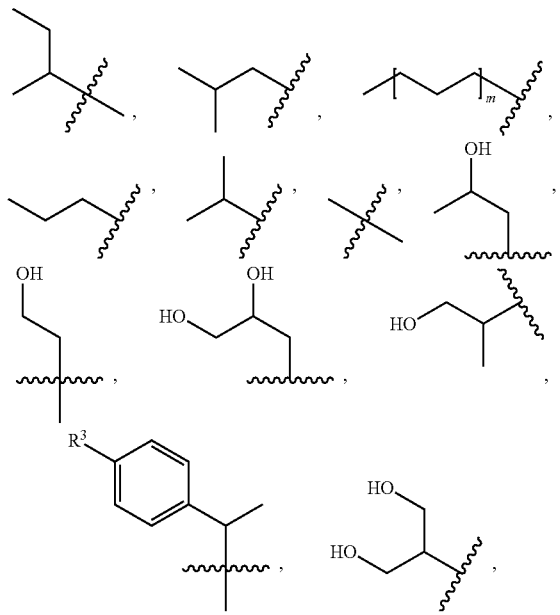

-continued

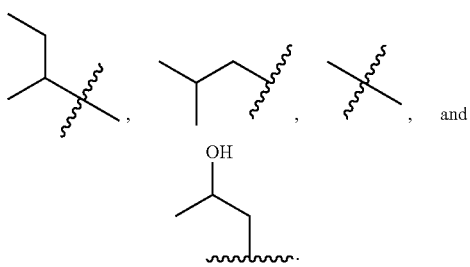

wherein:
m is between 1 and 8; and
R³ is selected from the group consisting of H, $C_{1-8}$ alkyl, hydroxyl, thiol, nitro, amine, oxo, and thioxo.

In some embodiments, each instance of R¹ in the peptoid polymer is selected from the group consisting of:

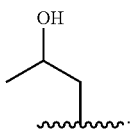

In some embodiments, each instance of R¹ in the peptoid polymer is a $C_{1-18}$ hydroxyalkyl group. In some embodiments, each instance of R¹ is a $C_{1-6}$ hydroxyalkyl group. In some embodiments, each instance of R¹ is the same $C_{1-6}$ hydroxyalkyl group. In some embodiments, each instance of R¹ is:

In some embodiments, each instance of R² is H.

In some embodiments, the sequence length of the peptoid polymer, n, is between 3 and 25. In some embodiments, the sequence length of the peptoid polymer, n, is between 5 and 25. In some embodiments, the sequence length of the peptoid polymer, n, is between 6 and 50. In some embodiments, the sequence length of the peptoid polymer, n, is between 6 and 25. In some embodiments, the sequence length of the peptoid polymer, n, is between 6 and 20. In some embodiments, the sequence length of the peptoid polymer, n, is between 8 and 50. In some embodiments, the sequence length of the peptoid polymer, n, is between 8 and 25. In some embodiments, the sequence length of the peptoid polymer, n, is between 8 and 20. In some embodiments, the sequence length of the peptoid polymer, n, is between 10 and 25.

In some embodiments, X and Y are H, optionally substituted $C_{1-8}$ alkylamino, —OH, —SH, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen.

In some embodiments, X and Y of the peptoid polymer are taken together to form a covalent bond.

In some embodiments, the peptoid polymer is selected from the group of polymers set forth in Table 2, Table 3, Table 4, Table 5, Table 6, Table 7, Table 8, Table 9, or Table 10.

In some embodiments, the peptoid polymer comprises subunits comprising one or more first hydrophobic peptoid monomers H and one or more first polar peptoid monomers P arranged such that the peptoid polymer has the sequence $[H_aP_b]_n$ or $[P_bH_a]_n$, wherein:
- the subscript a, representing the number of consecutive first hydrophobic peptoid monomers within a subunit, is between 1 and 10;
- the subscript b, representing the number of consecutive first polar peptoid monomers within a subunit, is between 1 and 10; and
- the subscript n, representing the number of subunits within the peptoid polymer, is between 2 and 50.

In some embodiments, the peptoid polymer further comprises substituents X and Y such that the peptoid polymer has the sequence $X\text{---}[H_aP_b]_n\text{---}Y$ or $X\text{---}[P_bH_a]_n\text{---}Y$, wherein:
- X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or
- alternatively X and Y are taken together to form a covalent bond.

In some embodiments, the subunits further comprise a second hydrophobic peptoid monomer and/or a second polar peptoid monomer such that the peptoid polymer has the sequence $[H_aP_bH_cP_d]_n$ or $[P_bH_aP_dH_c]_n$, wherein:
- the subscript c, representing the number of consecutive second hydrophobic peptoid monomers within a subunit, is between 0 and 10;
- the subscript d, representing the number of consecutive second polar peptoid monomers within a subunit, is between 0 and 10; and
- both c and d are not 0.

In some embodiments, the peptoid polymer further comprises substituents X and Y such that the peptoid polymer has the sequence $X\text{---}[H_aP_bH_cP_d]_n\text{---}Y$ or $X\text{---}[P_bH_aP_dH_c]_n\text{---}Y$, wherein:
- X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or
- alternatively X and Y are taken together to form a covalent bond.

In some embodiments, the peptoid polymer further comprises a sequence Z that comprises one or more hydrophobic peptoid monomers and/or one or more polar peptoid monomers, wherein Z is located before the first subunit, after the last subunit, and/or between one or more subunits. In some instances, Z comprises one or more hydrophobic peptoid monomers. In other instances, Z comprises one or more polar peptoid monomers. In yet other instances, Z comprises one or more hydrophobic peptoid monomers and one or more polar peptoid monomers.

In some embodiments, the peptoid polymer comprises: (a) subunits comprising two first hydrophobic peptoid monomers H and two first polar peptoid monomers P, and (b) two second hydrophobic peptoid monomers located at the C-terminal end of the peptoid polymer, arranged such that the peptoid polymer has the sequence $[H_2P_2]_nH_2$ or $[P_2H_2]_nH_2$, wherein the subscript n, representing the number of subunits within the peptoid polymer, is between 1 and 50. In some embodiments, the peptoid polymer comprises Compound 81.

In some embodiments, the peptoid polymer further comprises substituents X and Y such that the peptoid polymer has the sequence $X\text{---}[H_2P_2]_nH_2\text{---}Y$ or $X\text{---}[P_2H_2]_nH_2\text{---}Y$, wherein X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond. In some embodiments, n is between 1 and 10.

In some embodiments, the first and/or second hydrophobic peptoid monomers are independently selected from the hydrophobic peptoid monomers set forth above. In some embodiments, the peptoid polymer comprises a polar peptoid monomer having a side chain that comprises a hydroxyl group. In some embodiments, the first and/or second polar peptoid monomers are independently selected from the polar peptoid monomers set forth above.

In some embodiments, each of the first and/or second polar peptoid monomers comprise a side chain that is independently selected from the group consisting of ($C_{1-6}$ alkoxy)($C_{1-6}$ alkylene), (oligo[ethylene glycol]), (4- to 10-membered heterocycloalkyl)($C_{1-6}$ alkylene), and (5- to 10-membered heteroaryl)($C_{1-6}$ alkylene). In some embodiments, (4- to 10-membered heterocycloalkyl)($C_{1-6}$ alkylene) comprises a 4-6 membered heterocyclic ring, wherein at least one member is selected from the group consisting of O and N. In some embodiments, (4- to 10-membered heterocycloalkyl)($C_{1-6}$ alkylene) comprises a tetrahydrofuranyl or oxopyrrolidinyl moiety. In some instances, the peptoid polymer comprises

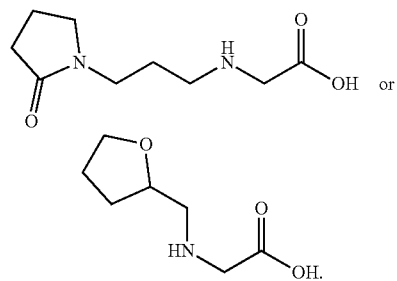

In particular instances, all of the polar peptoid monomers are

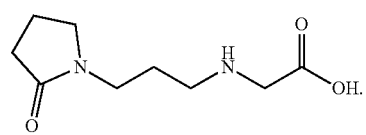 [SMILES: O=C(O)CNCCCN1CCCC1=O]

In some embodiments, the peptoid polymer comprises Compound 63, Compound 76, Compound 86, or Compound 87.

In some embodiments, (5- to 10-membered heteroaryl)($C_{1-6}$ alkylene) comprises a 5-6 membered aromatic ring, wherein at least one ring member is selected from the group consisting of O and N. In some embodiments, (5- to 10-membered heteroaryl)($C_{1-6}$ alkylene) comprises a furanyl moiety. In some instances, the peptoid polymer comprises

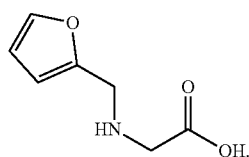 [SMILES: O=C(O)CNCc1ccco1]

In particular instances, the peptoid polymer comprises Compound 73.

In some embodiments, the side chain comprises a methoxyethyl group. In some instances, the peptoid polymer comprises

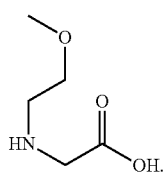

In particular instances, the peptoid polymer comprises Compound 62.

In some embodiments, the side chain comprises an oligo (ethylene glycol) moiety. In some embodiments, the oligo (ethylene glycol) moiety is a 2-(2-(2-methoxyethoxy)ethoxy)ethyl moiety. In some instances, the peptoid polymer comprises

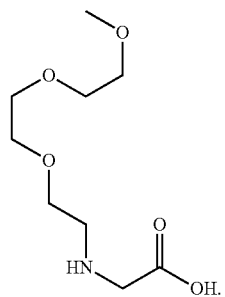

In particular instances, the peptoid polymer comprises Compound 67.

In some embodiments, n is between 2 and 10. In some embodiments, a is between 1 and 5. In some embodiments, b is between 1 and 5. In some embodiments, a is between 1 and 3 and b is between 1 and 3. In some embodiments, c is between 0 and 5. In some embodiments, d is between 0 and 5.

In some embodiments, about 10 percent of the peptoid monomers are hydrophobic. In some embodiments, about 20 percent of the peptoid monomers are hydrophobic. In some embodiments, about 30 percent of the peptoid monomers are hydrophobic. In some embodiments, about 40 percent of the peptoid monomers are hydrophobic. In some embodiments, about 50 percent of the peptoid monomers are hydrophobic. In some embodiments, about 60 percent of the peptoid monomers are hydrophobic. In some embodiments, about 70 percent of the peptoid monomers are hydrophobic. In some embodiments, about 80 percent of the peptoid monomers are hydrophobic. In some embodiments, about 90 percent of the peptoid monomers are hydrophobic.

In some embodiments, the peptoid polymer or peptoid-peptide hybrid is in the form of a salt. Non-limiting examples of salts include the hydrochloride, acetate, sulfate, phosphate, maleate, citrate, mesylate, nitrate, tartrate, and gluconate salts of the peptoid polymers and peptoid-peptide hybrids described herein.

In some embodiments, the peptoid polymer and/or peptoid-peptide hybrid is formulated in a cryoprotectant solution. In some embodiments, the cryoprotectant solution further comprises a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a nonionic surfactant, a protein, dimethyl sulfoxide (DMSO), polyethylene glycol (PEG), polypropylene glycol (PPG), Ficoll®, polyvinylpyrrolidone, polyvinyl alcohol, hyaluronan, formamide, a natural or synthetic hydrogel, and a combination thereof.

In some embodiments, the cryoprotectant solution further comprises an alcohol selected from the group consisting of propylene glycol, ethylene glycol, glycerol, methanol, butylene glycol, adonitol, ethanol, trimethylene glycol, diethylene glycol, polyethylene oxide, erythritol, sorbitol, xythyritol, polypropylene glycol, 2-methyl-2,4-pentanediol (MPD), mannitol, inositol, dithioritol, 1,2-propanediol, and a combination thereof.

In some embodiments, the cryoprotectant solution further comprises a sugar that is selected from the group consisting of a monosaccharide, a disaccharide, a polysaccharide, and a combination thereof. In some instances, the sugar is a monosaccharide selected from the group consisting of glucose, galactose, arabinose, fructose, xylose, mannose, 3-O-Methyl-D-glucopyranose, and a combination thereof. In other instances, the sugar is a disaccharide selected from the group consisting of sucrose, trehalose, lactose, maltose, and a combination thereof. In still other instances, the sugar is a polysaccharide selected from the group consisting of raffinose, dextran, and a combination thereof.

In some embodiments, the cryoprotectant solution further comprises a PEG or PPG that has an average molecular weight less than about 3,000 g/mol. In particular instances, the PEG or PPG has an average molecular weight between about 200 and 400 g/mol.

In some embodiments, the cryoprotectant solution further comprises a protein selected from the group consisting of bovine serum albumin, human serum albumin, gelatin, and a combination thereof. In some embodiments, the cryoprotectant solution further comprises a natural or synthetic hydrogel that comprises chitosan, hyaluronic acid, or a combination thereof. In some embodiments, the cryoprotectant solution further comprises a nonionic surfactant selected from the group consisting of polyoxyethylene lauryl ether, polysorbate 80, and a combination thereof.

In further aspects, provided herein is a population of supercooled cells with improved cell viability produced by any of the methods described herein.

Other objects, features, and advantages of the present invention will be apparent to one of skill in the art from the following detailed description and figures.

BRIEF DESCRIPTION OF THE DRAWINGS

FIG. 2A illustrates the assay in which Compounds 1 (1 eq.) and 10 (1 eq.) were dissolved in MilliQ water and subjected to subzero temperatures. Comparison was made to water alone and a solution of ethylene glycol (EG) (18 eq.). FIG. 2B displays normalized results of the assay depicted in FIG. 2A.

FIGS. 3A-3D show x-ray diffraction (XRD) crystallography data. FIG. 3A shows XRD data for a solution containing 5 mM Compound 12 and 17.5% (v/v) ethylene glycol (EG). FIG. 3B shows XRD data for a solution containing 30% (v/v) EG. FIG. 3C shows XRD data for a solution containing 17.5% (v/v) EG. FIG. 3D shows ice ring scores for a number of solutions containing EG, Compound 2 (labeled as "B"), Compound 12 (labeled as "D"), and/or Compound 8 (labeled as "E"). For each different solution, two separate ice ring scores were determined.

FIGS. 4A-4G show x-ray diffraction (XRD) crystallography data for solutions containing 5 mg/mL of Compound 10, Compound 12, Compound 8, Compound 13, Compound 11, and Compound 58, compared to an ethylene glycol (EG) control. Each solution also contained 300 mM NaCl, 100 mM HEPES, 15% (v/v) ethylene glycol, and pH was adjusted to 7.2. FIG. 4A: Compound 10 XRD crystallography pattern (left) and spectrum plot (right). FIG. 4B: Compound 12 XRD crystallography pattern (left) and spectrum plot (right). FIG. 4C: Compound 8 XRD crystallography pattern (left) and spectrum plot (right). FIG. 4D: Compound 13 XRD crystallography pattern (left) and spectrum plot (right). FIG. 4E: Compound 11 XRD crystallography pattern (left) and spectrum plot (right). FIG. 4F: Compound 58 XRD crystallography pattern (left) and spectrum plot (right). FIG. 4G: EG control XRD crystallography pattern (left) and spectrum plot (right). For XRD spectrum plots, intensity was plotted as a function of angle (2θ degrees).

FIGS. 5A-5G show x-ray diffraction (XRD) crystallography data for solutions containing 1 mg/mL of Compound 10, Compound 12, Compound 8, Compound 13, Compound 11, and Compound 58, compared to an ethylene glycol (EG) control. Each solution also contained 300 mM NaCl, 100 mM HEPES, 17.5% (v/v) ethylene glycol, and pH was adjusted to 7.2. FIG. 5A: Compound 10 XRD crystallography pattern (left) and spectrum plot (right). FIG. 5B: Compound 12 XRD crystallography pattern (left) and spectrum plot (right). FIG. 5C: Compound 8 XRD crystallography pattern (left) and spectrum plot (right). FIG. 5D: Compound 13 XRD crystallography pattern (left) and spectrum plot (right). FIG. 5E: Compound 11 XRD crystallography pattern (left) and spectrum plot (right). FIG. 5F: Compound 58 XRD crystallography pattern (left) and spectrum plot (right). FIG. 5G: EG control XRD crystallography pattern (left) and spectrum plot (right). For XRD spectrum plots, intensity was plotted as a function of angle (2θ degrees).

FIG. 6A shows that during rapid freezing in liquid nitrogen, the solution containing Compound 12 vit- rified while the control solution completely froze. FIG. 6B shows that during rewarming at 37° C., the solution containing Compound 12 unfroze (within two seconds) while the control stayed frozen. FIG. 6C shows that after overnight in a −20° C. freezer, the Compound 12 solution remained unfrozen, unlike the control.

DETAILED DESCRIPTION OF THE INVENTION

I. Introduction

Figure 1:
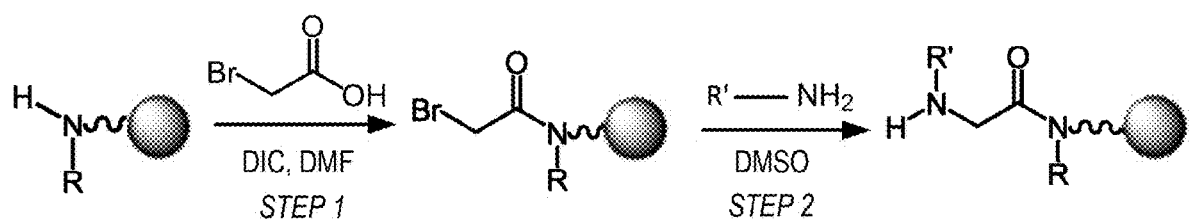
FIG. 1 illustrates a general protocol for the synthesis of peptoid oligomers using the "submonomer" approach.

The banking of cells and tissues at low temperatures using cryopreservation is critical for many biological products and applications, but remains a significant problem that has yet to allow the successful full recovery or viable therapeutic cells, tissues, and organs. Cryopreservation is typically performed with cryoprotective agents (CPAs), which are critical chemical additives such as dimethyl sulfoxide (DMSO), bovine serum albumin (BSA), and others. The CPAs are used to improve the post-thaw viability of cryopreserved biological systems by preventing ice crystal nucleation and growth. However, these agents exhibit various levels of cytotoxicity at their effective concentrations and thus limit the success of cryopreservation, biobanking, and advanced regenerative medicine. This lack of an effective and safe CPA contributes to the widespread use of toxic CPAs.

The present invention is based, in part, on the discovery that peptoid polymers comprising at least one polar peptoid monomer (e.g., having a polar side chain such as a hydroxyl group) can be used in ice-free supercooling methods that provide excellent cell survival and recovery when cell populations are cooled to supercooling temperatures (e.g., 0° C. to −20° C.) for a time period of at least about 3 hours, compared to control samples without peptoid polymers that suffer a complete loss of cell viability after 3-24 hrs. As a non-limiting example, studies with human model cell types (e.g., HEK-293, K562, Jurkat, SK-OV-3) using the ice-free supercooling methods described herein have demonstrated typical post-thaw (e.g., post-warming) cell recoveries in excess of 85%, at times achieving nearly 100% survival 16-hours post-thaw.

II. Abbreviations and Definitions

The abbreviations used herein are conventional, unless otherwise defined. The following abbreviations are used to refer to the monomer units of the peptoid polymer: Nsb (2-(sec-butylamino)acetic acid), Nib (2-(isobutylamino)acetic acid), Nbu (2-butylamino)acetic acid), Npr (2-propylamino)acetic acid), Nip (2-(isopropylamino)acetic acid), Nme (2-(methylamino)acetic acid), Nhp (2-((2-hydroxypropyl)amino)acetic acid), Nhe (2-((2-hydroxyethyl)amino) acetic acid), Ndp (2-((2,3-dihydroxypropryl)amino)acetic acid, Nyp (2-((1-hydroxypropan-2-yl)amino) acetic acid), Nep (2-((1-(4-hydroxyphenyl)ethyl)amino) acetic acid, Ndh (2-((1,3,-dihydrooxypropan-2-yl)amino)acetic acid, Nop (2-((3-(2-oxopyrrolindin-1-yl)propyl)amino)acetic acid, Nmo (2-(2-methoxyethylamino)acetic acid), Ntf (2-((tetrahydrofuran-2-yl)methylamino)acetic acid), Nff (2-(furan-2-ylmethylamino)acetic acid), Nmb (2-(2-methylbutylamino)acetic acid), Nrh (2-(R)-(2-hydroxypropylamino)acetic acid), Nsh (2-(S)-(2-hydroxypropylamino)acetic acid), N3p (2-(2-(2-methoxyethoxy)ethoxy)ethylamino)acetic acid), Nbr ((2-(R)-sec-butylamino)acetic acid), and Nbs ((2-(S)-sec-butylamino)acetic acid). The following abbreviations are used to refer to chemical compounds: DMF (N, N'-dimethylformamide), DIEA (diisopropylethylamine), DIC (N, N'-diisopropylcarbodiimide), ACN (acetonitrile), DCM (methylene chloride), HFIP (hexafluoroisopropyl alcohol); Fmoc (9-fluorenylmethoxycarbonyl).

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "about" as used herein to modify a numerical value indicates a defined range around that value. If "X" were the value, "about X" would indicate a value from 0.9X to 1.1X, and more preferably, a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 30 carbons atoms, such as, but not limited to heptyl, octyl, nonyl, decyl, etc. Alkyl groups can be substituted or unsubstituted. Alkyl groups can be optionally substituted with one or more moieties selected from halo, hydroxy, amino, thiol, alkylamino, alkoxy, haloalkyl, carboxy, amido, nitro, oxo, thioxo, and cyano.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted. Alkenyl groups can be optionally substituted with one or more moieties selected from halo, hydroxy, amino, thiol, alkylamino, alkoxy, haloalkyl, carboxy, amido, nitro, oxo, thioxo, and cyano.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted. Alkynyl groups can be optionally substituted with one or more moieties selected from halo, hydroxy, amino, thiol, alkylamino, alkoxy, haloalkyl, carboxy, amido, nitro, oxo, thioxo, and cyano.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is any number of suitable carbon atoms. Representative alkylene groups include, but are not limited to, methylene, ethylene, propylene, isopropylene, butylene, isobutylene, sec-butylene, pentylene and hexylene. Alkylene groups can be substituted or unsubstituted. Alkylene groups can be optionally substituted with one or more moieties selected from halo, hydroxy, amino, thiol, alkylamino, alkoxy, haloalkyl, carboxy, amido, nitro, oxo, thioxo, and cyano.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene. Alkenylen groups can be substituted or unsubstituted. Alkenylene groups can be optionally substituted with one or more moieties selected from halo, hydroxy, amino, thiol, alkylamino, alkoxy, haloalkyl, carboxy, amido, nitro, oxo, thioxo, and cyano.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene. Alkynylene groups can be substituted or unsubstituted. Alkynylene groups can be optionally substituted with one or more moieties selected from halo, hydroxy, amino, thiol, alkylamino, alkoxy, haloalkyl, carboxy, amido, nitro, oxo, thioxo, and cyano.

"Halogen" or "halo" refers to fluorine, chlorine, bromine and iodine.

"Amine" or "amino" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen). The alkyl, alkenyl, alkynyl, cycloalkyl, heterocycloalkyl, aryl, or heteroaryl groups can be optionally substituted with one or more moieties selected from halo, hydroxy, amino, thiol, alkylamino, alkoxy, haloalkyl, carboxy, amido, nitro, oxo, thioxo, and cyano.

"Hydroxyl" or "hydroxy" refers to an —OH group. The hydroxyl can be at any suitable carbon atom.

"Thiol" refers to an —SH group. The thiol group can be at any suitable carbon atom.

"Oxo" refers to a double bonded O group (═O, —C(O)—). The oxo group can be at any suitable carbon atom.

"Thioxo" refers to a double bonded S group (═S). The thioxo group can be at any suitable carbon atom.

"Nitro" refers to a —NO$_2$ group. The nitro group can be at any suitable carbon atom.

"Carboxy" refers to a carboxylic acid group of the formula —C(O)OH or —CO$_2$H.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. Cycloalkyl groups can be optionally substituted with one or more moieties selected from alkyl, alkenyl, alkynyl, halo, hydroxy, amino, alkylamino, alkoxy, haloalkyl, carboxy, amido, thiol, nitro, oxo, thioxo, and cyano. For example, cycloalkyl groups can be substituted with $C_{1-6}$ alkyl or oxo (═O), among many others.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized to form moietites including, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. Heterocycloalkyl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano. For example, heterocycloalkyl groups can be substituted with $C_{1-6}$ alkyl or oxo (═O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. Aryl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized to form moieties including, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. Heteroaryl groups can be optionally substituted with one or more moieties selected from alkyl, alkenyl, alkynyl, halo, hydroxy, amino, thiol, alkylamino, alkoxy, haloalkyl, carboxy, amido, nitro, oxo, thioxo, and cyano.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

"(Cycloalkyl)alkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary (cycloalkyl)alkyl groups include, but are not limited to, methyl-cyclopropyl, methyl-cyclobutyl, methyl-cyclopentyl and methyl-cyclohexyl.

"(Heterocycloalkyl)alkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heterocycloalkyl component is as defined above. (Heterocycloalkyl)alkyl groups can be substituted or unsubstituted.

"Arylalkyl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Examples of arylalkyl groups include, but are not limited to, benzyl and ethyl-benzene. Arylalkyl groups can be substituted or unsubstituted.

"Heteroarylalkyl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heteroaryl component is as defined within. Heteroarylalkyl groups can be substituted or unsubstituted.

"Carboxyalkyl" refers to a carboxy group linked to an alkyl, as described above, and generally having the formula —$C_{1-8}$ alkyl-C(O)OH. Any suitable alkyl chain is useful. Carboxyalkyl groups can be optionally substituted with one or more moieties selected from halo, hydroxy, amino, thiol, alkylamino, alkoxy, haloalkyl, carboxy, amido, nitro, oxo, thioxo, and cyano.

"Acyl" refers to an alkyl that contains an oxo substituted carbon at the point of attachment (—C(O)—$C_{1-8}$ alkyl). Any suitable alkyl chain is useful. Acyl groups can be optionally substituted with one or more moieties selected from halo, hydroxy, amino, thiol, alkylamino, alkoxy, haloalkyl, carboxy, amido, nitro, oxo, thioxo, and cyano.

"Hydroxyalkyl" refers to an alkyl group, as defined above, where at least one of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like. Hydroxyalkyl groups can be optionally substituted with one or more moieties selected from halo, thiol, amino, alkylamino, alkoxy, haloalkyl, carboxy, amido, nitro, oxo, thioxo, and cyano. One of skill in the art will appreciate that other hydroxyalkyl groups are useful in the present invention.

"Alkoxy" refers to an alkyl group having at least one bridging oxygen atom. The bridging oxygen atom can be anywhere within the alkyl chain (alkyl-O-alkyl) or the bridging oxygen atom can connect the alkyl group to the point of attachment (alkyl-O—). In some embodiments, the bridging oxygen atom is not present as a terminal hydroxy group (i.e., —OH). In some instances, the alkoxy contains 1, 2, 3, 4, or 5 bridging oxygen atoms. As for alkyl group, alkoxy groups can have any suitable number of carbon atoms, such as $C_{1-2}$, $C_{1-4}$, and $C_{1-6}$. Alkoxy groups include, for example, methoxy, ethoxy, propoxy, iso-propoxy, methyloxy-ethyloxy-ethyl ($C_1$—O—$C_2$—O—$C_2$—), etc. One example of an alkoxy group is polyethylene glycol (PEG) wherein the polyethylene glycol chain can include between 2 to 20 ethylene glycol monomers. Alkoxy groups can be optionally substituted with one or more moieties selected from halo, hydroxy, amino, thiol, alkylamino, haloalkyl, carboxy, amido, nitro, oxo, thioxo, and cyano. Alkoxy groups can be substituted or unsubstituted.

"Alkylamino" refers to an alkyl group as defined within, having one or more amino groups. The amino groups can be primary, secondary or tertiary. Alkylamino groups useful in the present invention include, but are not limited to, ethyl amine, propyl amine, isopropyl amine, ethylene diamine and ethanolamine. The amino group can link the alkylamino to the point of attachment with the rest of the compound, be at any position of the alkyl group, or link together at least two carbon atoms of the alkyl group. Alkylamino groups can be optionally substituted with one or more moieties selected from halo, hydroxy, thiol, alkylamino, alkoxy, haloalkyl, carboxy, amido, nitro, oxo, thioxo, and cyano. One of skill in the art will appreciate that other alkylaminos are useful in the present invention.

"Alkylthio" refers to an alkyl group as defined within, having one or more thiol groups. Alkylthio groups useful in the present invention include, but are not limited to, ethyl thiol, propyl thiol, and isopropyl thiol. The thiol group can link the alkylthio to the point of attachment with the rest of the compound, be at any position of the alkyl group, or link together at least two carbon atoms of the alkyl group. Alkylthio groups can be optionally substituted with one or more moieties selected from halo, hydroxy, amino, alkylamino, alkoxy, haloalkyl, carboxy, amido, nitro, oxo, thioxo, and cyano. One of skill in the art will appreciate that other alkylthio are useful in the present invention.

The term "oxyethyl" refers to a divalent radical having the formula —$OCH_2CH_2$—.

The term "wavy line" signifies the point of attachment of the substituent to the remainder of the molecule. When the wavy line is not depicted as being specifically appended to a specific ring atom, the point of attachment can be to any suitable atom of the substituent. For example, the wavy line in the following structure:

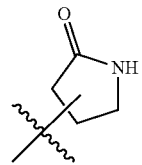

is intended to include, as the point of attachment, any of the substitutable atoms.

The term "regenerative medicine" refers to a branch of medicine that deals with the process of replacing, engineering or regenerating human cells, tissues, or organs to restore or establish normal function. In some embodiments, regenerative medicine includes growing tissues and organs in the laboratory and safely implanting them when the body cannot heal itself.

The term "supercooling" refers to the process of cooling a substance below a phase-transition temperature without the transition occurring. For example, supercooling can refer to the process of lowering the temperature of a liquid below its freezing point without solidification or crystallization.

The term "bioengineered tissue" refers to one or more synthetically created cells, tissues, or organs created for the purposes of regenerative medicine. In some embodiments, bioengineered tissue refers to cells, tissues, or organs that were developed in the laboratory. In some embodiments, bioengineered tissues refers to laboratory derived heart, liver, lung, kidney, pancreas, intestine, thymus, cornea, stem cells (e.g., human pluripotent stem cells, hematopoietic stem cells), lymphocytes, granulocytes, immune system cells, bone cells, organoids, embryonic cells, oocytes, sperm cells, blood platelets, nerve cells, or a combination thereof.

The term "cryoprotectant solution" refers to a solution used to reduce or prevent freezing damage caused by ice crystal formation. In some embodiments, the cryoprotectant solution comprises one or more peptoid polymers described herein. In other embodiments, the cryoprotectant solution comprises one or more peptoid polymers and one or more peptoid-peptide hybrids described herein. In some embodiments, the cryoprotectant solution protects a biological sample from freezing damage. In some embodiments, the cryoprotectant solution protects a non-biological sample from ice crystal formation. In some embodiments, the cryoprotectant solution preserves a biological sample for an amount of time longer than if the biological sample were not exposed to reduced temperatures.

The terms "vitrify" and "vitrification" mean the transformation of a substance into a glass (i.e., non-crystalline amorphous solid). In the context of water, vitrification refers to the transformation of water into a glass without the formation of ice crystals, as opposed to ordinary freezing, which results in ice crystal formation. Vitrification is often achieved through very rapid cooling and/or the introduction of agents that suppress ice crystal formation. On the other hand, "devitrify" and "devitrification" refer to the process of crystallization in a previously crystal-free (amorphous) glass. In the context of water ice, devitrification can mean the formation of ice crystals as the previously non-crystalline amorphous solid undergoes melting.

The term "peptoid polymer" or "peptoid" refers to a polyamide of between about 2 and 1,000 (e.g., between about 2 and 1,000, 2 and 950, 2 and 900, 2 and 850, 2 and 800, 2 and 750, 2 and 700, 2 and 650, 2 and 600, 2 and 550, 2 and 500, 2 and 450, 2 and 400, 2 and 350, 2 and 300, 2 and 250, 2 and 200, 2 and 150, 2 and 100, 2 and 90, 2 and 80, 2 and 70, 2 and 60, 2 and 50, 2 and 40, 2 and 30, 2 and 20, 2 and 10, 2 and 9, 2 and 8, 2 and 7, 2 and 6, 2 and 5, 2 and 4, or 2 and 3) peptoid monomers having substituents "$R^1$" on the amide nitrogen atoms. Optionally, a second, independently selected, substituent "$R^2$" can be attached to the carbon atom that is α- to the carbonyl group (i.e., attached to the α-carbon atom). $R^2$ can be, but is not limited to, H. In particular instances, a peptoid is a synthetic analog of a peptide wherein the side chains that would otherwise be attached to the α-carbon atoms are instead attached to the amide nitrogen atoms. In general, peptoids are synthetic polymers with controlled monomer sequences and lengths that can be made by automated solid-phase organic synthesis to include a wide variety of side chains having different chemical functions. $R^1$ groups bonded to the amide nitrogen atoms in the peptoid monomers can include, but are not limited to, H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl groups, wherein any of the cycloalkyl, heterocycloalkyl, aryl, or heteroaryl groups is optionally and independently substituted with one or more "$R^3$" groups. Each $R^3$ group can be independently selected from halogen, oxo, thioxo, —OH, —SH, sulfonamide, amino, $C_{1-8}$ alkyl, $C_{1-8}$ hydroxyalkyl, $C_{1-8}$ alkylamino, or $C_{1-8}$ alkylthio groups. Furthermore, $R^1$ groups can comprise the side chain of any of the amino acids alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), or tyrosine (Tyr). The term includes free amine forms as well as salt forms.

The terms "polar peptoid monomer" and "peptoid monomer having a polar side chain" are used interchangeably to refer to peptoid monomers in which the substituent "$R^1$" is a polar side chain, or both $R^1$ and the substituent "$R^2$" are polar side chains. Commonly, a polar side chain will comprise a hydroxyl group and/or an atom (e.g., sulfur, nitrogen, oxygen) that can participate in hydrogen bonding. In some instances, a polar side chain includes atoms or groups that are more hydrophobic than polar in nature (e.g., aromatic rings). In these instances, the side chain also includes atoms or groups such that the entire side chain is more polar than hydrophobic. As a non-limiting example, a polar side chain can contain an aromatic ring to which one or more hydroxyl groups are attached.

In some embodiments, the peptoid polymer comprises one or more polar peptoid monomers selected from the group consisting of Nop, Nhp, Nhe, Ndp, Nyp, Nep, Ndh, and a combination thereof.

The terms "hydrophobic peptoid monomer" and "peptoid monomer having a hydrophobic side chain" are used interchangeably to refer to peptoid monomers in which the substituent "$R^1$" is a hydrophobic side chain (e.g., not polar), or both IV and the substituent "$R^2$" are hydrophobic side chains. Commonly, a hydrophobic side chain comprises an unsubstituted alkyl, unsubstituted cycloalkyl, or an unsubstituted aromatic group.

In some embodiments, the peptoid polymer comprises one or more hydrophobic peptoid monomers selected from the group consisting of Nsb, Nib, Nbu, Npr, Nip, Nme, and a combination thereof.

The term "peptoid-peptide hybrid" refers to an oligomer that is composed of both peptoid monomer units and alpha amino acids (i.e., peptide units). The term includes free amine forms as well as salt forms.

The terms "polypeptide," "peptide," and "protein" are used interchangeably herein to refer to a polymer of amino acid residues, or an assembly of multiple polymers of amino acid residues.

The term "amino acid" includes but is not limited to naturally-occurring α-amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid (i.e., the D-amino acid).

Naturally-occurring amino acids are those encoded by the genetic code, as well as those amino acids that are later modified (e.g., hydroxyproline, γ-carboxyglutamate, and O-phosphoserine). Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

III. Detailed Description of the Embodiments

Provided herein are methods for cryopreserving a population of cells such as, e.g., cells present in a tissue or organ. In some aspects, the method comprises contacting a population of cells with a peptoid polymer comprising one or more polar peptoid monomers, and cooling the population of cells to a temperature of from 0° C. to about −20° C. for a desired time period, e.g., at least about 3 hours. The supercooling methods of the present invention advantageously provide excellent post-thaw cell survival and recovery of tissues and organs suitable for transplantation.

A. Peptoid Polymers

In some aspects, provided herein is a peptoid polymer of formula (I):

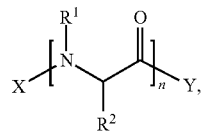

(I)

a tautomer thereof or stereoisomer thereof,
wherein:
each $R^1$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl,
wherein at least one instance of $R^1$ is $C_{1-18}$ hydroxyalkyl, and
wherein any of the cycloalkyl, heterocycloalkyl, aryl, and heteroaryl groups is optionally and independently substituted with one or more $R^3$ groups;
each $R^2$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted $C_{1-18}$ alkylamino, optionally substituted $C_{1-18}$ alkylthio, and optionally substituted carboxyalkyl;
each $R^3$ is independently selected from the group consisting of halogen, oxo, thioxo, —OH, —SH, amino, $C_{1-8}$ alkyl, $C_{1-8}$ hydroxyalkyl, $C_{1-8}$ alkylamino, and $C_{1-8}$ alkylthio;
X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or
alternatively X and Y are taken together to form a covalent bond; and
the subscript n, representing the number of monomers in the polymer, is between 2 and 50.

In some embodiments, all instances of $R^1$ are not hydroxyethyl when n is between 3 and 7. In some embodiments, each instance of $R^1$ in the peptoid polymer is selected from the group consisting of:

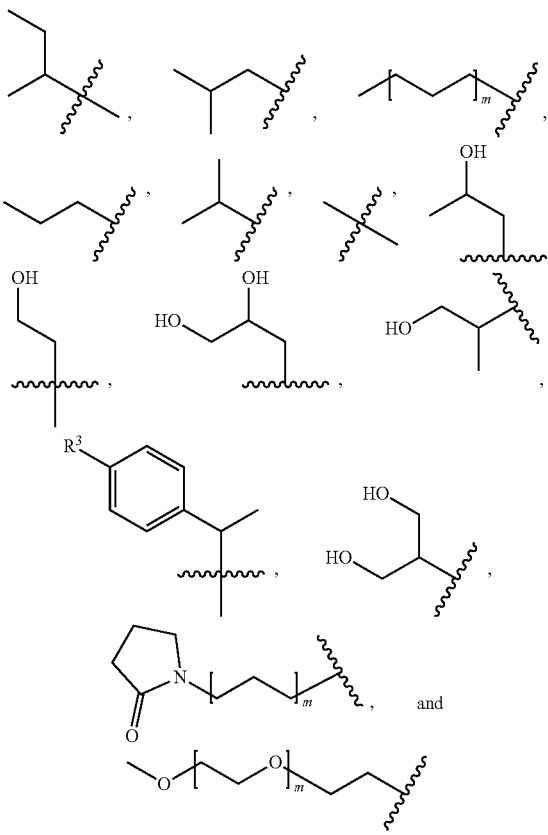

wherein: m is between 1 and 8; and $R^3$ is selected from the group consisting of H, $C_{1-8}$ alkyl, hydroxyl, thiol, nitro, amine, oxo, and thioxo. In some embodiments, the repeating unit, m, can be between 1 and 2, 1 and 3, 1 and 4, 1 and 5, 1 and 6, or 1 and 7. In some embodiments, the repeating unit, m, is 1, 2, 3, 4, 5, 6, 7, or 8.

In some embodiments, one or more IV monomers has a structure according to Ria:

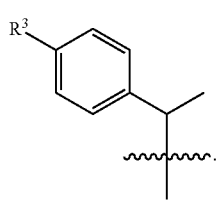

R$^{1a}$

In some embodiments, each R$^{1a}$ group is independently selected from

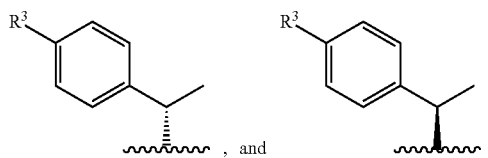

In some embodiments, a mixture of the two stereoisomers are chosen. In some embodiments, only the R stereoisomer of the monomer is chosen. In some embodiments, only the S stereoisomer of this monomer is chosen.

In some embodiments, one or more IV monomers has a structure according to Rib:

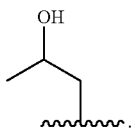

R$^{1b}$

In some embodiments, each Rib group is independently selected from

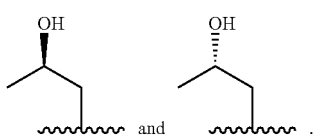

In some embodiments, a mixture of the two stereoisomers are chosen. In some embodiments, only the R stereoisomer of the monomer is chosen. In some embodiments, only the S stereoisomer of this monomer is chosen.

In some embodiments, one or more IV monomers has a structure according to R$^{1c}$:

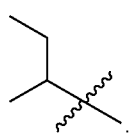

R$^{1c}$

In some embodiments, each R$^{1c}$ group is independently selected from

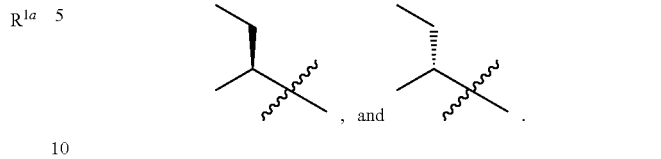

In some embodiments, a mixture of the two stereoisomers are chosen. In some embodiments, only the R stereoisomer of the monomer is chosen. In some embodiments, only the S stereoisomer of this monomer is chosen.

In some embodiments, one or more IV monomers has a structure according to Ria:

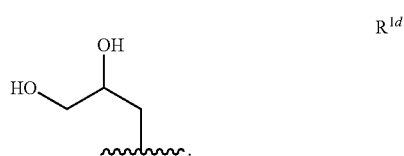 [SMILES: *CC(O)CO]

R$^{1d}$

In some embodiments, each Rid group is independently selected from

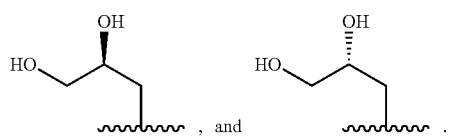 [SMILES: *C[C@H](O)CO ; *C[C@@H](O)CO]

In some embodiments, a mixture of the two stereoisomers are chosen. In some embodiments, only the R stereoisomer of the monomer is chosen. In some embodiments, only the S stereoisomer of this monomer is chosen.

In some embodiments, one or more R$^1$ monomers has a structure according to R$^{1e}$:

R$^{1e}$

In some embodiments, each R$^{1e}$ group is independently selected from

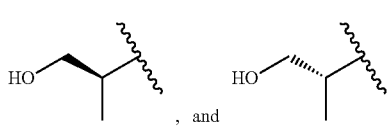

In some embodiments, a mixture of the two stereoisomers are chosen. In some embodiments, only the R stereoisomer of the monomer is chosen. In some embodiments, only the S stereoisomer of this monomer is chosen.

Whenever any monomer herein does not indicate stereochemistry, any stereoisomer may be used. In some embodiments, a mixture of the two stereoisomers are chosen. In embodiments comprising a mixture of stereoisomers, the ratio of R to S stereoisomer of the monomer in the peptoid polymer can range from about 95:5 to about 90:10, from about 90:10 to about 85:15, from about 85:15 to about 80:20, from about 80:20 to about 75:25, from about 75:25 to about 70:30, from about 70:30 to about 65:35, from about 65:35 to about 60:40, from about 60:40 to about 55:45, from about 55:45 to about 50:50, from about 50:50 to about 45:55, from about 45:55 to about 40:60, from about 40:60 to about 35:65, from about 35:65 to about 30:70, from about 30:70 to about 25:75, from about 25:75 to about 20:80, from about 20:80 to about 15:85, from about 15:85 to about 10:90, or from about 10:90 to about 5:95. In some embodiments, only the R stereoisomer of the monomer is chosen. In some embodiments, only the S stereoisomer of the monomer is chosen.

Whenever a particular stereochemistry is shown with a wedge or a dashed line, the monomer is substantially free of other stereoisomers. In some embodiments, substantially free means at least 70% pure. In some embodiments, substantially free means at least 80% pure. In some embodiments, substantially free means at least 90% pure. In some embodiments, substantially free means at least 95% pure. In some embodiments, substantially free means at least 99% pure. In some embodiments, substantially free means at least 99.9% pure.

In some embodiments, each instance of $R^1$ in the peptoid polymer is selected from the group consisting of:

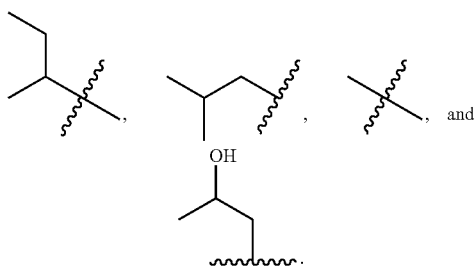

In some embodiments, at least 2, 3, 4, 5, 6, 7, 8, 9, 10, 11, 12, 13, 14, 15, 16, 17, 18, 19, 20, or more instances of $R^1$ in the peptoid polymer are independently selected $C_{1-18}$ hydroxyalkyl groups (e.g., independently selected $C_{1-6}$ hydroxyalkyl groups). In some embodiments, each instance of $R^1$ in the peptoid polymer is a $C_{1-18}$ hydroxyalkyl group. In some embodiments, each instance of $R^1$ is a $C_{1-6}$ hydroxyalkyl group. In some embodiments, each instance of $R^1$ is the same $C_{1-6}$ hydroxyalkyl group. In some embodiments, each instance of $R^1$ is an hydroxyalkyl group where the length of the alkyl in each hydroxyalkyl group is selected from 1, 2, 3, 4, 5, 6, 7, 8, 9, 10, 11, 12, 13, 14, 15, 16, 17, 18 or more carbon atoms. In some embodiments the hydroxyalkyl group contains 1, 2, 3, 4, 5, 6, 7, or 8 hydroxy substitutions. In some embodiments, each instance of $R^1$ is:

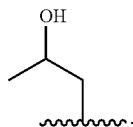

In some embodiments, each instance of $R^2$ is H. In some embodiments, at least one $R^2$ is a halogen.

In some embodiments, the sequence length of the peptoid polymer, n, is between 3 and 25. In some embodiments, the sequence length of the peptoid polymer, n, is between 5 and 25. In some embodiments, the sequence length of the peptoid polymer, n, is between 6 and 50. In some embodiments, the sequence length of the peptoid polymer, n, is between 6 and 25. In some embodiments, the sequence length of the peptoid polymer, n, is between 6 and 20. In some embodiments, the sequence length of the peptoid polymer, n, is between 8 and 50. In some embodiments, the sequence length of the peptoid polymer, n, is between 8 and 25. In some embodiments, the sequence length of the peptoid polymer, n, is between 8 and 20. In some embodiments, the sequence length of the peptoid polymer, n, can be between from about 10 to about 28, from about 12 to about 26, from about 14 to about 24, from about 16 to about 22, or from about 18 to about 20. In some embodiments, the sequence length of the peptoid polymer, n, can be between from about 8 to about 50, from about 8 to about 45, from about 8 to about 40, from about 8 to about 35, from about 8 to about 30, from about 10 to about 25, from about 10 to about 20, or from about 10 to about 15. In some embodiments, the sequence length of the peptoid polymer, n, can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some embodiments, X and Y are H, optionally substituted $C_{1-8}$ alkylamino, —OH, —SH, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen. In some embodiments, X is an acetyl group. In some embodiments, Y is carboxy.

In some embodiments, X and Y of the peptoid polymer are taken together to form a covalent bond. The formation of a covalent bond between X and Y results in a circularized form of the peptoid polymer in which the terminal $NR^1$ group and the terminal C=O group are linked, as shown below.

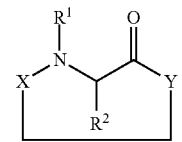

In some embodiments, the peptoid polymer consists of monomer units selected from the group of monomers set forth in Table 1. A person of skill in the art will recognize that the bounds of this invention are not limited to the monomers listed in Table 1, and that any useful N-substituted substituent can be used as an N-substituted peptoid monomer. In some embodiments, the N-substituted substituent on the N-substituted peptoid monomer is any of the side chains of the amino acids alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), or tyrosine (Tyr).

TABLE 1

| Structure | Name | Code |
|---|---|---|
| | 2-(sec-butylamino)acetic acid | Nsb |
| | 2-((2-hydroxypropyl)amino)acetic acid | Nhp |
| | 2-(isobutylamino)acetic acid | Nib |
| | 2-((2-hydroxyethyl)amino) acetic acid | Nhe |
| | 2-(butylamino)acetic acid | Nbu |
| | 2-((2,3-dihydroxypropyl)amino)acetic acid | Ndp |
| | 2-(propylamino)acetic acid | Npr |

TABLE 1-continued

| Structure | Name | Code |
|---|---|---|
| | 2-((1-hydroxypropan-2-yl)amino)acetic acid | Nyp |
| | 2-(isopropylamino)acetic acid | Nip |
| | 2-((1-(4-hydroxyphenyl)ethyl)amino)acetic acid | Nep |
| | 2-(methylamino)acetic acid | Nme |
| | 2-((1,3-dihydroxypropan-2-yl)amino)acetic acid | Ndh |
| | 2-((3-(2-oxopyrrolidin-1-yl)propyl)amino)acetic acid | Nop |
| | 2-(2-methoxyethylamino) acetic acid | Nmo |

TABLE 1-continued

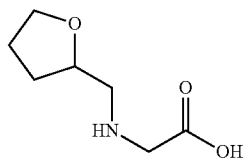

2-((2-tetrahydrofuran-2-yl)methylamino)acetic acid
Ntf

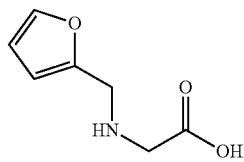

2-(furan-2-ylmethylamino)acetic acid
Nff

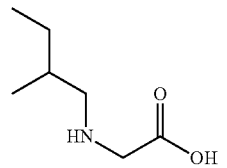

2-(2-methylbutylamino)acetic acid
Nmb

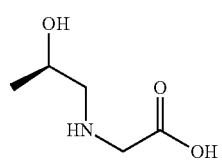

2-(R)-(2-hydroxypropylamino)acetic acid
Nrh

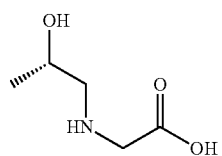

2-(S)-(2-hydroxypropylamino)acetic acid
Nsh

TABLE 1-continued

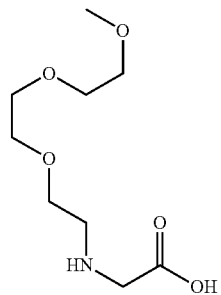

2-(2-(2-(2-methoxyethoxy)ethoxy)ethylamino)acetic acid
N3p

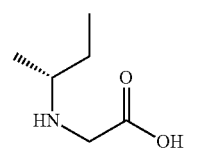

(2-(R)-sec-butylamino)acetic acid
Nbr

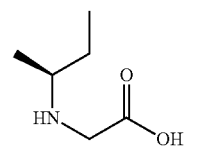

(2-(S)-sec-butylamino)acetic acid
Nbs

In some embodiments, the peptoid polymer is selected from the group of peptoid polymers set forth in Table 2, Table 3, Table 4, Table 5, Table 6, Table 7, Table 8, Table 9, or Table 10.

TABLE 2

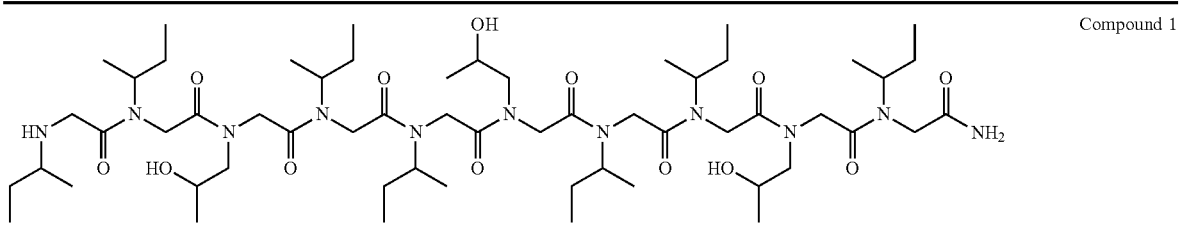

Compound 1

TABLE 2-continued
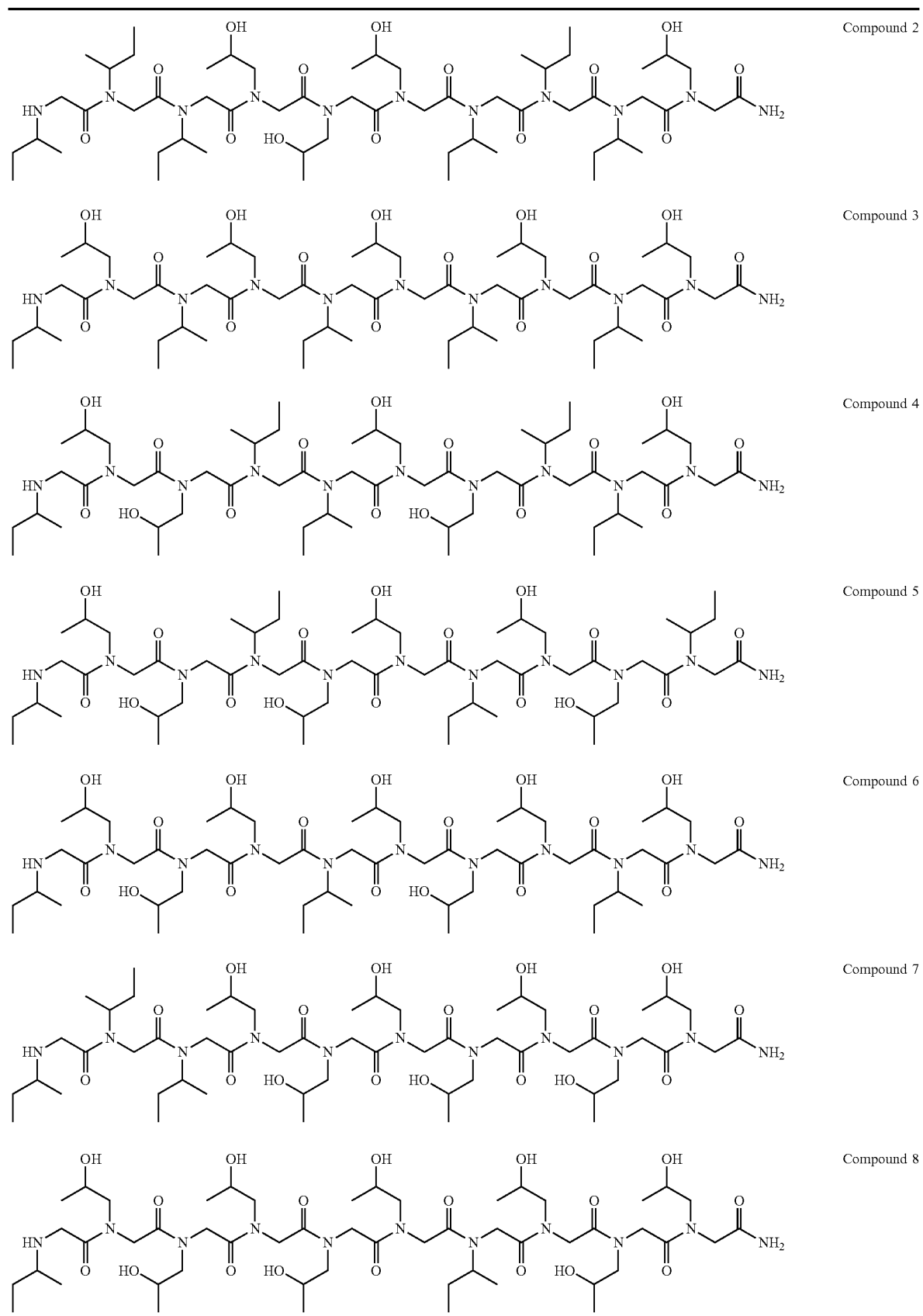

TABLE 2-continued

| | |
|---|---|
| [chemical structure] | Compound 9 |
| [chemical structure] | Compound 10 |
| [chemical structure] | Compound 11 |
| [chemical structure] | Compound 12 |
| [chemical structure] | Compound 13 |

TABLE 3

| | |
|---|---|
| [chemical structure] | Compound 14 |

TABLE 3-continued
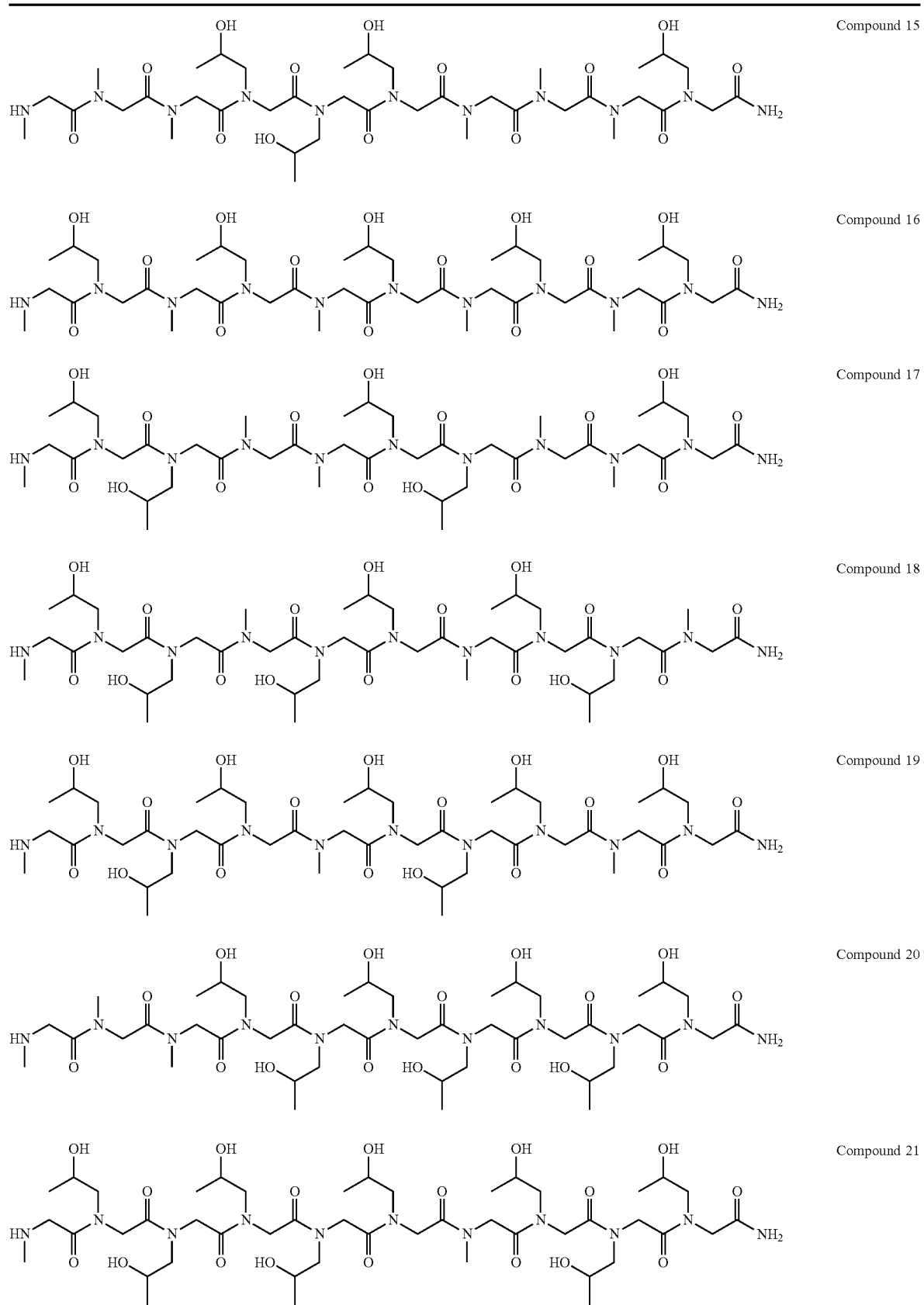
Compound 15
Compound 16
Compound 17
Compound 18
Compound 19
Compound 20
Compound 21

TABLE 3-continued
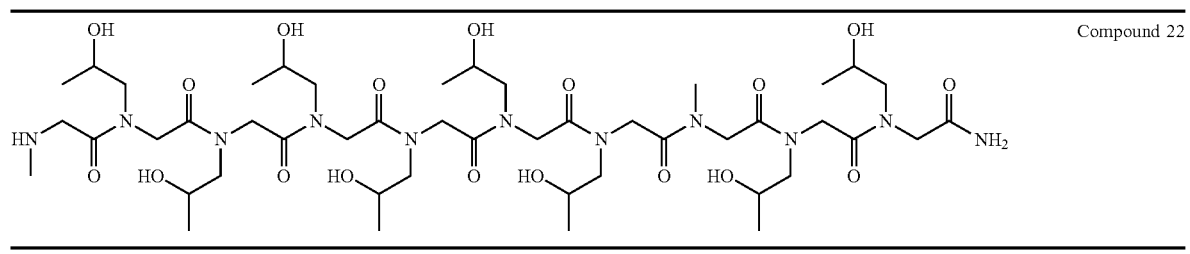
Compound 22
TABLE 4
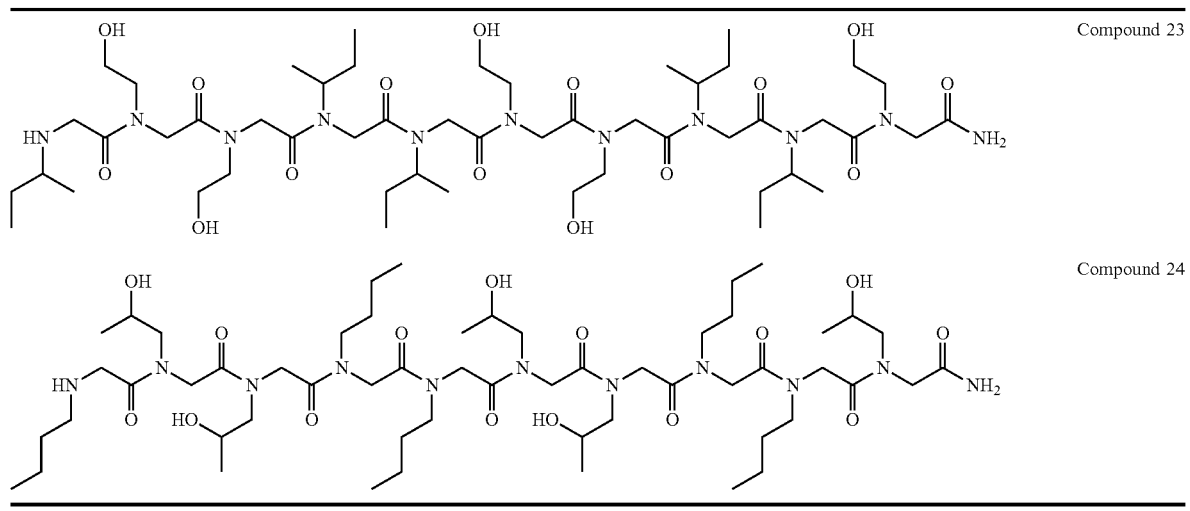
Compound 23
Compound 24
TABLE 5
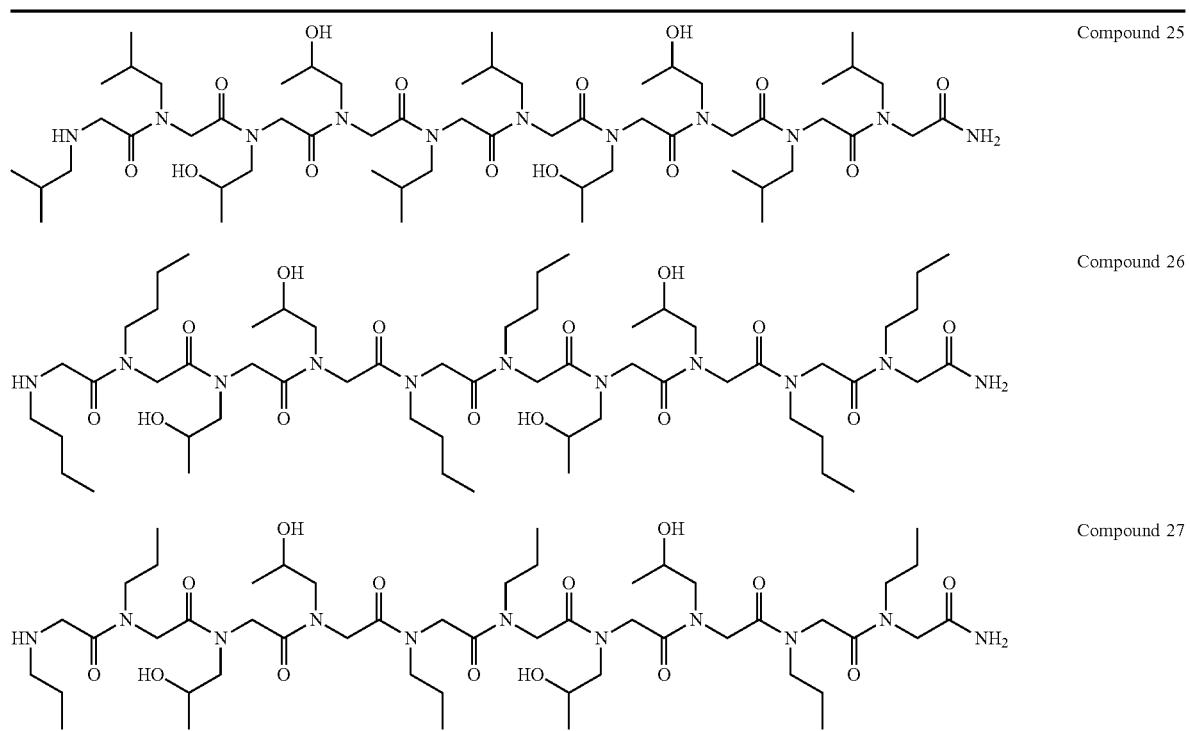
Compound 25
Compound 26
Compound 27

TABLE 5-continued
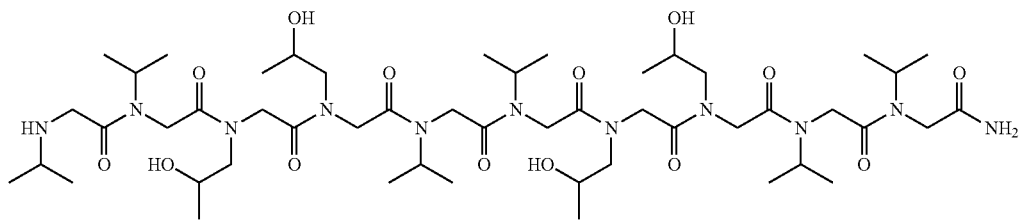 [SMILES: CC(O)CN(CC(=O)N(CC(=O)N(CC(=O)N(CC(=O)N(CC(=O)N(CC(=O)N(CC(=O)N(CC(N)=O)C(C)C)C(C)C)CC(C)O)CC(C)O)C(C)C)C(C)C)CC(C)O)C(=O)CN(C(=O)CNC(C)C)C(C)C]
Compound 28
TABLE 6
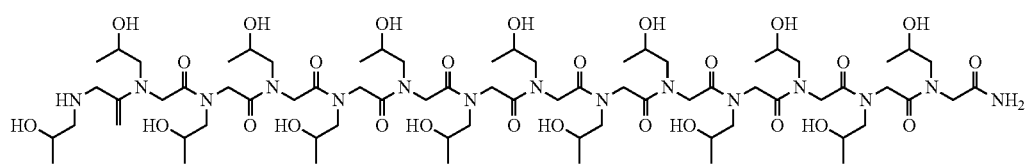 [SMILES: C=C(CNCC(C)O)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(N)=O)CC(C)O)CC(C)O)CC(C)O)CC(C)O)CC(C)O)CC(C)O)CC(C)O)CC(C)O)CC(C)O)CC(C)O)CC(C)O)CC(C)O)CC(C)O]
Compound 29
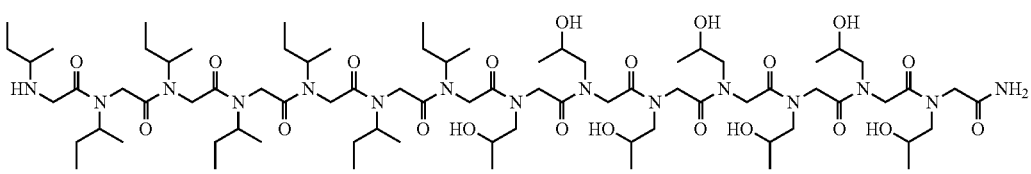 [SMILES: CCC(C)NCC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(N)=O)CC(C)O)CC(C)O)CC(C)O)CC(C)O)CC(C)O)CC(C)O)CC(C)O)C(C)CC)C(C)CC)C(C)CC)C(C)CC)C(C)CC)C(C)CC]
Compound 30
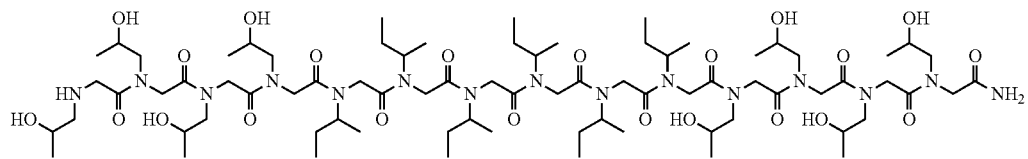 [SMILES: CCC(C)N(CC(=O)N(CC(=O)N(CC(=O)N(CC(=O)N(CC(N)=O)CC(C)O)CC(C)O)CC(C)O)CC(C)O)C(=O)CN(C(=O)CN(C(=O)CN(C(=O)CN(C(=O)CN(C(=O)CN(CC(C)O)C(=O)CN(CC(C)O)C(=O)CN(CC(C)O)C(=O)CNCC(C)O)C(C)CC)C(C)CC)C(C)CC)C(C)CC)C(C)CC]
Compound 31
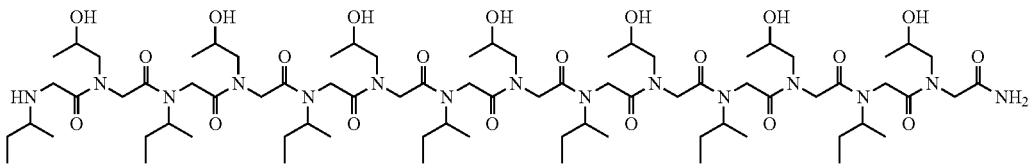 [SMILES: CCC(C)NCC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(N)=O)CC(C)O)C(C)CC)CC(C)O)C(C)CC)CC(C)O)C(C)CC)CC(C)O)C(C)CC)CC(C)O)C(C)CC)CC(C)O)C(C)CC)CC(C)O]
Compound 32
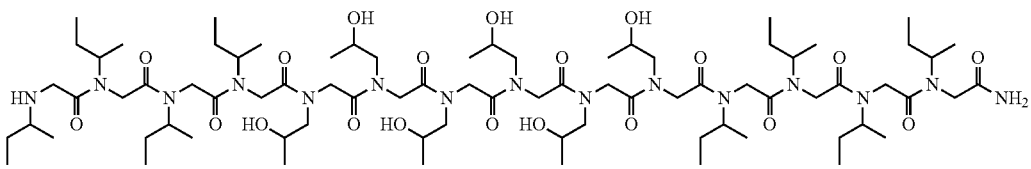 [SMILES: CCC(C)NCC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(N)=O)C(C)CC)C(C)CC)C(C)CC)C(C)CC)CC(C)O)CC(C)O)CC(C)O)CC(C)O)CC(C)O)CC(C)O)C(C)CC)C(C)CC)C(C)CC]
Compound 33
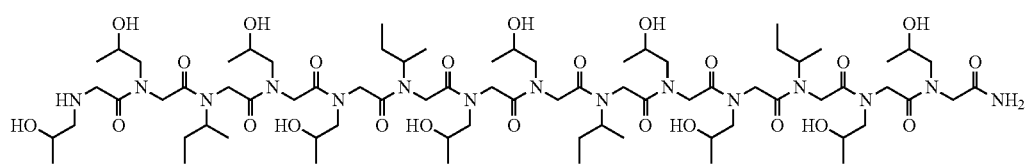 [SMILES: CCC(C)N(CC(=O)N(CC(=O)N(CC(=O)N(CC(=O)N(CC(=O)N(CC(=O)N(CC(=O)N(CC(=O)N(CC(=O)N(CC(=O)N(CC(=O)N(CC(N)=O)CC(C)O)CC(C)O)C(C)CC)CC(C)O)CC(C)O)C(C)CC)CC(C)O)CC(C)O)C(C)CC)CC(C)O)CC(C)O)C(=O)CN(CC(C)O)C(=O)CNCC(C)O]
Compound 34

TABLE 7
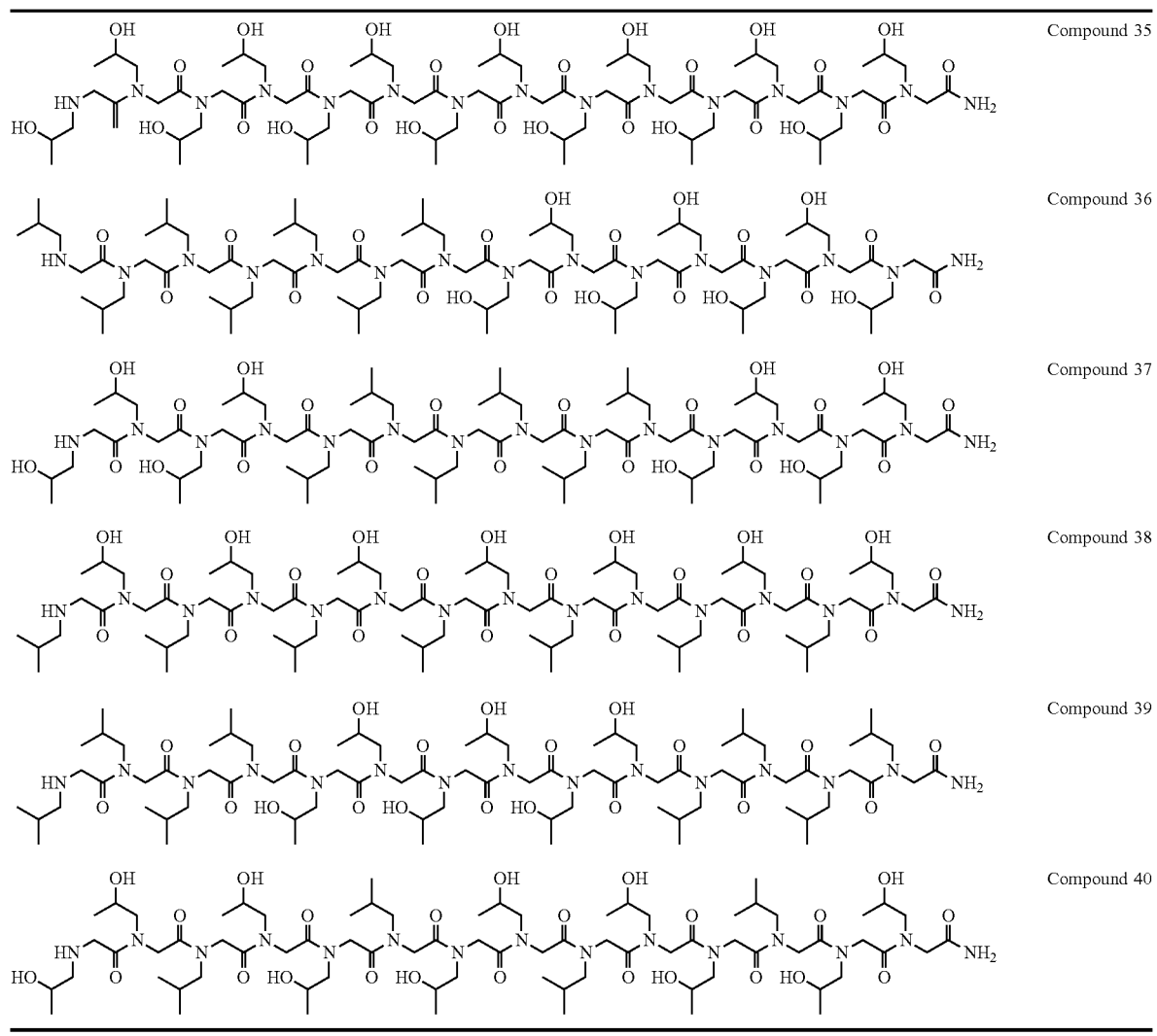
TABLE 8
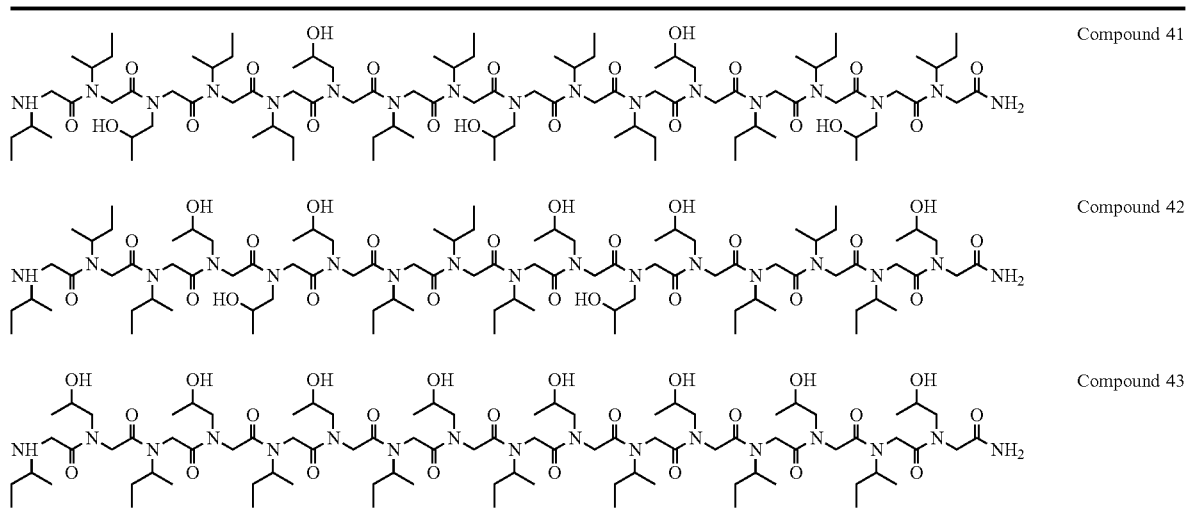

TABLE 8-continued
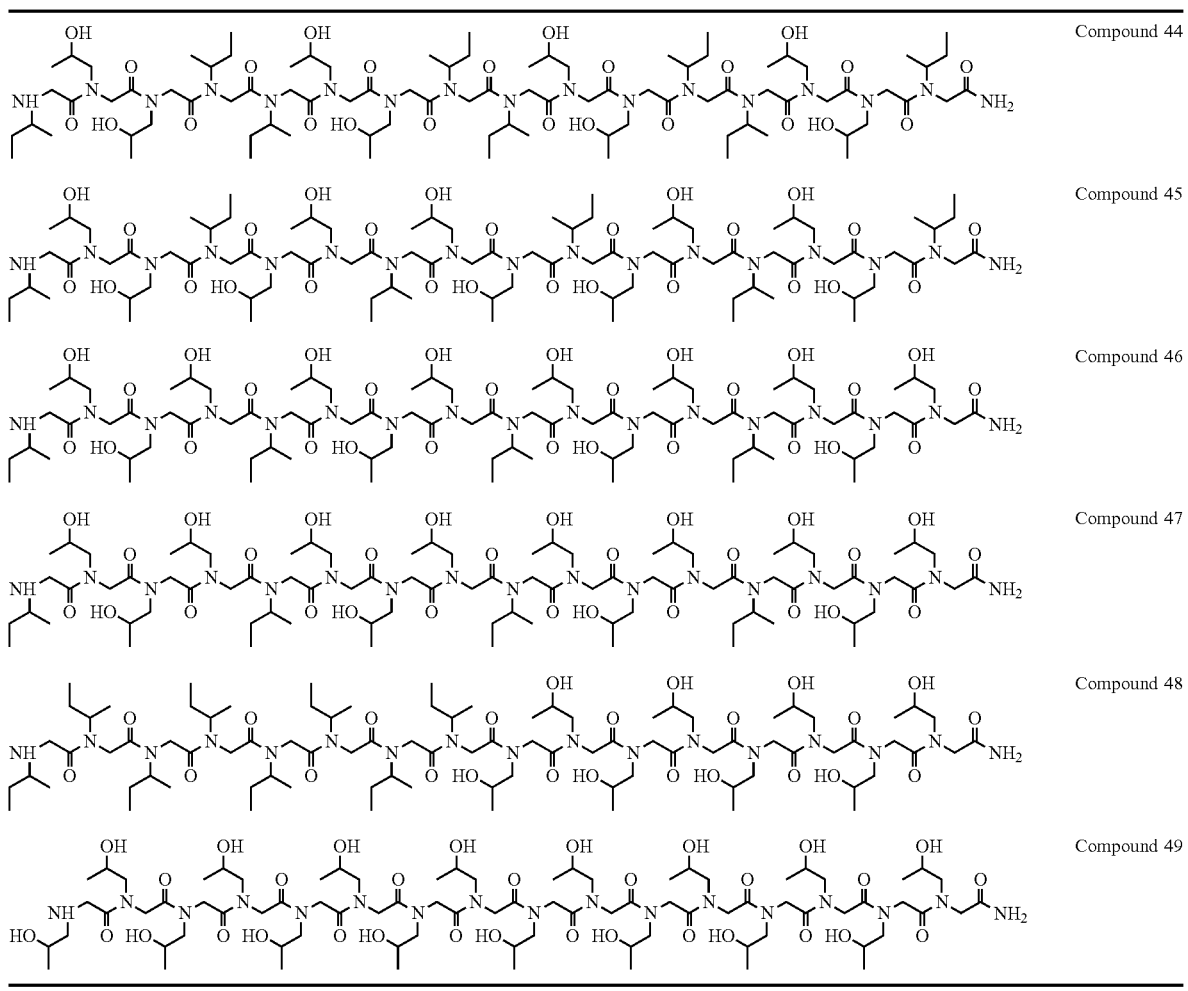
Compound 44
Compound 45
Compound 46
Compound 47
Compound 48
Compound 49

TABLE 9

Compound 50, Compound 51, Compound 52, Compound 53, Compound 54, Compound 55

TABLE 9-continued
| Compound 56 | Compound 57 |
|---|---|
| 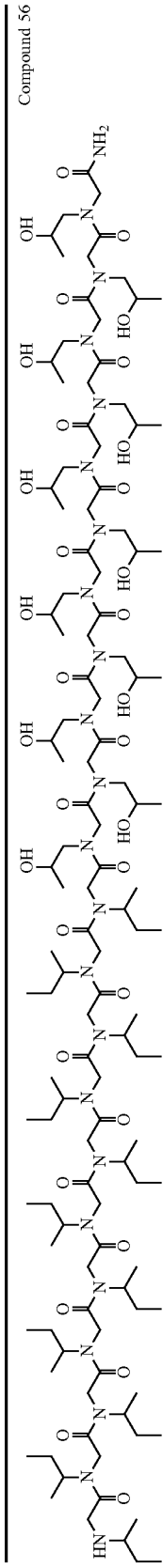 | 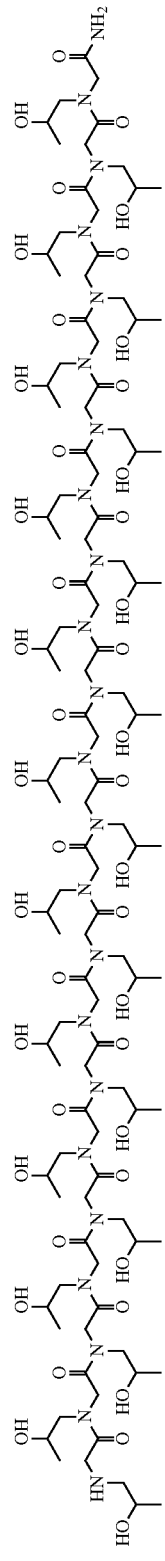 |

TABLE 10
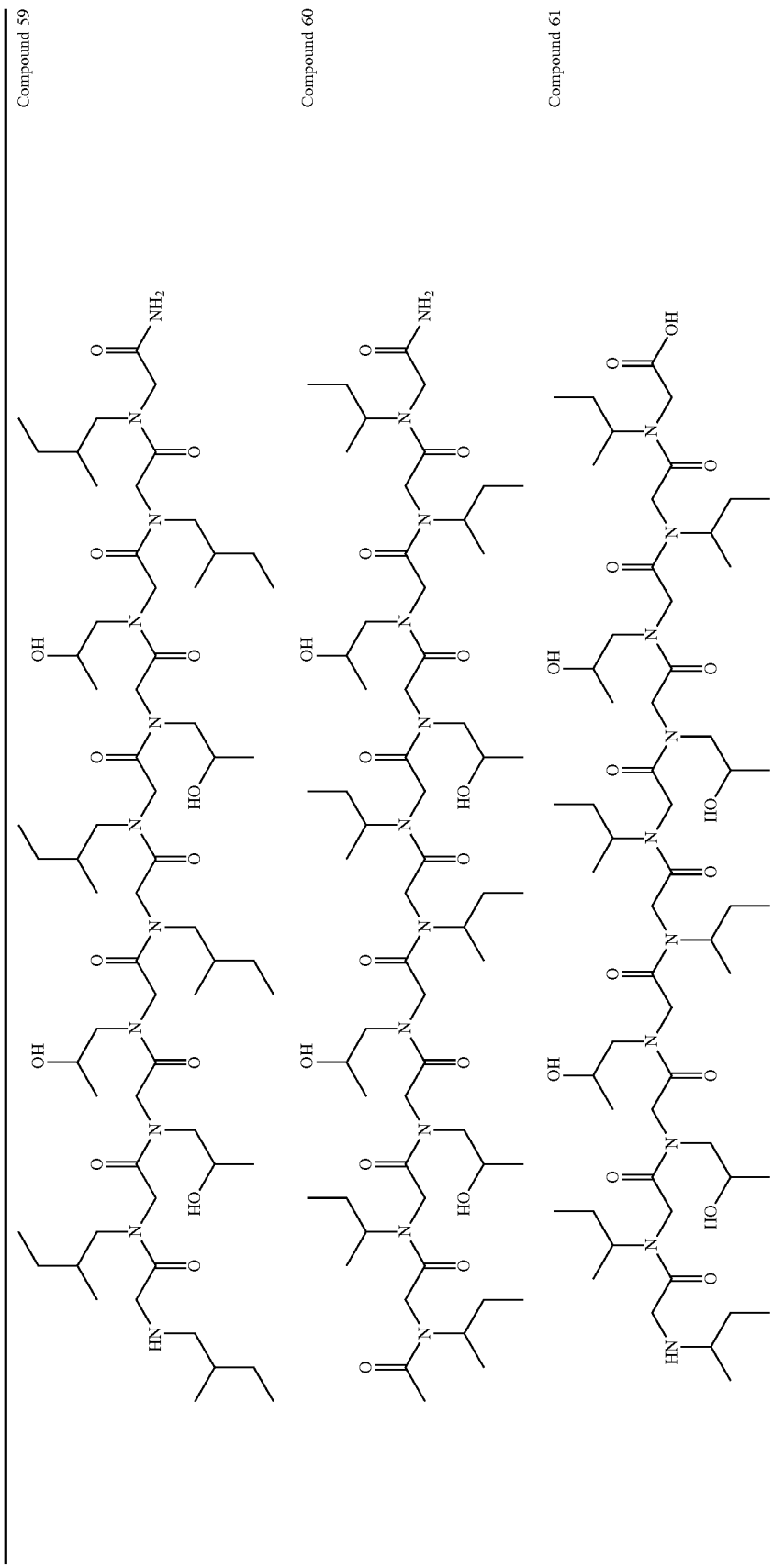

TABLE 10-continued
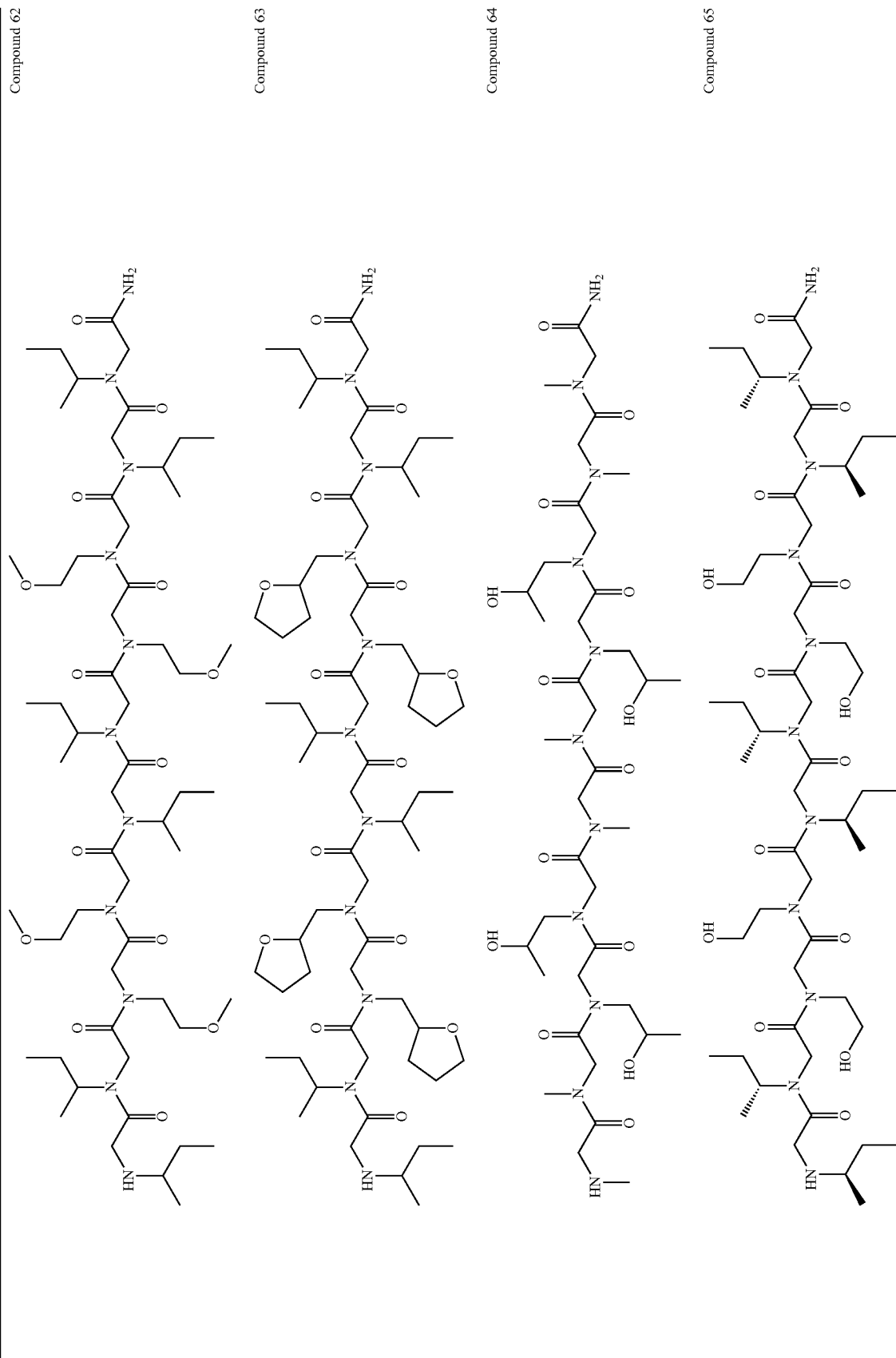

TABLE 10-continued
Compound 66
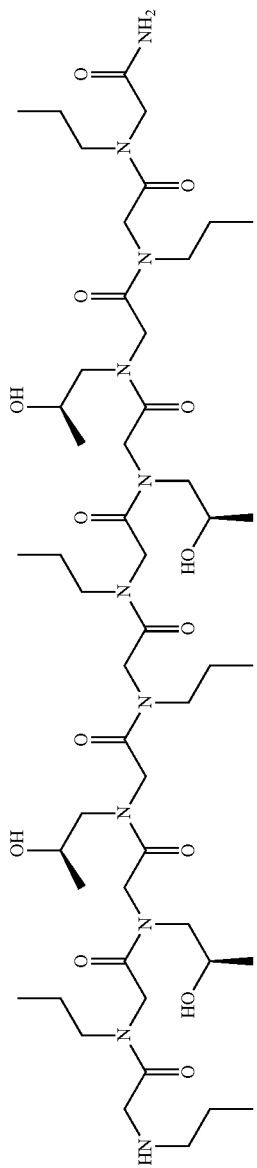
Compound 67
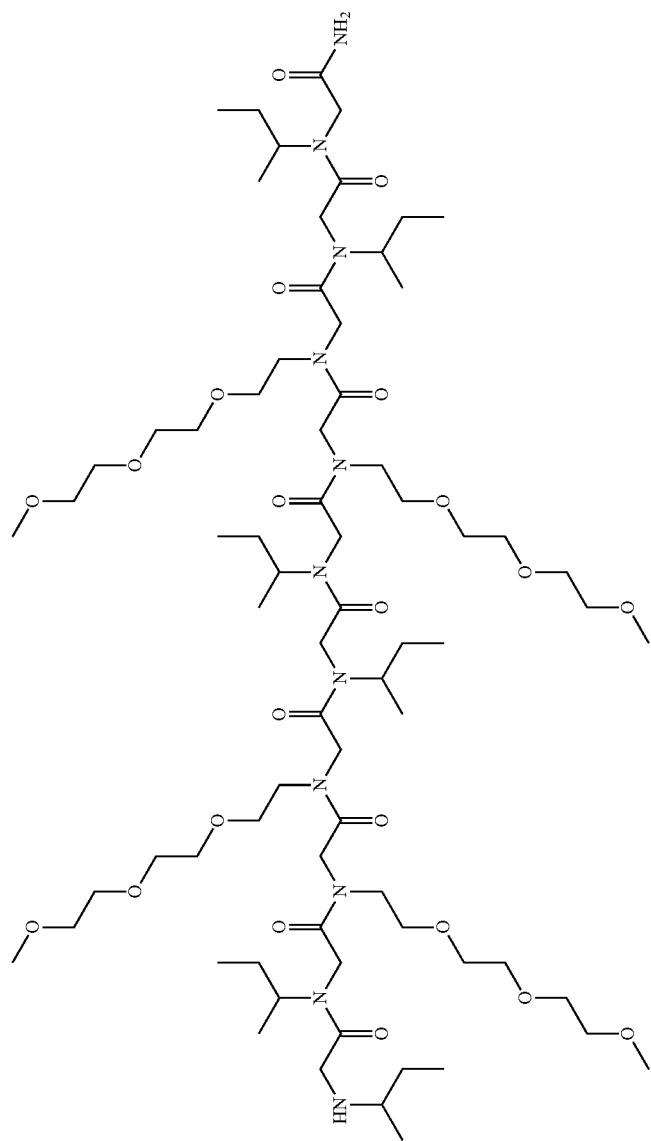

TABLE 10-continued
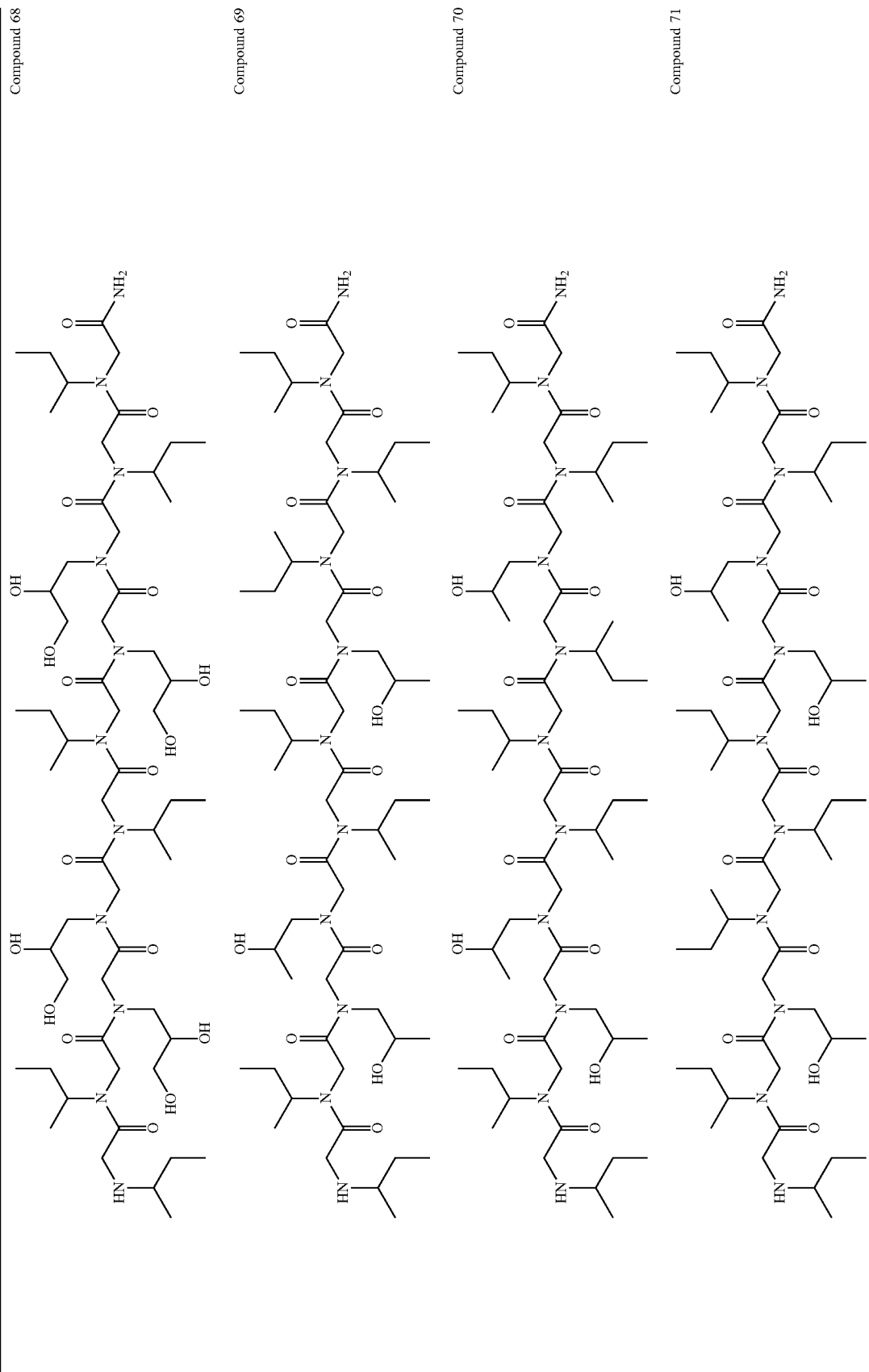

TABLE 10-continued
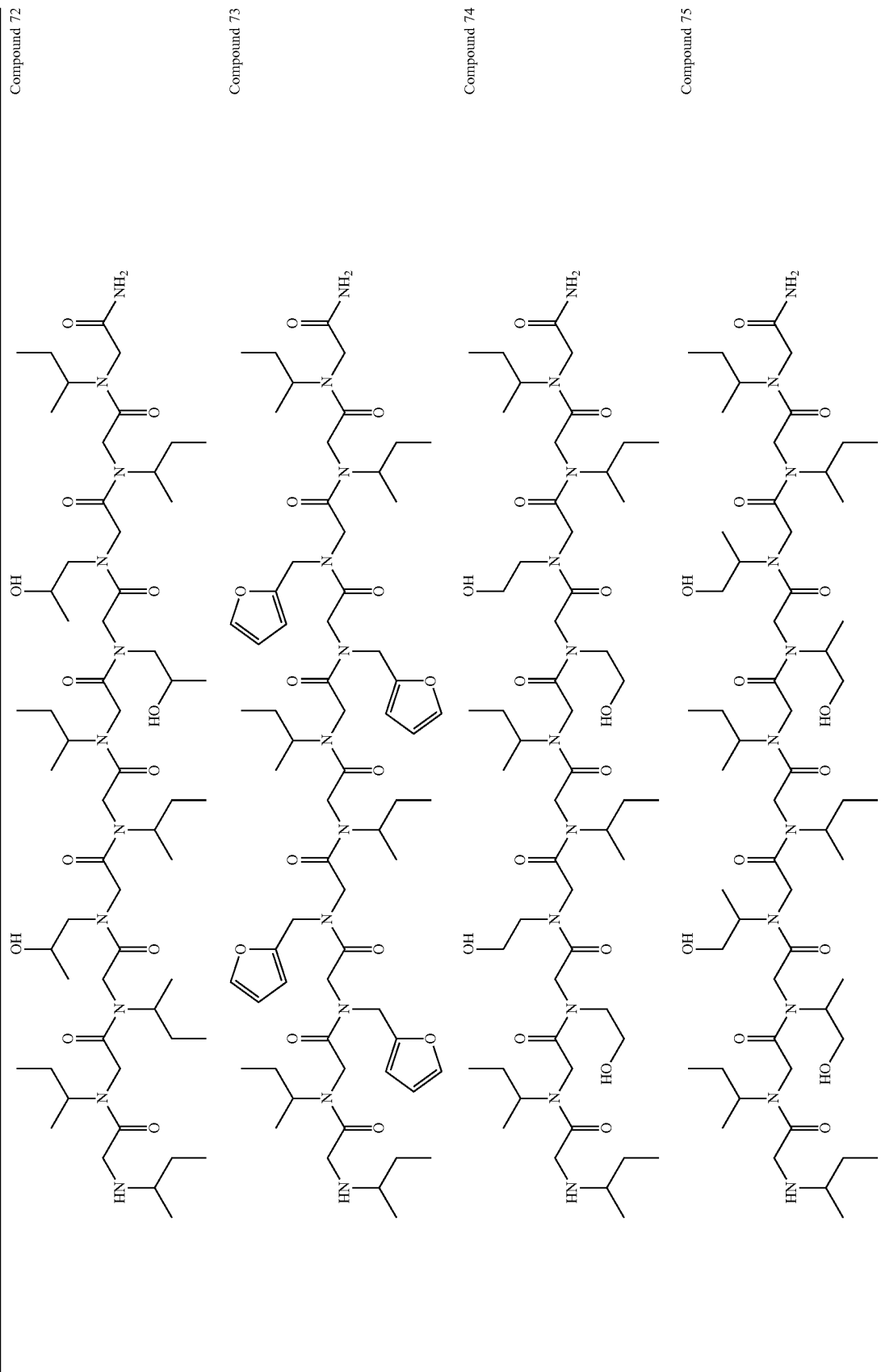

TABLE 10-continued
| Compound 76 | Compound 77 | Compound 78 |
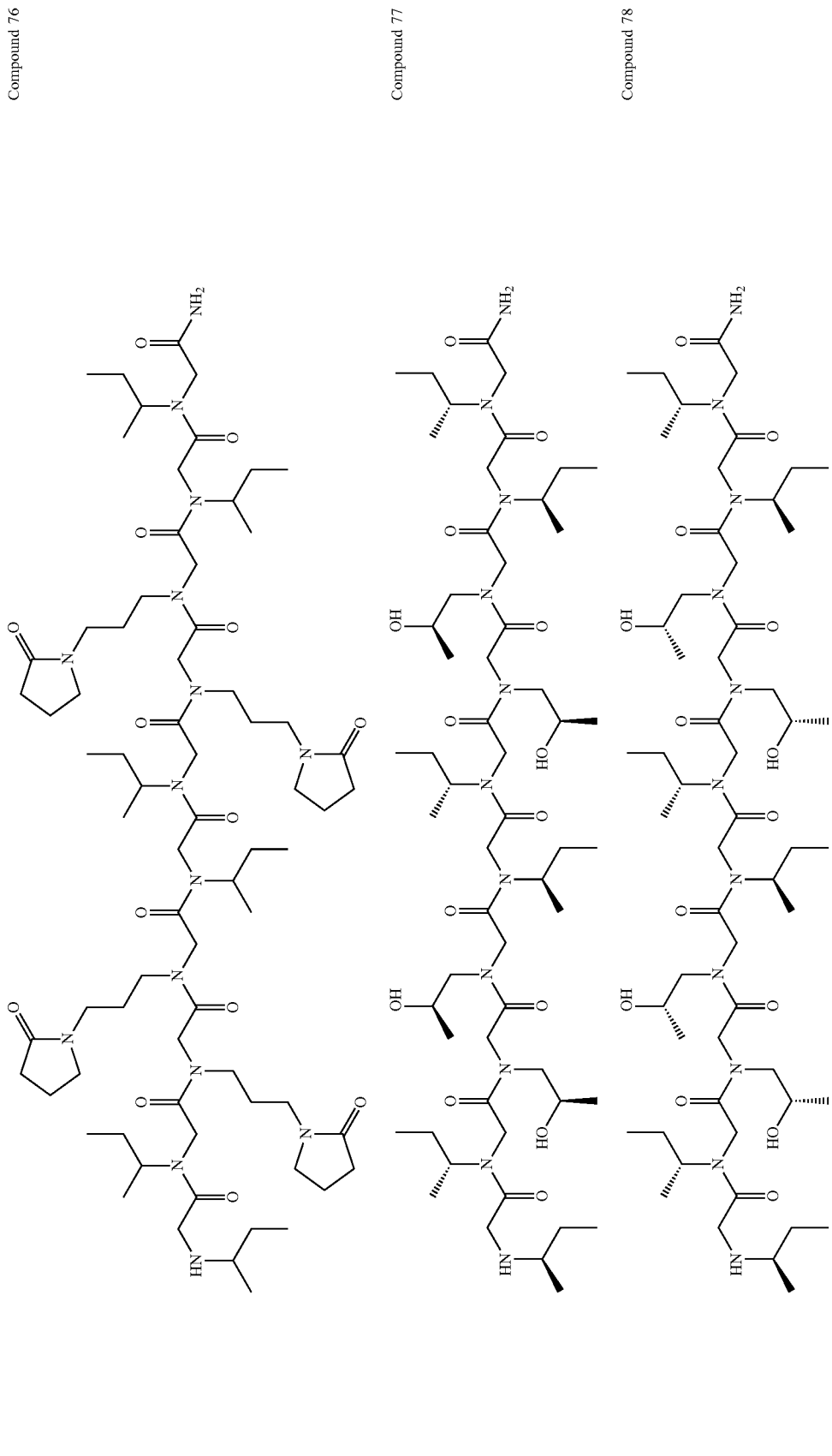

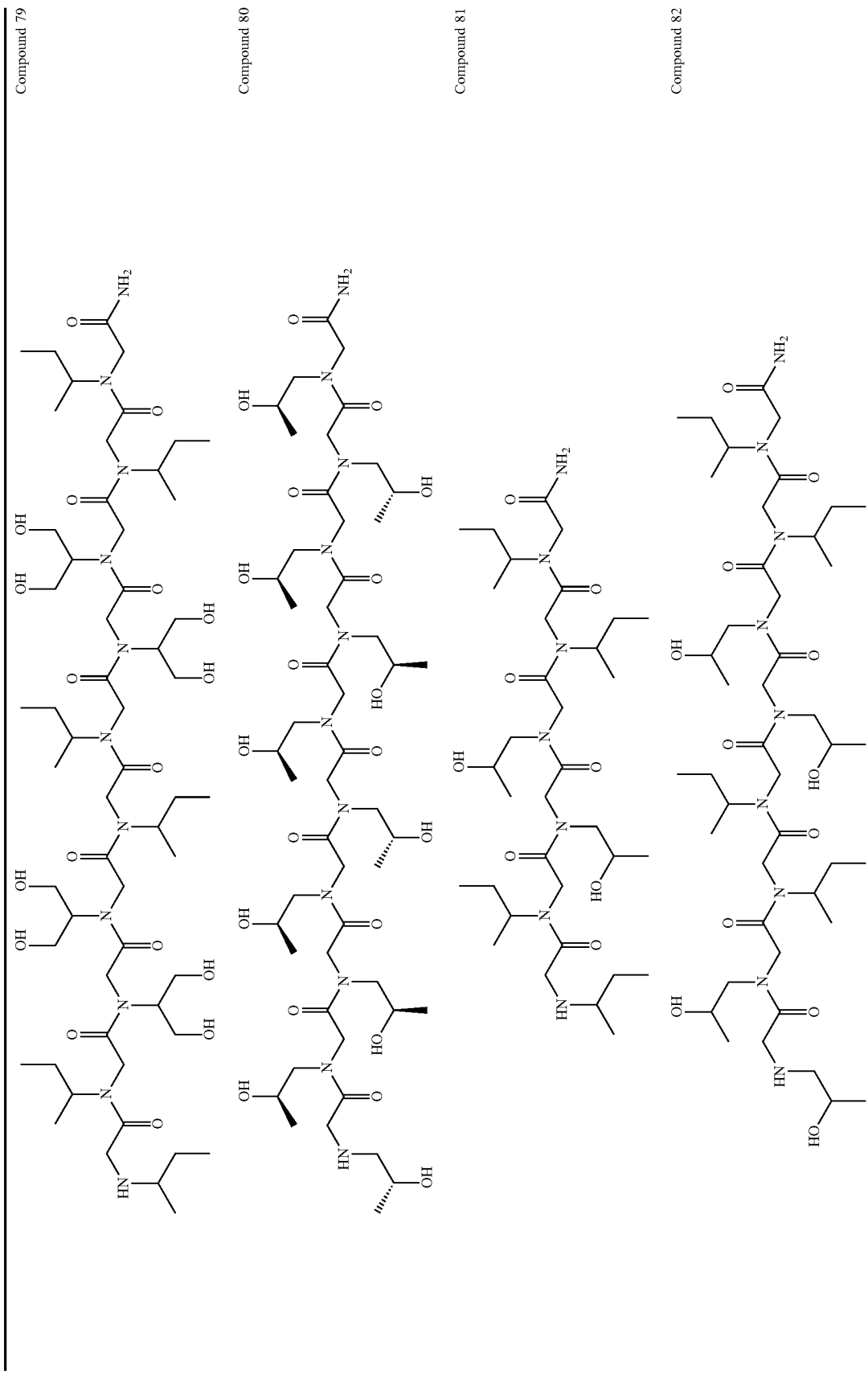

TABLE 10-continued
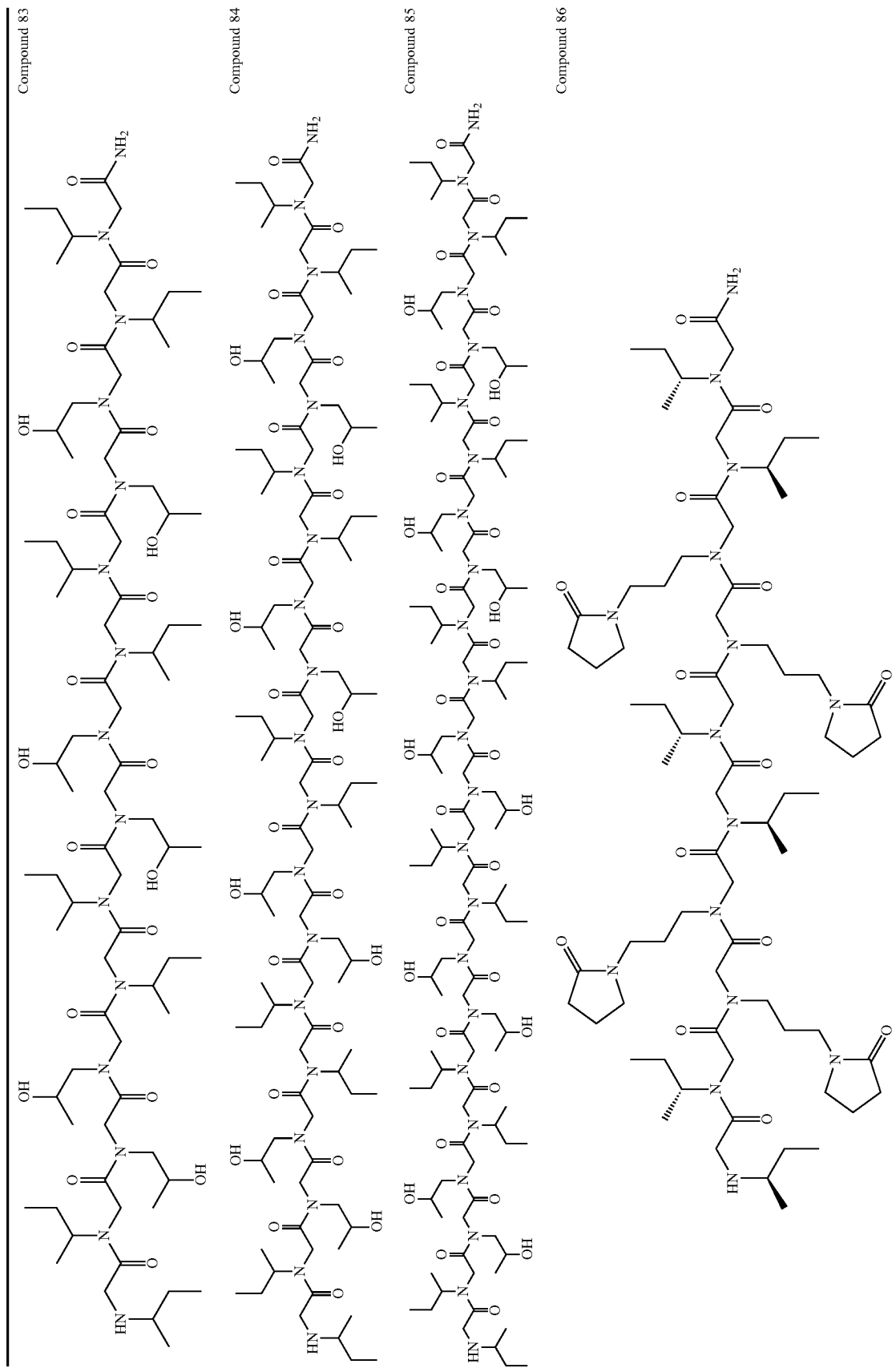

TABLE 10-continued
| Compound 87 | Compound 88 | Compound 89 |
|---|---|---|
| 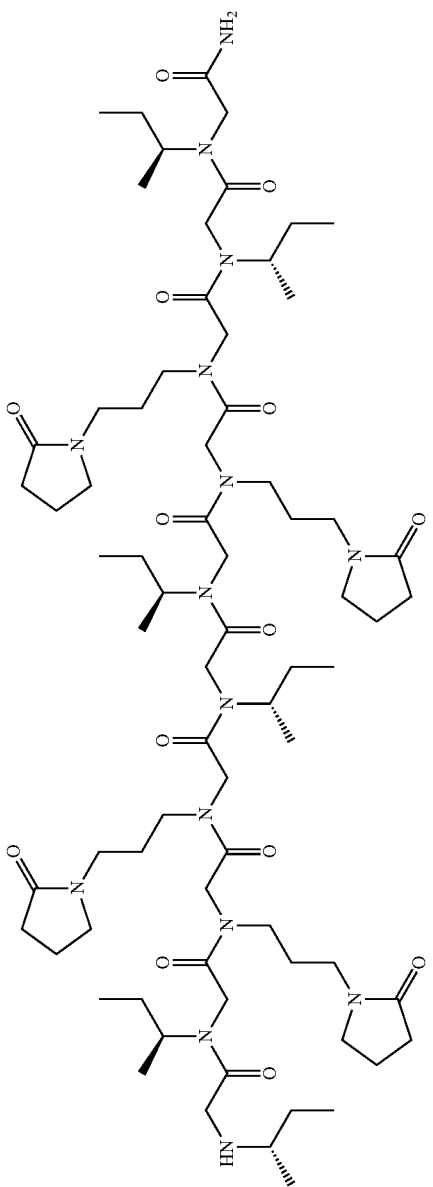 | 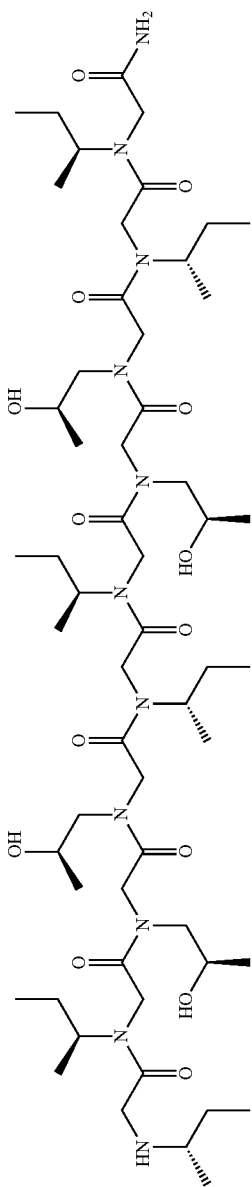 | 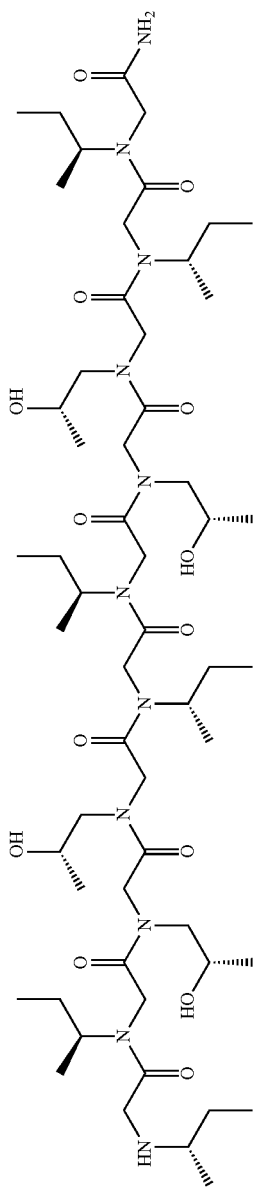 |

TABLE 10-continued
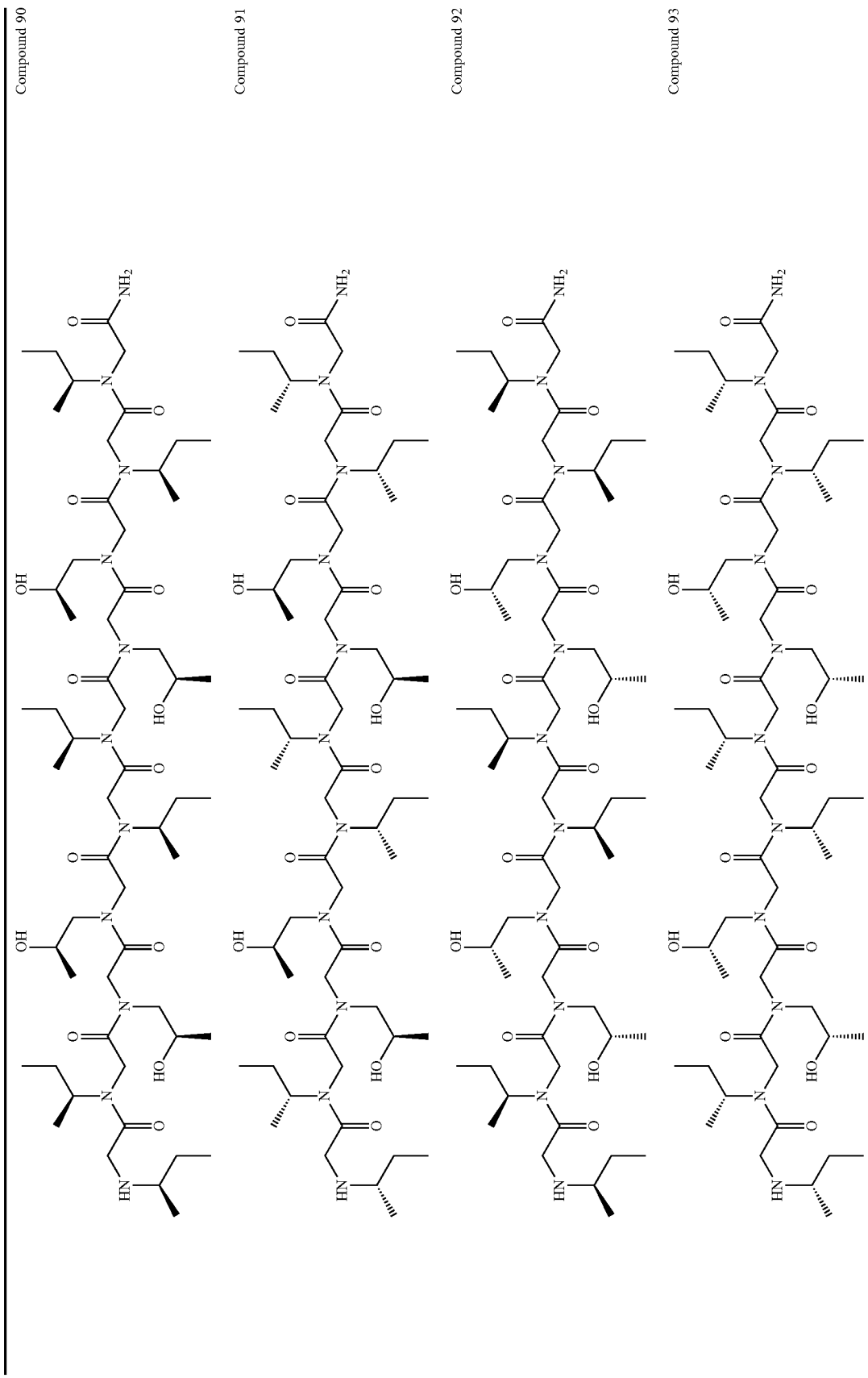

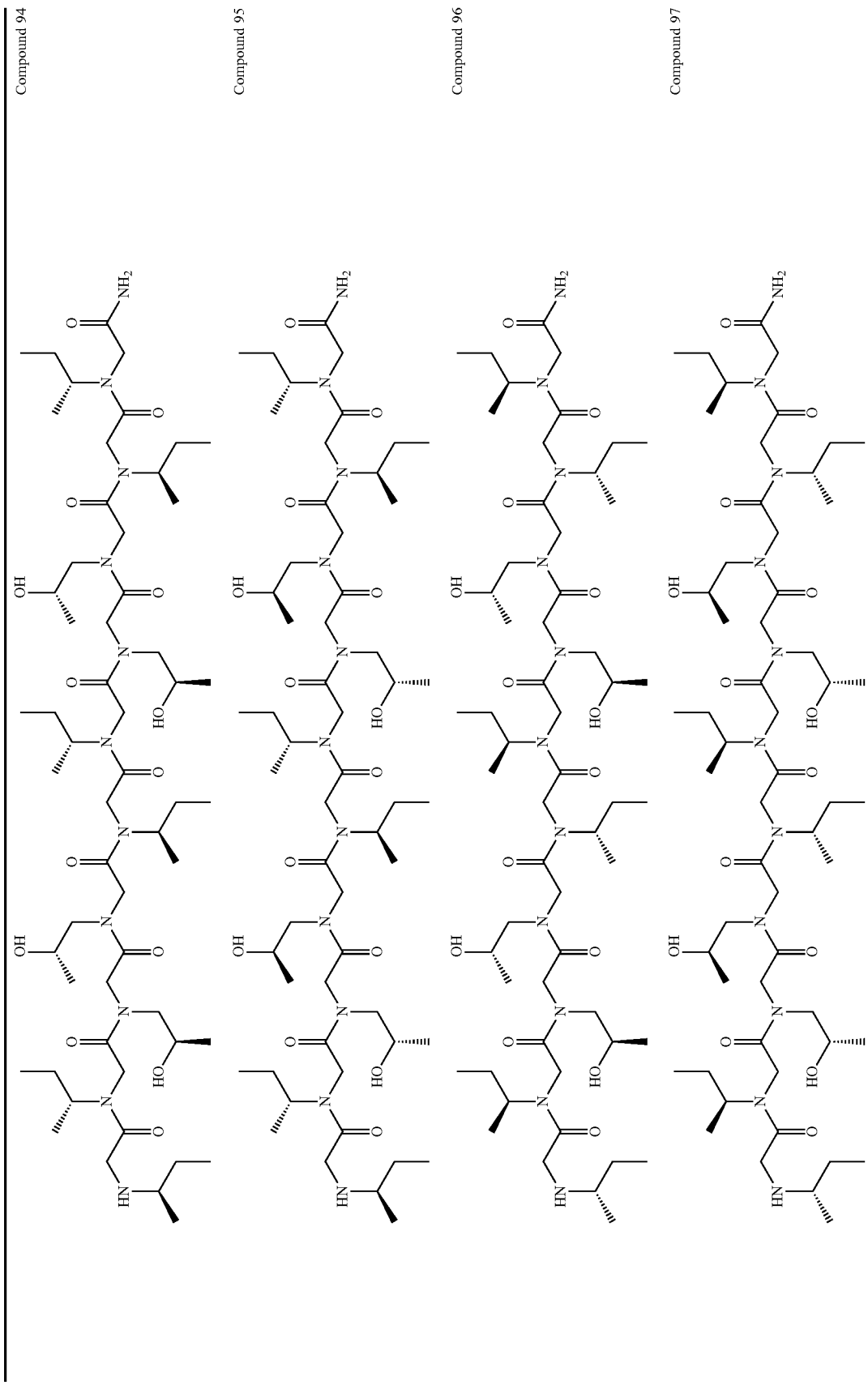

TABLE 10-continued
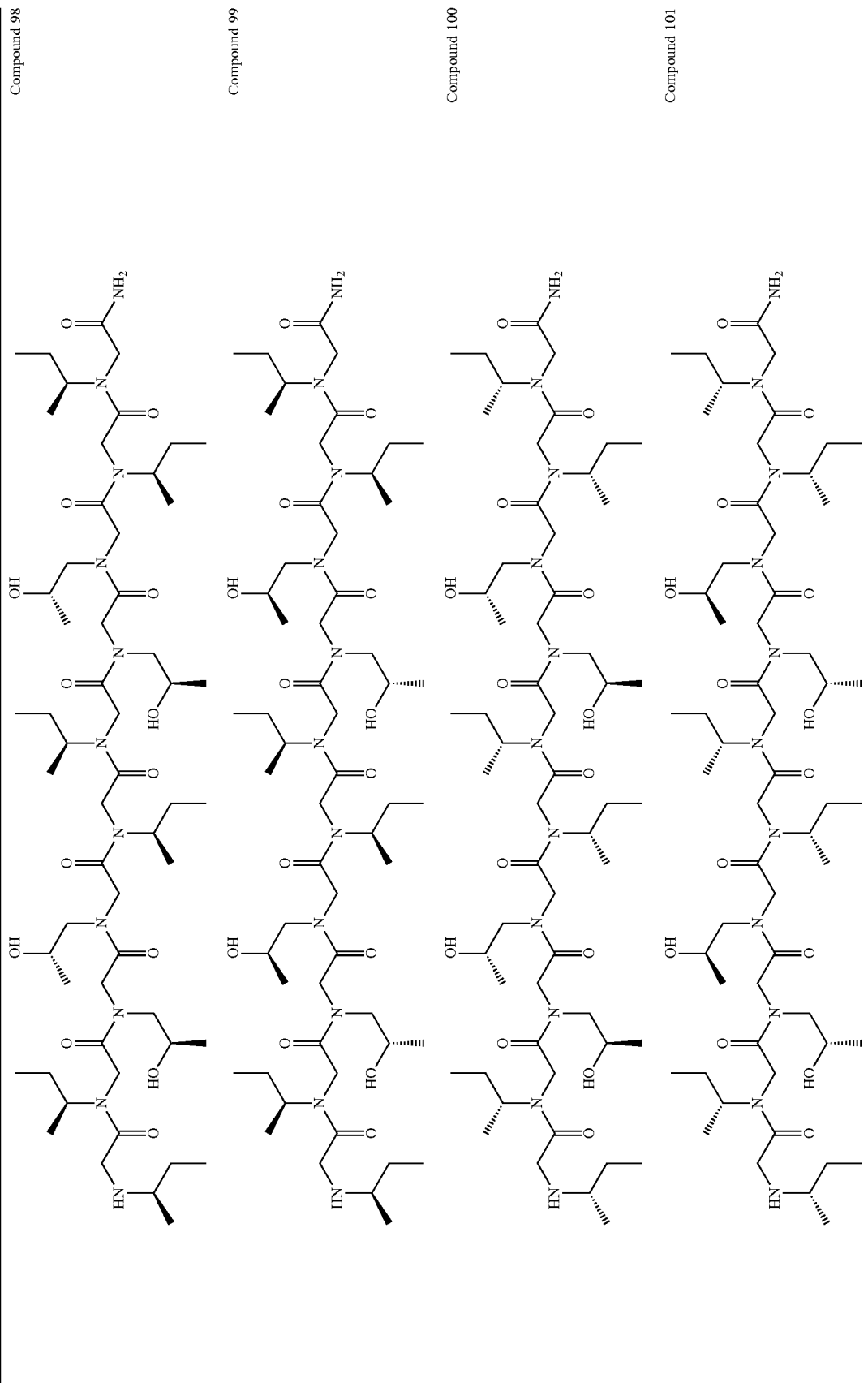

In some embodiments, the sequence length of the peptoid polymer, n, is 10, and the peptoid polymer comprises: 10 Nsb monomers, 1 Nhp monomer and 9 Nsb monomers, 2 Nhp monomers and 8 Nsb monomers, 3 Nhp monomers and 7 Nsb monomers, 4 Nhp monomers and 6 Nsb monomers, 5 Nhp monomers and 5 Nsb monomers, 6 Nhp monomers and 4 Nsb monomers, 7 Nhp monomers and 3 Nsb monomers, 8 Nhp monomers and 2 Nsb monomers, 9 Nhp monomers and 1 Nsb monomer, or 10 Nhp monomers.

In some embodiments, the peptoid polymer has the sequence Nhp-Nhp-Nhp-Nhp-Nhp-Nhp-Nhp-Nhp-Nhp-Nhp, wherein X is H or $C_{1-8}$ acyl and Y is —OH or —$NH_2$ or $C_{1-8}$alkyl. In some embodiments, the peptoid polymer has the sequence Nsb-Nsb-Nhp-Nsb-Nsb-Nhp-Nsb-Nsb-Nhp-Nsb, wherein X is H or $C_{1-8}$ acyl and Y is —OH or —$NH_2$ or $C_{1-8}$ alkyl. In some embodiments, the peptoid polymer has the sequence Nsb-Nhp-Nhp-Nhp-Nsb-Nhp-Nhp-Nhp-Nsb-Nhp, wherein X is H or $C_{1-8}$ acyl and Y is —OH or —$NH_2$ or $C_{1-8}$ alkyl. In some embodiments, the peptoid polymer has the sequence Nsb-Nsb-Nhp-Nhp-Nsb-Nsb-Nhp-Nhp-Nsb-Nsb, wherein X is H or $C_{1-8}$ acyl and Y is —OH or —$NH_2$ or $C_{1-8}$ alkyl. In some embodiments, the peptoid polymer has the sequence Nsb-Nhp-Nhp-Nhp-Nhp-Nhp-Nsb-Nhp-Nhp-Nhp, wherein X is H or $C_{1-8}$ acyl and Y is —OH or —$NH_2$ or $C_{1-8}$ alkyl. In some embodiments, Y is a secondary amine or a tertiary amine.

In some embodiments, the sequence length of the peptoid polymer, n, is 10, and the peptoid polymer comprises: 10 Nme monomers, 1 Nhp monomer and 9 Nme monomers, 2 Nhp monomers and 8 Nme monomers, 3 Nhp monomers and 7 Nme monomers, 4 Nhp monomers and 6 Nme monomers, 5 Nhp monomers and 5 Nme monomers, 6 Nhp monomers and 4 Nme monomers, 7 Nhp monomers and 3 Nme monomers, and 8 Nhp monomers and 2 Nme monomers, or 9 Nhp monomers and 1 Nme monomer.

In some embodiments, the sequence length of the peptoid polymer, n, is 10, and the peptoid polymer comprises: 1 Nhe monomers and 9 Nsb monomers, 2 Nhe monomers and 8 Nsb monomers, 3 Nhe monomers and 7 Nsb monomers, 4 Nhe monomers and 6 Nsb monomers, 5 Nhe monomers and 5 Nsb monomers, 6 Nhe monomers and 4 Nsb monomers, 7 Nhe monomers and 3 Nsb monomers, 8 Nhe monomers and 2 Nsb monomers, 9 Nhe monomers and 1 Nsb monomer, or 10 Nhe monomers.

In some embodiments, the sequence length of the peptoid polymer, n, is 10, and the peptoid polymer comprises: 10 Nbu monomers, 1 Nhp monomer and 9 Nbu monomers, 2 Nhp monomers and 8 Nbu monomers, 3 Nhp monomers and 7 Nbu monomers, 4 Nhp monomers and 6 Nbu monomers, 5 Nhp monomers and 5 Nbu monomers 6 Nhp monomers and 4 Nbu monomers, 7 Nhp monomers and 3 Nbu monomers, 8 Nhp monomers and 2 Nbu monomers, or 9 Nhp monomers and 1 Nbu monomer.

In some embodiments, the sequence length of the peptoid polymer, n, is 10, and the peptoid polymer comprises: 10 Nib monomers, 1 Nhp monomer and 9 Nib monomers, 2 Nhp monomers and 8 Nib monomers, 3 Nhp monomers and 7 Nib monomers, 4 Nhp monomers and 6 Nib monomers, 5 Nhp monomers and 5 Nib monomers, 6 Nhp monomers and 4 Nib monomers, 7 Nhp monomers and 3 Nib monomers, 8 Nhp monomers and 2 Nib monomers, or 9 Nhp monomers and 1 Nib monomer.

In some embodiments, the sequence length of the peptoid polymer, n, is 10, and the peptoid polymer comprises: 10 Npr monomers, 1 Nhp monomer and 9 Npr monomers, 2 Nhp monomers and 8 Npr monomers, 3 Nhp monomers and 7 Npr monomers, 4 Nhp monomers and 6 Npr monomers, 5 Nhp monomers and 5 Npr monomers, 6 Nhp monomers and 4 Npr monomers, 7 Nhp monomers and 3 Npr monomers, 8 Nhp monomers and 2 Npr monomers, or 9 Nhp monomers and 1 Npr monomer.

In some embodiments, the sequence length of the peptoid polymer, n, is 10, and the peptoid polymer comprises: 10 Nip monomers, 1 Nhp monomer and 9 Nip monomers, 2 Nhp monomers and 8 Nip monomers, 3 Nhp monomers and 7 Nip monomers, 4 Nhp monomers and 6 Nip monomers, 5 Nhp monomers and 5 Nip monomers, 6 Nhp monomers and 4 Nip monomers, 7 Nhp monomers and 3 Nip monomers, 8 Nhp monomers and 2 Nip monomers, or 9 Nhp monomers and 1 Nip monomer.

In some embodiments, the sequence length of the peptoid polymer, n, is 14, and the peptoid polymer comprises: 6 Nhp monomers and 8 Nsb monomers, 7 Nhp monomers and 7 Nsb monomers, 8 Nhp monomers and 6 Nsb monomers, 10 Nhp monomers and 4 Nsb monomers, or 14 Nhp monomers.

In some embodiments, the sequence length of the peptoid polymer, n, is 14, and the peptoid polymer comprises: 6 Nhp monomers and 8 Nib monomers, 7 Nhp monomers and 7 Nib monomers, 8 Nhp monomers and 6 Nib monomers, 10 Nhp monomers and 4 Nib monomers, or 14 Nhp monomers.

In some embodiments, the sequence length of the peptoid polymer, n, is 16, and the peptoid polymer comprises: 5 Nhp monomers and 11 Nsb monomers, 7 Nhp monomers and 9 Nsb monomers, 8 Nhp monomers and 8 Nsb monomers, 10 Nhp monomers and 6 Nsb monomers, 12 Nhp monomers and 4 Nsb monomers, or 16 Nhp monomers.

In some embodiments, the sequence length of the peptoid polymer, n, is 22, and the peptoid polymer comprises: 7 Nhp monomers and 15 Nsb monomers, 10 Nhp monomers and 12 Nsb monomers, 11 Nhp monomers and 11 Nsb monomers, 14 Nhp monomers and 8 Nsb monomers, 17 Nhp monomers and 5 Nsb monomers, or 22 Nhp monomers.

In other aspects, provided herein is a peptoid polymer comprising subunits comprising one or more first hydrophobic peptoid monomers H and one or more first polar peptoid monomers P arranged such that the peptoid polymer has the sequence $[H_aP_b]_n$ or $[P_bH_a]_n$, wherein the subscript a represents the number of consecutive first hydrophobic peptoid monomers within a subunit, the subscript b represents the number of consecutive first polar peptoid monomers within a subunit, and the subscript n represents the number of subunits within the peptoid polymer. In some embodiments, a is between 1 and 10 (e.g., a is 1, 2, 3, 4, 5, 6, 7, 8, 9, or 10). In other embodiments, b is between 1 and 10 (e.g., b is 1, 2, 3, 4, 5, 6, 7, 8, 9, or 10). In some instances, a is between 1 and 5. In other instances, b is between 1 and 5. In particular instances, a is between 1 and 3 and b is between 1 and 3.

In some embodiments, n is between 2 and 50 (e.g., n is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50). In some instances, n is between 2 and 10 (e.g., n is 2, 3, 4, 5, 6, 7, 8, 9, or 10). In some embodiments, n is between 3 and 25. In some embodiments, n is between 5 and 25. In some embodiments, n is between 8 and 50. In some embodiments, n is between 8 and 25. In some embodiments, n is between 8 and 20. In some embodiments, n can be between from about 10 to about 28, from about 12 to about 26, from about 14 to about 24, from about 16 to about 22, or from about 18 to about 20. In some embodiments, n can be between from about 8 to about 50, from about 8 to about 45, from about 8 to about 40, from about 8 to about 35, from about 8 to about 30, from about 10 to about 25, from about 10 to about 20, or from about 10 to about 15.

In some embodiments, the sequence length of the peptoid polymer is between 6 and 50. In some embodiments, the sequence length of the peptoid polymer is between 10 and 50. In some embodiments, the sequence length of the peptoid polymer is between 16 and 100. In some embodiments, the sequence length of the peptoid polymer is between 16 and 50. In some embodiments, the sequence length of the peptoid polymer is between 16 and 40. In some embodiments, the sequence length of the peptoid polymer can be between from about 20 to about 56, from about 24 to about 52, from about 28 to about 48, from about 32 to about 44, or from about 36 to about 40. In some embodiments, the sequence length of the peptoid polymer can be between from about 16 to about 100, from about 16 to about 90, from about 16 to about 80, from about 16 to about 70, from about 16 to about 60, from about 20 to about 50, from about 20 to about 40, or from about 20 to about 30. In some embodiments, the sequence length of the peptoid polymer can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more.

When more than one hydrophobic peptoid monomer is present in a peptoid polymer, all of the hydrophobic peptoid monomers can be the same, they can all be different, or a combination thereof. Similarly, when more than one polar peptoid monomer is present in a peptoid polymer, all of the polar peptoid monomers can be the same, they can all be different, or a combination thereof.

In some embodiments, the subunits further comprise a second hydrophobic peptoid monomer and/or a second polar peptoid monomer such that the peptoid polymer has the sequence $[H_aP_bH_cP_d]_n$ or $[P_bH_aP_dH_c]_n$, wherein the subscript c represents the number of consecutive second hydrophobic peptoid monomers within a subunit and the subscript d represents the number of consecutive second polar peptoid monomers within a subunit. In some embodiments, c is between 0 and 10 (e.g., c is 0, 1, 2, 3, 4, 5, 6, 7, 8, 9, or 10). In other embodiments, d is between 0 and 10 (e.g., d is 0, 1, 2, 3, 4, 5, 6, 7, 8, 9, or 10). In particular embodiments, both c and d are not 0. In some instances, c is between 0 and 5. In other instances, d is between 0 and 5.

As non-limiting examples, a subunit of a peptoid polymer of the present invention can comprise the sequence HP, PH, HHPP, PPHH, HPHP, PHPH, HPPH, PHHP, HHP, PHH, HPP, PPH, HPPP, PPPH, HHPPHH, PPHHPP, HHHPPP, PPPHHH, HHHP, PHHH, HHHPPPHHH, or PPPHHHPPP. When a is 1 and b is 1, the subunit can comprise the sequence HP or PH. When a is 2 and b is 2, the subunit can comprise the sequence HHPP or PPHH. When a is 1 and b is 2, the subunit can comprise the sequence HPP or PPH. When a is 2 and b is 1, the subunit can comprise the sequence HHP or PHH. When a is 1 and b is 3, the subunit can comprise the sequence HPPP or PPPH. When a is 3 and b is 1, the subunit can comprise the sequence HHHP or PHHH. When a is 3 and b is 3, the subunit can comprise the sequence HHHPPP or PPPHHH.

As further non-limiting examples, when a, b, c, and d are 1, the subunit can comprise the sequence HPHP or PHPH, although these sequences can also be represented by the formulas $[H_1P_1]_2$ and $[P_1H_1]_2$, respectively, where n is 2. When a is 1, b is 2, c is 1, and d is 0, the subunit can comprise the sequence HPPH. When a is 2, b is 1, c is 0, and d is 1 the subunit can comprise the sequence PHHP (i.e., $P_1H_2P_1H_0$). When a, b, and c are 2 and d is 0, the subunit can comprise the sequence HHPPHH. When a, b, and d are 2 and c is 0, the subunit can comprise the sequence PPHHPP (i.e., $P_2H_2P_2H_0$). When a, b, and c are 3 and d is 0, the subunit can comprise the sequence HHHPPPHHH. When a, b, and d are 3 and c is 0, the subunit can comprise the sequence PPPHHHPPP (i.e., $P_3H_3P_3H_0$).

In some embodiments, the peptoid polymer further comprises substituents X and Y such that the peptoid polymer has the sequence $X—[H_aP_b]_n—Y$, $X—[P_bH_a]_n—Y$, $X—[H_aP_bH_cP_d]_n—Y$, or $X—[P_bH_aP_dH_c]_n—Y$. X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen. In some embodiments, X is an acetyl group. In some embodiments, Y is carboxy. Alternatively, X and Y are taken together to form a covalent bond. The formation of a covalent bond between X and Y results in a circularized form of the peptoid polymer.

In some embodiments, X and Y are H, optionally substituted $C_{1-8}$ alkylamino, —OH, —SH, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen. In other embodiments, X or Y is a secondary amine or a tertiary amine.

In some embodiments, the peptoid polymer further comprises a sequence Z that comprises one or more hydrophobic peptoid monomers and/or one or more polar peptoid monomers. Z can be located before the first subunit, after the last subunit, and/or between one or more subunits. In some instances, Z comprises one or more hydrophobic peptoid monomers. In other instances, Z comprises one or more polar peptoid monomers. In particular instances, Z comprises one or more hydrophobic peptoid monomers and one or more polar peptoid monomers. Z can comprise a number of contiguous hydrophobic peptoid monomers followed by a number of contiguous polar peptoid monomers, or vice versa. Alternatively, Z can comprise a number of contiguous hydrophobic peptoid monomers followed by a number of contiguous polar peptoid monomers, followed by additional hydrophobic peptoid monomers, and so on. When more than one hydrophobic peptoid monomer is present in sequence Z, all of the hydrophobic peptoid monomers can be of the same type, they can each be different, or a combination thereof. Similarly, when more than one polar peptoid monomer is present in sequence Z, all of the polar peptoid monomers can be of the same type, they can each be different, or a combination thereof. In some embodiments, the peptoid polymer comprises more than 1 (e.g., 2, 3, 4, 5, or more) instances of a sequence Z. In such cases, all instances of Z can be the same, they can each be different, or a combination thereof. In particular embodiments, a sequence Z comprises 1, 2, 3, 4, or more hydrophobic peptoid monomers. In yet other embodiments, a sequence Z comprises 1, 2, 3, 4, or more polar peptoid monomers.

In other aspects, provided herein is a peptoid polymer comprising: (a) subunits comprising two first hydrophobic peptoid monomers H and two first polar peptoid monomers P, and (b) two second hydrophobic peptoid monomers located at the C-terminal end of the peptoid polymer, arranged such that the peptoid polymer has the sequence $[H_2P_2]_nH_2$ or $[P_2H_2]_nH_2$, wherein the subscript n, representing the number of subunits within the peptoid polymer, is between 1 and 50.

In still other aspects, provided herein is a peptoid polymer comprising: (a) subunits comprising two first hydrophobic peptoid monomers H and two first polar peptoid monomers P, and (b) two second polar peptoid monomers located at the C-terminal end of the peptoid polymer, arranged such that the peptoid polymer has the sequence $[H_2P_2]_nP_2$ or $[P_2H_2]_nP_2$, wherein the subscript n, representing the number of subunits within the peptoid polymer, is between 1 and 50.

In varying embodiments, all of the hydrophobic peptoid monomers can be the same, they can all be different, or a combination thereof. Similarly, all of the polar peptoid monomers can be the same, they can all be different, or a combination thereof.

In some embodiments, the peptoid polymer further comprises substituents X and Y such that the peptoid polymer has the sequence X—$[H_2P_2]_nH_2$—Y, X—$[P_2H_2]_nH_2$—Y, X—$[H_2P_2]_nP_2$—Y, or X—$[P_2H_2]_nP_2$—Y. In some embodiments, X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen. Alternatively, X and Y are taken together to form a covalent bond. The formation of a covalent bond between X and Y results in a circularized form of the peptoid polymer.

In some embodiments, X and Y are H, optionally substituted $C_{1-8}$ alkylamino, —OH, —SH, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen. In other embodiments, X or Y is a secondary amine or a tertiary amine.

In some embodiments, n is between 1 and 50 (e.g., n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50). In some instances, n is between 1 and 10 (e.g., n is 1, 2, 3, 4, 5, 6, 7, 8, 9, or 10). In some embodiments, n is between 1 and 25. In some embodiments, n is between 3 and 25. In some embodiments, n is between 5 and 25. In some embodiments, n is between 8 and 50. In some embodiments, n is between 8 and 25. In some embodiments, n is between 8 and 20. In some embodiments, n can be from about 10 to about 28, from about 12 to about 26, from about 14 to about 24, from about 16 to about 22, or from about 18 to about 20. In some embodiments, n can be from about 8 to about 50, from about 8 to about 45, from about 8 to about 40, from about 8 to about 35, from about 8 to about 30, from about 10 to about 25, from about 10 to about 20, or from about 10 to about 15.

In some embodiments, the peptoid polymer comprises Compound 62, Compound 63, Compound 67, Compound 73, Compound 76, Compound 86, or Compound 87 (i.e., when n is 2). In some instances, the peptoid polymer comprises Compound 76. In other embodiments, the peptoid polymer comprises Compound 81 (i.e., when n is 1).

In some embodiments, the peptoid polymer comprises one or more of the hydrophobic peptoid monomers selected from the group of monomers set forth in Table 1 above. In some embodiments, the peptoid polymer comprises one or more of the polar peptoid monomers selected from the group of monomers set forth in Table 1 above. In some embodiments, the peptoid polymer comprises one or more of the hydrophobic peptoid monomers and one or more of the polar peptoid monomers selected from the group of monomers set forth in Table 1 above.

In some embodiments, the first and/or second hydrophobic peptoid monomers are independently selected from the group consisting of

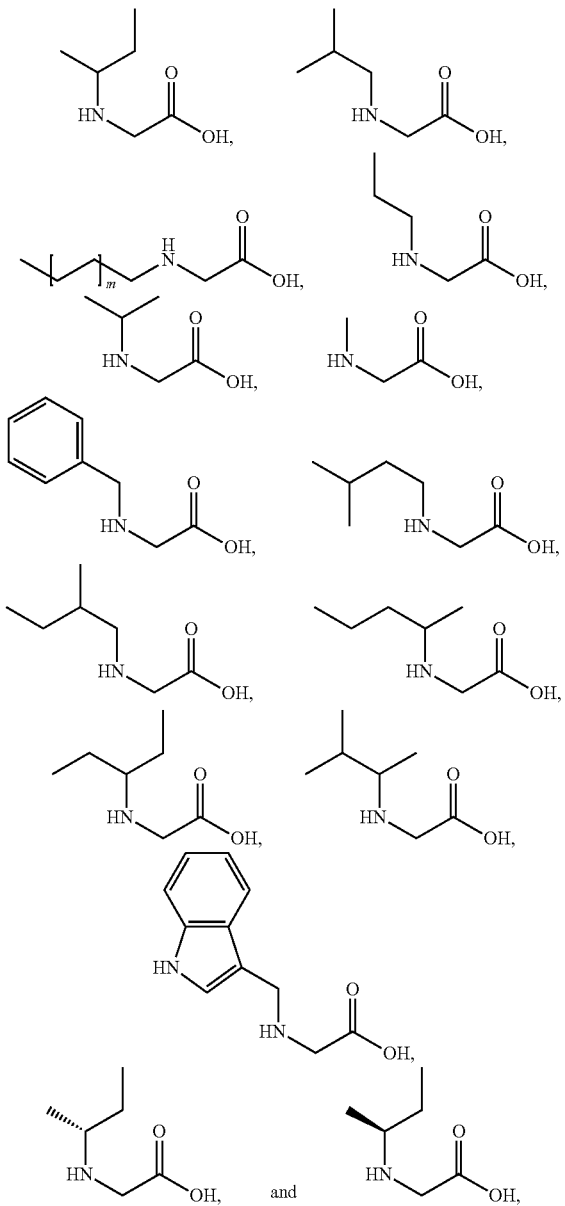

wherein the subscript m is the number of repeat units and is between 1 and 10 (e.g., m is 1, 2, 3, 4, 5, 6, 7, 8, 9, or 10). In some embodiments, the repeating unit, m, can be between 1 and 2, 1 and 3, 1 and 4, 1 and 5, 1 and 6, 1 and 7, 1 and 8, 1 and 9, or 1 and 10.

In some embodiments, at least 1, 2, 3, 4, 5, 6, 7, 8, 9, 10, 11, 12, 13, 14, 15, 16, 17, 18, 19, 20, or more hydrophobic peptoid monomers in the peptoid polymer have a side chain (e.g., $R^1$) that comprises an independently selected alkyl group wherein the alkyl group has 1, 2, 3, 4, 5, 6, 7, 8, 9, 10, 11, 12, 13, 14, 15, 16, 17, 18, or more carbon atoms. In particular embodiments, the alkyl group has 5 carbon atoms.

In some instances, the 5-carbon alkyl group is a pentyl group. In other instances, the 5-carbon alkyl group is a substituted butyl group (e.g., 1-methylbutyl, 2-methylbutyl, 3-methylbutyl, and the like). In yet other instances, the 5-carbon alkyl group is a substituted propyl group (e.g., 1-ethylpropyl, 1,2-dimethylpropyl, and the like).

In some embodiments, the first and/or second polar peptoid monomers are independently selected from the group consisting of

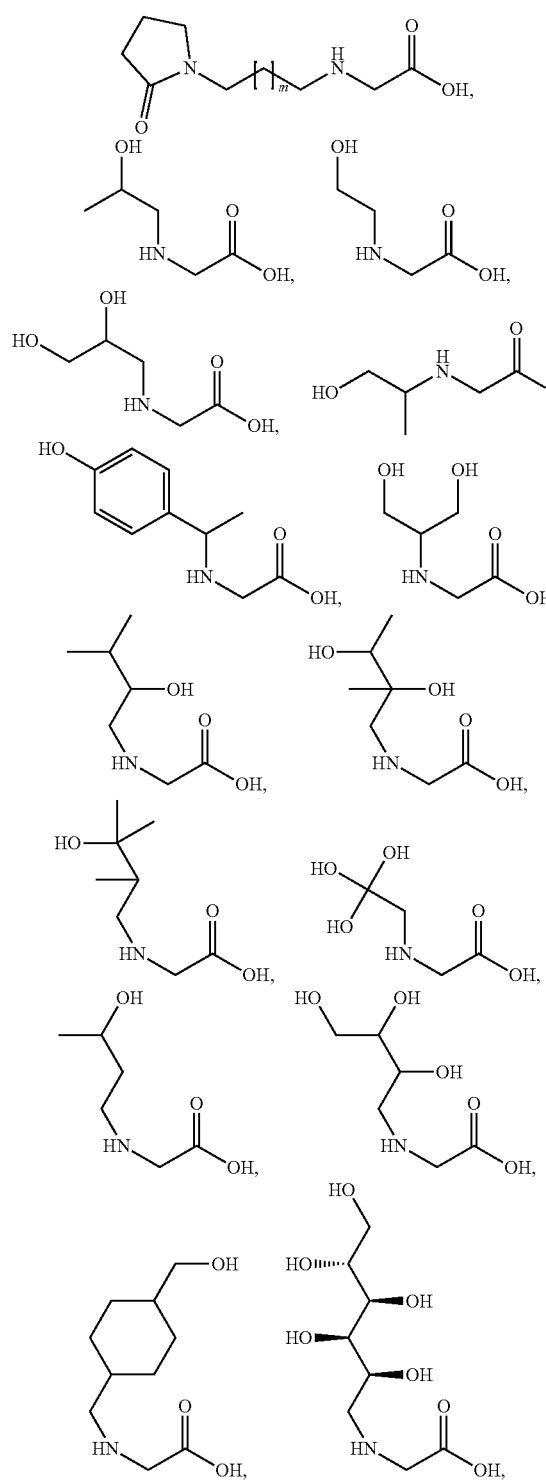
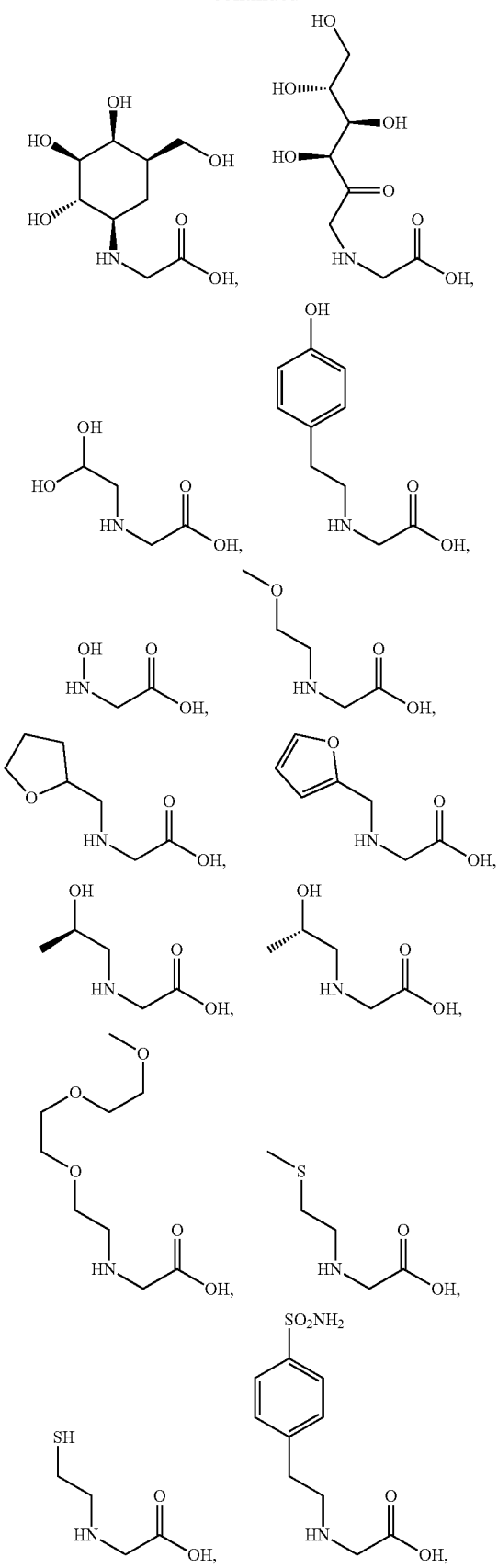

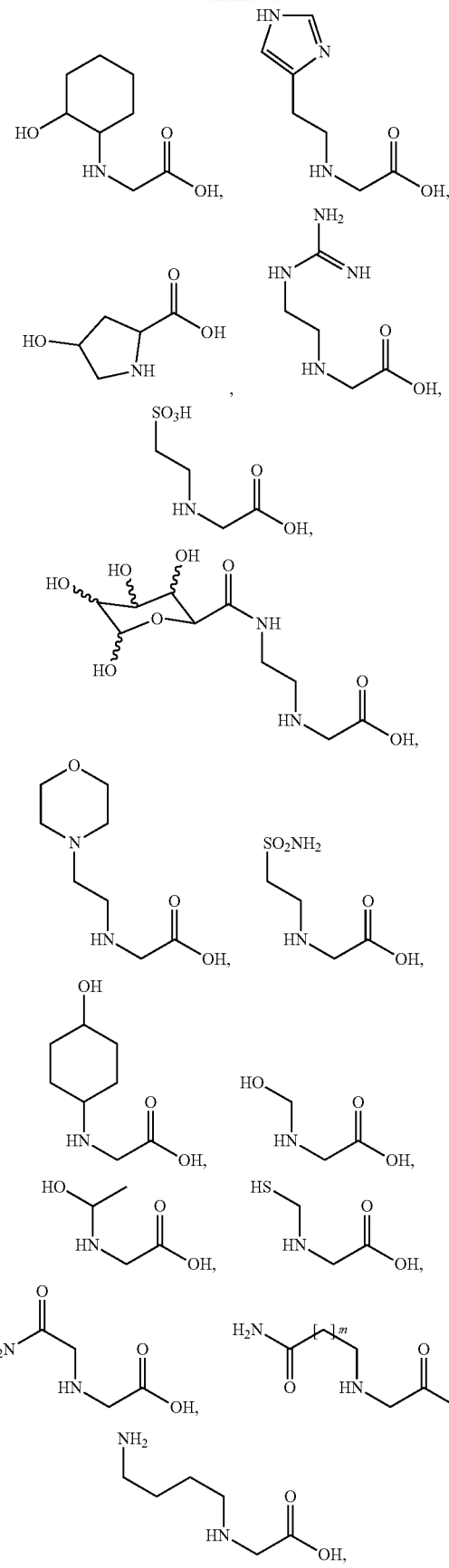

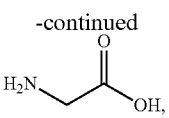

wherein the subscript m is the number of repeat units and is between 1 and 10 (e.g., m is 1, 2, 3, 4, 5, 6, 7, 8, 9, or 10). In some embodiments, the repeating unit, m, can be between 1 and 2, 1 and 3, 1 and 4, 1 and 5, 1 and 6, 1 and 7, 1 and 8, 1 and 9, or 1 and 10.

In some embodiments, the first and/or second polar peptoid monomer has a side chain (e.g., $R^1$) that comprises a hydroxyl group. In other embodiments, at least 1, 2, 3, 4, 5, 6, 7, 8, 9, 10, 11, 12, 13, 14, 15, 16, 17, 18, 19, 20, or more polar peptoid monomers in the peptoid polymer have a side chain (e.g., $R^1$) that comprises an independently selected $C_{1-18}$ hydroxyalkyl group (e.g., an independently selected $C_{1-6}$ hydroxyalkyl group). In some instances, each $C_{1-18}$ hydroxyalkyl group is a $C_{1-6}$ hydroxyalkyl group. In particular instances, each $C_{1-6}$ hydroxyalkyl group is the same $C_{1-6}$ hydroxyalkyl group. In some embodiments, at least 1, 2, 3, 4, 5, 6, 7, 8, 9, 10, 11, 12, 13, 14, 15, 16, 17, 18, 19, 20, or more polar peptoid monomers in the peptoid polymer have a side chain (e.g., $R^1$) that comprises an independently selected hydroxyalkyl group where the length of the alkyl in the hydroxyalkyl group is selected from 1, 2, 3, 4, 5, 6, 7, 8, 9, 10, 11, 12, 13, 14, 15, 16, 17, 18, or more carbon atoms. In particular embodiments, the hydroxyalkyl group contains 1, 2, 3, 4, 5, 6, 7, or 8 hydroxy substitutions.

In some embodiments, none of the polar peptoid monomers comprise a side chain (e.g., R') that comprises an optionally substituted $C_{1-18}$ hydroxyalkyl group.

In some embodiments, the side chain (e.g., $R^1$) of a polar peptoid monomer comprises a (4- to 10-membered heterocycloalkyl)($C_{1-6}$ alkylene) group or a (5- to 10-membered heteroaryl)($C_{1-6}$ alkylene) group. The alkylene moiety can be, for example, a straight-chain alkylene moiety such as methylene, ethylene, n-propylene (i.e., —CH$_2$CH$_2$CH$_2$—), or n-butylene (i.e., —CH$_2$CH$_2$CH$_2$CH$_2$—). The alkylene linker can also be branched, as in the case of sec-butylene (i.e., —CH(CH$_3$)CH$_2$CH$_2$—) or iso-butylene (i.e., —CH$_2$CH(CH$_3$)CH$_2$—). In some embodiments, the alkylene moiety is methylene (i.e., —CH$_2$—). In some embodiments, the alkylene moiety is n-propylene. In some embodiments, at least one member of the 4-, 5-, 6-, 7-, 8-, 9-, or 10-membered ring is O. In other embodiments, at least one member of the 4-, 5-, 6-, 7-, 8-, 9-, or 10-membered ring is N.

The heterocycloalkyl moiety can be, but is not limited to, a 4- to 8-membered ring, a 4- to 6-membered ring, or a 5- to 6-membered ring. The heterocycloalkyl moiety can be, for example, azetidinyl, pyrrolidinyl, piperidinyl, azepanyl, azocanyl, pyrazolidinyl, imidazolidinyl, piperazinyl, tetrahydrofuranyl, tetrahydropyranyl, oxepanyl, tetrahydrothiophenyl, tetrahydrothiopyranyl, oxazolidinyl, isoxazolidinyl, thiazolidinyl, isothiazolidinyl, or morpholinyl. In some embodiments, the heterocycloalkyl moiety is selected from pyrrolidin-1-yl, pyrrolidin-2-yl, pyrrolidin-3-yl, tetrahydrofuran-2-yl, and tetrahydrofuran-3-yl. In some embodiments, the heterocycloalkyl moiety is pyrrolidin-1-yl. In some embodiments, the heterocycloalkyl moiety is tetrahydrofuran-2-yl. In some embodiments, one or more carbon ring members in pyrrolidinyl or tetrahydrofuranyl is substituted with oxo.

In some embodiments, the peptoid polymer comprises

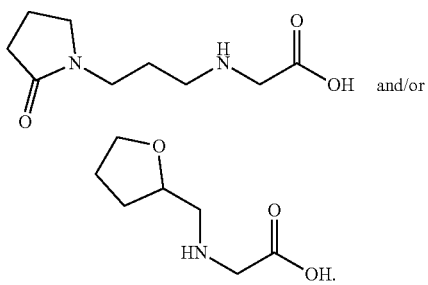

In some instances, the peptoid polymer comprises Compound 63, Compound 76, Compound 86, and/or Compound 87. In some embodiments, all of the polar peptoid monomers are

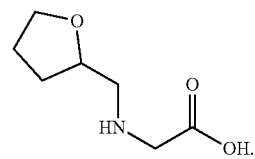 [SMILES: O=C(O)CNCC1CCCO1]

In other embodiments, all of the polar peptoid monomers are

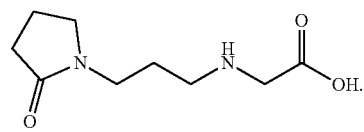 [SMILES: O=C(O)CNCCCN1CCCC1=O]

In some instances, the peptoid polymer is Compound 76, Compound 86, or Compound 87.

The heteroaryl moiety can be, but is not limited to, a 5- to 10-membered ring, a 5- to 9-membered ring, or a 5- to 6-membered ring. The heteroaryl moiety can be, for example, indolyl, quinolinyl, quinoxalinyl, quinazolinyl, phthalazinyl, cinnolinyl, benzofuranyl, pyrrolyl, pyridinyl, imidazolyl, pyrazolyl, pyrazinyl, pyrimidinyl, pyridazinyl, thiophenyl, or furanyl. In some embodiments, the heteroaryl moiety is selected from furan-2-yl, furan-3-yl, thiophen-2-yl, thiophen-3-yl, pyrrol-1-yl, pyrrol-2-yl, and pyrrol-3-yl.

In some embodiments, the side chain (e.g., $R^1$) comprises a (2-oxopyrrolidin-1-yl)($C_{1-4}$ alkylene) group. In some embodiments, the side chain (e.g., $R^1$) comprises a (tetrahydrofuran-2-yl)($C_{1-4}$ alkylene) group. In some embodiments, the side chain (e.g., $R^1$) comprises a (furan-2-yl)($C_{1-4}$ alkylene) group.

In some embodiments, the peptoid polymer comprises

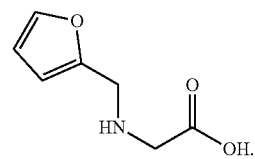 [SMILES: O=C(O)CNCc1ccco1]

In particular embodiments, all of the polar peptoid monomers are

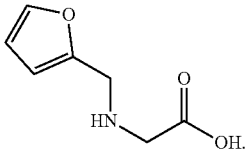

In some instances, the peptoid polymer is Compound 73.

In some embodiments, the side chain (e.g., R') of a polar peptoid monomer comprises a 2- to 20-membered alkoxy group. The side chain (e.g., R') can comprise, for example, a 2-12 membered alkoxy group having from 1-4 oxygen atoms, or 2-6 membered alkoxy having 1 or 2 oxygen atoms. In some embodiments, the side chain (e.g., R') comprises —CH$_2$CH$_2$OR', wherein R' is C$_{1-6}$ alkyl. In some embodiments, the side chain (e.g., R$^1$) comprises —CH$_2$CH$_2$O(CH$_2$CH$_2$O)$_n$R', wherein R' is C$_{1-6}$ alkyl and subscript n is 1, 2, or 3.

In some embodiments, the side chain (e.g., R') comprises a (C$_{1-6}$ alkoxy)(C$_{1-6}$ alkylene) group. In some embodiments, the side chain (e.g., R') comprises an (oligo[ethylene glycol]) or (oligo[propylene glycol]) group. In some embodiments, the side chain (e.g., R') comprises a methoxyethyl group. In some embodiments, the peptoid polymer comprises

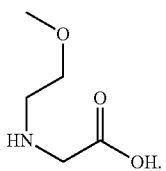

In particular embodiments, all of the polar peptoid monomers are

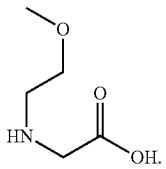

In some instances, the peptoid polymer is Compound 62.

In some embodiments, the oligo(ethylene glycol) moiety is a 2-(2-(2-methoxyethoxy)ethoxy)ethyl moiety. In some embodiments, the peptoid polymer comprises

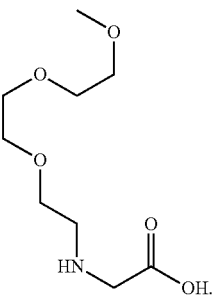

In particular embodiments, all of the polar peptoid monomers are

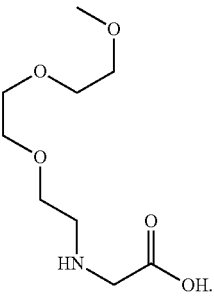

In some instances, the peptoid polymer is Compound 67.

In yet other aspects, provided herein is a peptoid polymer comprising one or more hydrophobic peptoid monomers and one or more polar peptoid monomers. In some embodiments, none of the polar peptoid monomers comprise a side chain (e.g., R$^1$) that comprises an optionally substituted C$_{1-18}$ hydroxyalkyl group. In some embodiments, the side chain (e.g., R$^1$) of a polar peptoid monomer comprises a (4- to 10-membered heterocycloalkyl)(C$_{1-6}$ alkylene) group. In other embodiments, the side chain (e.g., R$^1$) of a polar peptoid monomer comprises a (5- to 10-membered heteroaryl)(C$_{1-6}$ alkylene) group. In some embodiments, the side chain (e.g., R$^1$) of a polar peptoid monomer comprises a 2- to 20-membered alkoxy group. The side chain (e.g., R$^1$) can comprise, for example, 2-12 membered alkoxy having from 1-4 oxygen atoms, or 2-6 membered alkoxy having 1 or 2 oxygen atoms. In some embodiments, the side chain (e.g., R$^1$) comprises —CH$_2$CH$_2$OR', wherein R' is C$_{1-6}$ alkyl. In some embodiments, the side chain (e.g., R') comprises —CH$_2$CH$_2$O(CH$_2$CH$_2$O)$_n$R', wherein R' is C$_{1-6}$ alkyl and subscript n is 1, 2, or 3. In some embodiments, the side chain (e.g., R') of a polar peptoid monomer comprises a (C$_{1-6}$ alkoxy)(C$_{1-6}$ alkylene) group. In some embodiments, the side chain (e.g., R') of a polar peptoid monomer comprises an (oligo[ethylene glycol]) or (oligo[propylene glycol]) group.

The alkylene moiety can be, for example, a straight-chain alkylene moiety such as methylene, ethylene, n-propylene (i.e., —CH$_2$CH$_2$CH$_2$—), or n-butylene (i.e., —CH$_2$CH$_2$CH$_2$CH$_2$—). The alkylene linker can also be branched, as in the case of sec-butylene (i.e., —CH(CH$_3$)CH$_2$CH$_2$—) or iso-butylene (i.e., —CH$_2$CH(CH$_3$)CH$_2$—). In some embodiments, the alkylene moiety is methylene (i.e., —CH$_2$—). In some embodiments, the alkylene moiety is n-propylene. In some embodiments, at least one member of the 4-, 5-, 6-, 7-, 8-, 9-, or 10-membered ring is O. In other embodiments, at least one member of the 4-, 5-, 6-, 7-, 8-, 9-, or 10-membered ring is N.

The heterocycloalkyl moiety can be, but is not limited to, a 4- to 8-membered ring, a 4- to 6-membered ring, or a 5- to 6-membered ring. The heterocycloalkyl moiety can be, for example, azetidinyl, pyrrolidinyl, piperidinyl, azepanyl, azocanyl, pyrazolidinyl, imidazolidinyl, piperazinyl, tetrahydrofuranyl, tetrahydropyranyl, oxepanyl, tetrahydrothiophenyl, tetrahydrothiopyranyl, oxazolidinyl, isoxazolidinyl, thiazolidinyl, isothiazolidinyl, or morpholinyl. In some embodiments, the heterocycloalkyl moiety is selected from pyrrolidin-1-yl, pyrrolidin-2-yl, pyrrolidin-3-yl, tetrahydrofuran-2-yl, and tetrahydrofuran-3-yl. In some embodiments, the heterocycloalkyl moiety is pyrrolidin-1-yl. In some embodiments, the heterocycloalkyl moiety is tetrahydrofuran-2-yl. In some embodiments, one or more carbon ring members in pyrrolidinyl or tetrahydrofuranyl is substituted with oxo.

In some embodiments, the peptoid polymer comprises

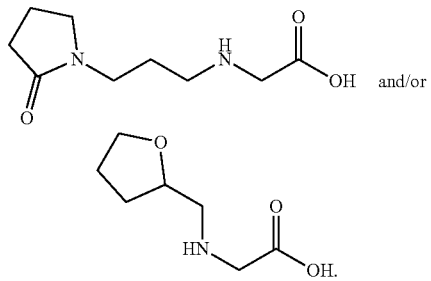 and/or

In some instances, the peptoid polymer comprises Compound 63, Compound 76, Compound 86, and/or Compound 87. In some embodiments, all of the polar peptoid monomers are

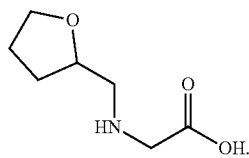 [SMILES: O=C(O)CNCC1CCCO1]

In other embodiments, all of the polar peptoid monomers are

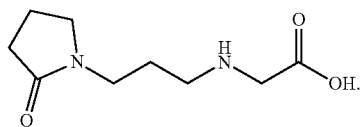 [SMILES: O=C(O)CNCCCN1CCCC1=O]

In some instances, the peptoid polymer is Compound 76, Compound 86, or Compound 87.

The heteroaryl moiety can be, but is not limited to, a 5- to 10-membered ring, a 5- to 9-membered ring, or a 5- to 6-membered ring. The heteroaryl moiety can be, for example, indolyl, quinolinyl, quinoxalinyl, quinazolinyl, phthalazinyl, cinnolinyl, benzofuranyl, pyrrolyl, pyridinyl, imidazolyl, pyrazolyl, pyrazinyl, pyrimidinyl, pyridazinyl, thiophenyl, or furanyl. In some embodiments, the heteroaryl moiety is selected from furan-2-yl, furan-3-yl, thiophen-2-yl, thiophen-3-yl, pyrrol-1-yl, pyrrol-2-yl, and pyrrol-3-yl.

In some embodiments, the side chain (e.g., $R^1$) comprises a (2-oxopyrrolidin-1-yl)($C_{1-4}$ alkylene) group. In some embodiments, the side chain (e.g., $R^1$) comprises a (tetrahydrofuran-2-yl)($C_{1-4}$ alkylene) group. In some embodiments, the side chain (e.g., $R^1$) comprises a (furan-2-yl)($C_{1-4}$ alkylene).

In some embodiments, the peptoid polymer comprises

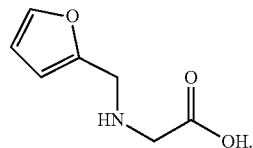 [SMILES: O=C(O)CNCc1ccco1]

In particular embodiments, all of the polar peptoid monomers are

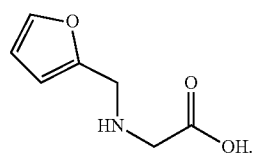 [SMILES: O=C(O)CNCc1ccco1]

In some instances, the peptoid polymer is Compound 73.

In some embodiments, the side chain (e.g., $R^1$) comprises a methoxyethyl group. In some embodiments, the peptoid polymer comprises

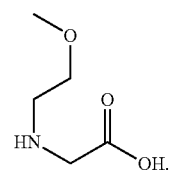

In particular embodiments, all of the polar peptoid monomers are

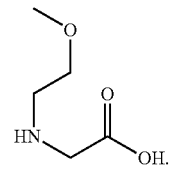

In some instances, the peptoid polymer is Compound 62.

In some embodiments, the oligo(ethylene glycol) moiety is a 2-(2-(2-methoxyethoxy)ethoxy)ethyl moiety. In some embodiments, the peptoid polymer comprises

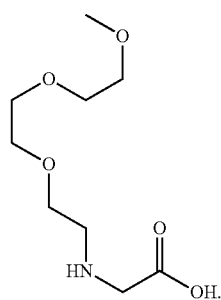

In particular embodiments, all of the polar peptoid monomers are

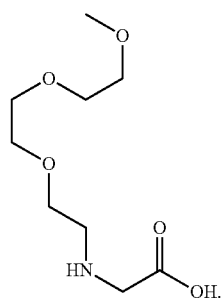

In some instances, the peptoid polymer is Compound 67.

In some embodiments, each of the one or more hydrophobic peptoid monomers are independently selected from the group consisting of

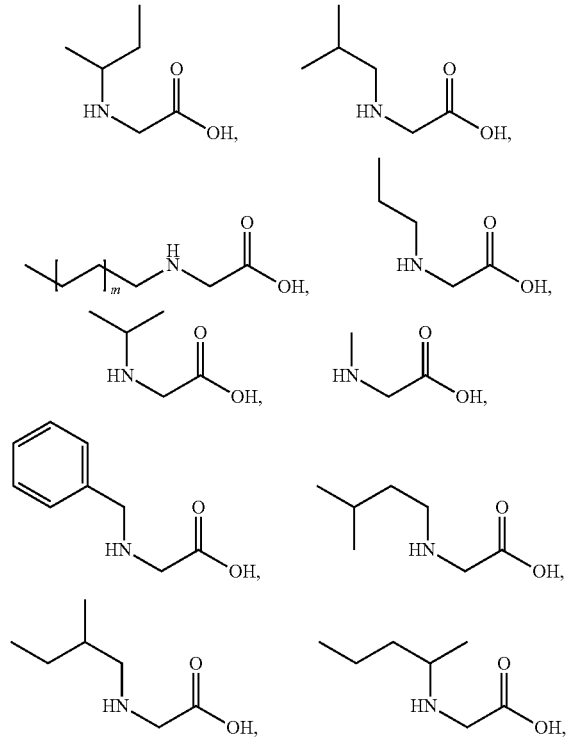

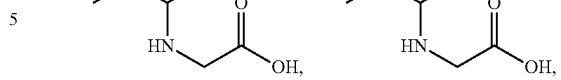

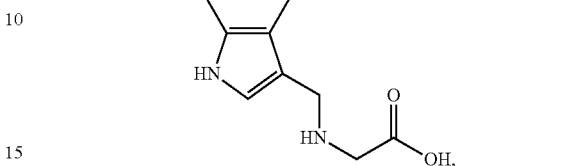

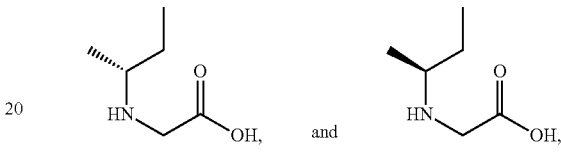

wherein the subscript m is the number of repeat units and is between 1 and 10.

In some embodiments, each of the one or more polar peptoid monomers are independently selected from the group consisting of

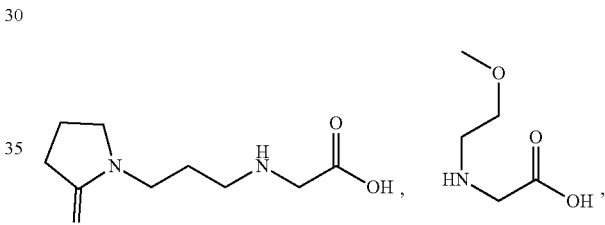

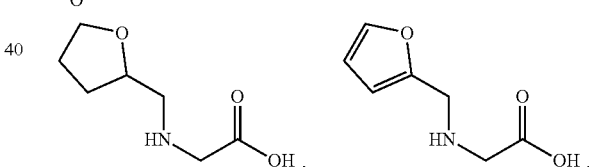

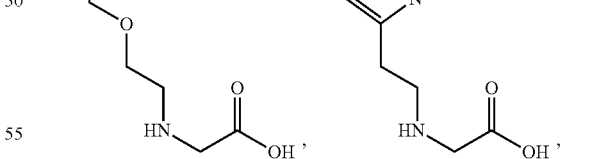

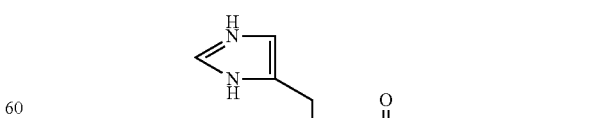

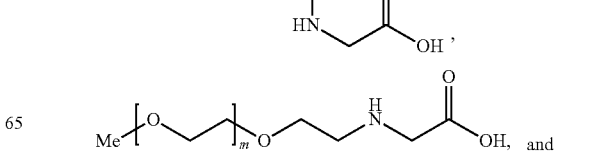

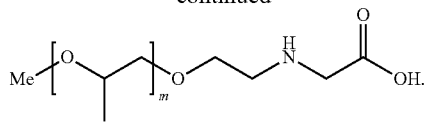

In some embodiments, the peptoid polymer further comprises substituents X and Y located at the N-terminal and C-terminal ends of the peptoid polymer, respectively. In some embodiments, X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen. Alternatively, X and Y are taken together to form a covalent bond. The formation of a covalent bond between X and Y results in a circularized form of the peptoid polymer.

In some embodiments, X and Y are H, optionally substituted $C_{1-8}$ alkylamino, —OH, —SH, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, or halogen. In other embodiments, X or Y is a secondary amine or a tertiary amine.

Whenever any peptoid monomer described herein does not indicate stereochemistry, any stereoisomer may be used. In some embodiments, a mixture of stereoisomers are chosen. Non-limiting examples of stereoisomers of hydrophobic peptoid monomers and polar peptoid monomers as well as exemplary ratios of R to S stereoisomers of the peptoid monomers in the peptoid polymers are described above.

In some embodiments, between about 1 percent and about 99 percent (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent) of the peptoid monomers in the peptoid polymer are hydrophobic peptoid monomers. In other embodiments, between about 1 percent and about 99 percent (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent) of the peptoid monomers in the peptoid polymer are polar peptoid monomers.

In some embodiments, about 5 percent of the peptoid monomers in the peptoid polymer are hydrophobic and about 95 percent of the peptoid monomers are polar.

In some embodiments, about 10 percent of the peptoid monomers in the peptoid polymer are hydrophobic and about 90 percent of the peptoid monomers are polar.

In some embodiments, about 15 percent of the peptoid monomers in the peptoid polymer are hydrophobic and about 85 percent of the peptoid monomers are polar.

In some embodiments, about 20 percent of the peptoid monomers in the peptoid polymer are hydrophobic and about 80 percent of the peptoid monomers are polar.

In some embodiments, about 25 percent of the peptoid monomers in the peptoid polymer are hydrophobic and about 75 percent of the peptoid monomers are polar.

In some embodiments, about 30 percent of the peptoid monomers in the peptoid polymer are hydrophobic and about 70 percent of the peptoid monomers are polar.

In some embodiments, about 35 percent of the peptoid monomers in the peptoid polymer are hydrophobic and about 65 percent of the peptoid monomers are polar.

In some embodiments, about 40 percent of the peptoid monomers in the peptoid polymer are hydrophobic and about 60 percent of the peptoid monomers are polar.

In some embodiments, about 45 percent of the peptoid monomers in the peptoid polymer are hydrophobic and about 55 percent of the peptoid monomers are polar.

In some embodiments, about 50 percent of the peptoid monomers in the peptoid polymer are hydrophobic and about 50 percent of the peptoid monomers are polar.

In some embodiments, about 55 percent of the peptoid monomers in the peptoid polymer are hydrophobic and about 45 percent of the peptoid monomers are polar.

In some embodiments, about 60 percent of the peptoid monomers in the peptoid polymer are hydrophobic and about 40 percent of the peptoid monomers are polar.

In some embodiments, about 65 percent of the peptoid monomers in the peptoid polymer are hydrophobic and about 35 percent of the peptoid monomers are polar.

In some embodiments, about 70 percent of the peptoid monomers in the peptoid polymer are hydrophobic and about 30 percent of the peptoid monomers are polar.

In some embodiments, about 75 percent of the peptoid monomers in the peptoid polymer are hydrophobic and about 25 percent of the peptoid monomers are polar.

In some embodiments, about 80 percent of the peptoid monomers in the peptoid polymer are hydrophobic and about 20 percent of the peptoid monomers are polar.

In some embodiments, about 85 percent of the peptoid monomers in the peptoid polymer are hydrophobic and about 15 percent of the peptoid monomers are polar.

In some embodiments, about 90 percent of the peptoid monomers in the peptoid polymer are hydrophobic and about 10 percent of the peptoid monomers are polar.

In some embodiments, about 95 percent of the peptoid monomers in the peptoid polymer are hydrophobic and about 5 percent of the peptoid monomers are polar.

In particular embodiments, the peptoid polymer comprises about 5, 10, 15, 20, 25, 30, 35, 40, 45, 50, 55, 60, 65, 70, 75, 80, 85, 90, or 95 percent hydrophobic peptoid monomers by mass. In other embodiments, the peptoid polymer comprises about 5, 10, 15, 20, 25, 30, 35, 40, 45, 50, 55, 60, 65, 70, 75, 80, 85, 90, or 95 percent polar peptoid monomers by mass.

In some embodiments, the peptoid polymer described herein forms a helical structure. In some embodiments, the helical structure adopts a structure analogous to a polyproline helix. In certain instances, the peptoid polymer forms a polyproline I helix. In certain other instances, the peptoid polymer forms a polyproline II helix. In some embodiments, a helical structure is adopted when the peptoid polymer comprises at least one N-Aryl side chain. In some embodiments, the N-Aryl side chain is a Nep monomer.

In some embodiments, the peptoid polymer reduces or inhibits ice crystal formation at a temperature within about 0° C. to about −20° C. In other embodiments, the peptoid polymer reduces or inhibits ice crystal formation at a temperature within about −10° C. to about −20° C. In certain embodiments, the peptoid polymer reduces or inhibits ice crystal formation at about −5° C., about −10° C., about −15° C., or about −20° C.

In some embodiments, the concentration of the peptoid polymer (e.g., present in a composition, formulation, or product such as a cryoprotectant solution) is between about 100 nM and about 1 M. In certain embodiments, the concentration of the peptoid polymer (e.g., present in a composition, formulation, or product such as a cryoprotectant solution) is between about 100 nM and about 250 nM, between about 250 nM and about 500 nM, between about 500 nM and about 750 nM, between about 750 nM and about 1 μM, between about 1 μM and about 5 μM, between about 5 μM and about 25 μM, between about 25 μM and about 50 μM, between about 50 μM and about 100 μM, between about 100 μM and about 250 μM, between about 250 μM and about 500 μM, between about 500 μM and about 750 μM, between about 750 μM and about 1 mM, between about 1 mM and about 10 mM, between about 10 mM and about 50 mM, between about 50 mM and about 100 mM, between about 100 mM and about 250 mM, between about 250 mM and about 500 mM, between about 500 mM and about 750 mM, or between about 750 mM and about 1 M. In some embodiments, the concentration of the peptoid polymer (e.g., present in a composition, formulation, or product such as a cryoprotectant solution) is between about 100 nM and about 100 mM. In other embodiments, the concentration of the peptoid polymer (e.g., present in a composition, formulation, or product such as a cryoprotectant solution) is about 100 nM, about 500 nM, about 1 μM, about 10 μM, about 100 μM, about 500 μM, about 1 mM, about 10 mM, about 100 mM, about 500 mM, or about 1 M. In particular embodiments, the concentration of the peptoid polymer is between about 1 and 100 mM (e.g., about 1, 2, 3, 4, 5, 6, 7, 8, 9, 10, 20, 30, 40, 50, 60, 70, 80, 90, or 100 mM).

B. Peptoid-Peptide Hybrids

In another aspect, the invention provides a peptoid-peptide hybrid. In some embodiments, the peptoid-peptide hybrid comprises a peptoid polymer described herein and one or more amino acids. The amino acids can be naturally-occurring amino acids or variants thereof. In some embodiments, the peptoid-peptide hybrid comprises between about 1 and 10 amino acids (e.g., about 1, 2, 3, 4, 5, 6, 7, 8, 9, or 10 amino acids). In other embodiments, the peptoid-peptide hybrid comprises between about 10 and 100 amino acids (e.g., about 10, 15, 20, 25, 30, 35, 40, 45, 50, 55, 60, 65, 70, 75, 80, 85, 90, 95, or 100 amino acids). In some embodiments, the peptoid-peptide hybrid comprises more than about 100 amino acids. In other embodiments, the peptoid-peptide hybrid comprises between 2 and 50 peptoid monomers (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 44, 45, 46, 47, 48, 49, or 50 peptoid monomers) and at least between about 1 and 100 amino acids (e.g., at least about 1, 2, 3, 4, 5, 6, 7, 8, 9, 10, 15, 20, 25, 30, 35, 40, 45, 50, 55, 60, 65, 70, 75, 80, 85, 90, 95, or 100 amino acids).

The amino acids can be located at any position within the polymer, including at the N- and C-terminal ends and/or in between any of the peptoid monomers or subunits. In instances where the peptoid-peptide hybrid comprises two or more amino acids, the amino acids may all be contiguous, or only a portion of them may be contiguous. Alternatively, all of the amino acids may be separated by one or more peptoid monomers or subunits.

In some embodiments, the amino acids are D-amino acids. In other embodiments, the amino acids are L-amino acids. In some other embodiments, the peptoid-peptide hybrid comprises a combination of D- and L-amino acids. In some embodiments, the one or more amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, tyrosine, and a combination thereof. In some instances, the one or more amino acids are selected from the group consisting of isoleucine, threonine, alanine, and a combination thereof.

In some embodiments, one or more Nsb peptoid monomers in a peptoid polymer are replaced with one or more isoleucine amino acid residues to create a peptoid-peptide hybrid. The one or more isoleucine amino acids can be D-amino acids, L-amino acids, or a combination thereof. In other embodiments, one or more Nhp peptoid monomers in a peptoid polymer are replaced with one or more threonine amino acid residues to create a peptoid-peptide hybrid. The one or more threonine amino acids can be D-amino acids, L-amino acids, or a combination thereof. In some other embodiments, one or more Nme peptoid monomers in a peptoid polymer are replaced with one or more alanine amino acid residues to create a peptoid-peptide hybrid. The one or more alanine amino acids can be D-amino acids, L-amino acids, or a combination thereof.

In some embodiments, the peptoid-peptide hybrid comprises the sequence:

Nep-Nep-Xaa-Xaa-Xaa-Xaa-Nep-Nep-Nep-Nep-Nme-Nme;

wherein the Xaa amino acid residues are independently selected amino acids such as D-amino acids, L-amino acids, or a combination thereof. As a non-limiting example, all instances of Xaa are Arg, Ala, Val, and/or Ser amino acid residues.

In other embodiments, the peptoid-peptide hybrid comprises the sequence:

Nme-Nme-Xaa-Nme-Nme-Nme-Nme-Nhp-Nhp-Nsb-Xaa-Nme-Nme-Xaa-Nme-Nme-Nme;

wherein the Xaa amino acid residues are independently selected amino acids such as D-amino acids, L-amino acids, or a combination thereof. As a non-limiting example, all instances of Xaa are Arg, Ala, Val, and/or Ile amino acid residues.

In yet other embodiments, the peptoid-peptide hybrid comprises the sequence:

Nme-Nme-Xaa-Nme-Nme-Nme-Nme-Nme-Nme-Nme-Xaa-Xaa;

wherein the Xaa amino acid residues are independently selected amino acids such as D-amino acids, L-amino acids, or a combination thereof. As a non-limiting example, all instances of Xaa are Arg, Ala, Val, and/or Leu amino acid residues.

In some embodiments, the peptoid-peptide hybrid comprises the sequence:

Arg-Nsb-Nsb-Nhp-Nhp-Nsb-Nsb-Nhp-Nhp-Nsb-Nsb;

wherein the Arg amino acid residue is a D-amino acid or an L-amino acid. In some embodiments, the peptoid-peptide hybrid comprises the structure set forth in Table 11.

TABLE 11

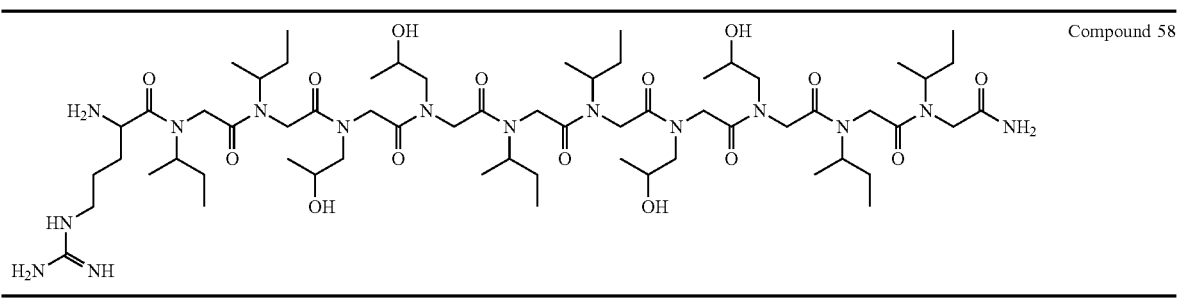

Compound 58

C. Methods of Synthesis

In another aspect, the invention herein provides a method of synthesizing a peptoid polymer or a peptoid-peptide hybrid. The peptoid polymers and peptoid-peptide hybrids of the invention can be prepared from readily available starting materials using the general methods and procedures described herein. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The peptoid polymers and peptoid-peptide hybrids of the invention may be prepared from known or commercially available starting materials and reagents by one skilled in the art of organic synthesis. Solvents and reagents are purchased from commercial sources and used without further purification.

In some embodiments, the submonomer approach (FIG. 1) is used for peptoid synthesis, where each N-substituted glycine monomer is assembled from two readily available "submonomers." The synthesis of oligomeric peptoids is based on the robust chemistry of standard solid-phase methods, analogous to peptide synthesis. Each cycle of monomer addition consists of two steps, an acylation step and a nucleophilic displacement step. In some embodiments, solid-phase assembly eliminates the need for N-protected monomers because there are no reactive side chain functionalities that need to be protected. One of skill in the art will recognize there are many solid-phase synthesis methods, including automated, robotic synthesizers. In some embodiments, the synthesizer used is the Symphony® X Multiplex Peptide Synthesizer made by Protein Technologies, Inc. In some embodiments, the synthesizer used is the Overture Peptide Synthesizer made by Protein Technologies, Inc. In other embodiments, the peptoids are synthesized manually using traditional organic chemistry methods known in the art. By providing the appropriate amino acids in place of peptoid monomers at the appropriate times during synthesis, the same techniques or techniques similar to those described above can be applied to the synthesis of peptoid-peptide oligomers.

As a non-limiting example, peptoid polymers can be synthesized on 100 mg of Rink amide resin (NovaBiochem; 0.49 mmol/g). Rink amide resin (100 mg) can be washed twice in 1.5 mL of DCM, followed by swelling in 1.5 mL of DMF. The swelling step can be performed twice. The Fmoc protecting group can be removed from the resin by addition of 20% piperidine/DMF. The mixture can be agitated for 10 minutes, drained, and the piperidine treatment repeated, followed by extensive washes with DMF (five times with 1.5 mL). The first monomer can be added manually by reacting 37 mg of bromoacetic acid (0.27 mmol; Sigma-Aldrich) and 189 μL of DIEA (1.08 mmol; Chem Impex International) in 2 mL of DCM on a shaker platform for 30 minutes at room temperature, followed by extensive washes with DCM (five times with 2 mL) and DMF (five times with 2 mL). Bromoacylated resin can be incubated with 2 mL of 1 M amine submonomer in DMF on a shaker platform for 30 minutes at room temperature, followed by extensive washes with DMF (five times with 2 mL). After initial manual loading of bromoacetic acid, the first submonomer displacement step and all subsequent bromo acetylation and amine displacement steps can be performed by a robotic synthesizer until the desired oligomer length is obtained. The automated bromoacetylation step can be performed by adding 1660 μL of 1.2 M bromoacetic acid in DMF and 400 μL of DIC (Chem Impex International). The mixture can be agitated for 20 min, drained, and washed with DMF (three times with 2 mL). Next, 2 mL of a 1 M solution of submonomer (2 mmol) in DMF can be added to introduce the side chain by nucleophilic displacement of bromide. The mixture can be agitated for 20 min, drained, washed with DMF (three times with 2 mL) and washed with DCM (three times with 2 mL). The peptoid-resin can be cleaved in 2 mL of 20% HFIP (Alfa Aesar) in DCM (v/v) at room temperature. The cleavage can be conducted in a glass tube with constant agitation for 30 minutes. HFIP/DCM can be evaporated under a stream of nitrogen gas. The final product can be dissolved in 5 mL of 50% ACN in HPLC grade $H_2O$ and filtered with a 0.5 pm stainless steel fritted syringe tip filter (Upchurch Scientific). Peptoid oligomers can be analyzed on a C18 reversed-phase analytical HPLC column at room temperature (Peeke Scientific, 5 μm, 120 Å, 2.0×50 mm) using a Beckman Coulter System Gold instrument. A linear gradient of 5-95% acetonitrile/water (0.1% TFA, Acros Organics) over 20 min can be used with a flow rate of 0.7 mL/min. In order to remove any traces of HFIP in the sample solution, linear precursors dissolved in 50% ACN/$H_2O$ can be freeze-dried overnight.

Peptoid polymers and peptoid-peptide hybrids can be analyzed by electrospray ionization (ESI) mass spectrometry. Generally, 0.5-2 mL of 1-5 μM of peptoid polymer or peptoid-peptide hybrid to be analyzed is prepared in a 50% deionized $H_2O$/50% HPLC grade ACN with 1% of an organic acid such as trifluoroacetic acid. Prepared samples are ionized by bombardment with electrons causing the molecules to break into charged fragments. The ions are then separated according to their mass-to-charge ratio by accelerating the fragments and exposing them to an electrical or magnetic field. The ions are detected by a mechanism capable of detecting charged particles, such as an electron multiplier. Peptoids and peptoid-peptide hybrids are identified by correlating masses to the identified masses or through a characteristic fragmentation pattern.

D. Methods of Use

In some aspects, the present invention provides a cryoprotectant solution. In some embodiments, the cryoprotectant solution comprises a peptoid polymer described herein, a peptoid-peptide hybrid described herein, or a combination thereof. In other embodiments, the cryoprotectant solution further comprises a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a nonionic surfactant, a protein, dimethyl sulfoxide (DMSO), polyethylene glycol (PEG), polypropylene glycol (PPG), Ficoll®, polyvinylpyrrolidone, polyvinyl alcohol, hyaluronan, formamide, a natural or synthetic hydrogel, and a combination thereof. In particular embodiments, the penetrating cryoprotectant penetrates the cell membrane and reduces the intracellular water concentration, thereby reducing the amount of ice formed at any temperature. In other particular embodiments, the non-penetrating cryoprotectant induces changes in colloidal osmotic pressure and modifies cell membrane associations with extracellular water by induced ionic interaction.

In some instances, the cryoprotectant solution further comprises an alcohol that is selected from the group consisting of propylene glycol, ethylene glycol, glycerol, methanol, butylene glycol, adonitol, ethanol, trimethylene glycol, diethylene glycol, polyethylene oxide, erythritol, sorbitol, xythyritol, polypropylene glycol, 2-methyl-2,4-pentanediol (MPD), mannitol, inositol, dithioritol, 1,2-propanediol, and a combination thereof.

In other instances, the cryoprotectant solution further comprises a sugar that is selected from the group consisting of a monosaccharide, a disaccharide, a polysaccharide, and a combination thereof. In particular instances, the sugar is selected from the group consisting of glucose, 3-O-Methyl-D-glucopyranose, galactose, arabinose, fructose, xylose, mannose, sucrose, trehalose, lactose, maltose, raffinose, dextran, and a combination thereof.

In other instances, the cryoprotectant solution further comprises PEG, PPG, or a plurality of different PEG or PPG compounds. In some other instances, at least one of the PEG or PPG compounds has an average molecular weight less than about 3,000 g/mol (e.g., less than about 3,000, 2,500, 2,000, 1,500, 1,000, 950, 900, 850, 800, 750, 700, 650, 600, 550, 500, 450, 400, 350, 300, 250, 200, 150, or 100 g/mol). In particular instances, at least one of the PEG or PPG compounds has an average molecular weight between about 200 and 400 g/mol (e.g., about 200, 210, 220, 230, 240, 250, 260, 270, 280, 290, 300, 310, 320, 330, 340, 350, 360, 370, 380, 390, or 400 g/mol). In some instances, the cryoprotectant solution comprises PEG or a plurality of PEG compounds selected from the group consisting of PEG 200, PEG 300, PEG 400, and a combination thereof.

In other instances, the cryoprotectant solution further comprises a protein that is selected from the group consisting of egg albumin, bovine serum albumin, human serum albumin, gelatin, and a combination thereof. In still other instances, the cryoprotectant solution further comprises a natural or synthetic hydrogel, wherein the natural or synthetic hydrogel comprises chitosan, hyaluronic acid, or a combination thereof.

Non-limiting examples of various properties of the cryoprotectant solution such as effective concentration, viscosity, water solubility, and/or membrane permeability can be assessed using a model cell or tissue including, but not limited to, genitourinary cells (e.g., corpus cavernosum cells such as smooth muscle corpus cavernosum cells and/or epithelial corpus cavernosum cells), stem cells, liver tissue or hepatocytes, kidney, intestine, heart, pancreas, bone marrow, organoids, and other biological tissues for cryopreservation.

In some embodiments, the cryoprotectant solution reduces or inhibits ice crystal formation at a temperature within about 0° C. to about −20° C. In other embodiments, the cryoprotectant solution reduces or inhibits ice crystal formation at a temperature within about −10° C. to about −20° C. In certain embodiments, the cryoprotectant solution reduces or inhibits ice crystal formation at about −5° C., about −10° C., about −15° C., or about −20° C.

In some embodiments, the concentration of the peptoid polymer and/or peptoid-peptide hybrid in the cryoprotectant solution is between about 100 nM and about 1 M. In some embodiments, the concentration of peptoid polymer and/or peptoid-peptide hybrid in the cryoprotectant solution is between about 100 nM and about 250 nM, between about 250 nM and about 500 nM, between about 500 nM and about 750 nM, between about 750 nM and about 1 μM, between about 1 μM and about 5 μM, between about 5 μM and about 25 μM, between about 25 μM and about 50 μM, between about 50 μM and about 100 μM, between about 100 μM and about 250 μM, between about 250 μM and about 500 μM, between about 500 μM and about 750 μM, between about 750 μM and about 1 mM, between about 1 mM and about 10 mM, between about 10 mM and about 50 mM, between about 50 mM and about 100 mM, between about 100 mM and about 250 mM, between about 250 mM and about 500 mM, between about 500 mM and about 750 mM, or between about 750 mM and about 1 M. In some embodiments, the concentration of the peptoid polymer and/or peptoid-peptide hybrid in the cryoprotectant solution is between about 100 nM and about 100 mM. In other embodiments, the concentration of the peptoid polymer and/or peptoid-peptide hybrid in the cryoprotectant solution is about 100 nM, about 500 nM, about 1 μM, about 10 μM, about 100 μM, about 500 μM, about 1 mM, about 10 mM, about 100 mM, about 500 mM, or about 1 M. In particular embodiments, the concentration of the peptoid polymer and/or peptoid-peptide hybrid in the cryoprotectant solution is between about 1 and 100 mM (e.g., about 1, 2, 3, 4, 5, 6, 7, 8, 9, 10, 20, 30, 40, 50, 60, 70, 80, 90, or 100 mM).

In other aspects, provided herein is a method for preserving a biological sample. In particular embodiments, the biological sample possesses cellular composition. In some embodiments, the biological sample is a cell. In some embodiments, the biological sample comprises primary cells. In other embodiments, the biological sample is a tissue or an organ. In particular embodiments, the biological sample comprises one or more cells, tissues, organs, or a combination thereof. In some embodiments, the method comprises contacting the biological sample with a peptoid polymer described herein, a peptoid-peptide hybrid described herein, a cryoprotectant solution described herein, or a combination thereof. In some instances, when a combination of compositions or solutions is used, contacting the biological sample with the compositions or solutions can be accomplished in multiple steps. As a non-limiting example, a biological sample can first be contacted with a peptoid polymer described herein, and then at a later point the biological sample can be contacted with a cryoprotectant solution described herein.

In particular instances, the tissue is a bioengineered tissue. In some instances, the biological sample is selected from the group consisting of heart, liver, lung, kidney, pancreas, intestine, thymus, cornea, nerve cells, blood platelets, sperm cells, oocytes, embryonic cells, stem cells, bone cells, and a combination thereof. In other instances, the biological sample comprises a population of cells (e.g., primary cells) selected from the group consisting of heart cells, liver cells, lung cells, kidney cells, pancreatic cells, gastric cells, intestinal cells, muscle cells, skin cells, neural cells, blood cells, immune cells, fibroblasts, genitourinary cells, bone cells, stem cells, sperm cells, oocytes, embryonic cells, epithelial cells, endothelial cells, and a combination thereof.

Cryoprotection of biological samples is useful for any number of purposes. Non-limiting examples include organoid preservation, stem cell preservation (e.g., hematopoietic stem cells, embryonic stem (ES) cells, pluripotent stem cells (PSCs), and induced pluripotent stem cells (iPSCs)), preservation of adult cells and cell lines (e.g., lymphocytes, granulocytes, immune system cells, bone cells), preservation of embryos, sperm, and oocytes, tissue preservation, and organ preservation. Preservation of tissues, organs, and other biological samples and structures is especially useful, for example, in the field of organ transplantation. Other useful applications of the present invention to biological sample cryoprotection will readily be known to one of skill in the art.

In yet other aspects, provided herein is a method for preserving one or more biological macromolecules. Said biological macromolecules can be naturally or unnaturally occurring. Non-limiting examples of biological macromolecules suitable for cryoprotection by the methods of the present invention include nucleic acids (e.g., DNA, RNA), amino acids, proteins, peptides, lipids, and composite structures (e.g., liposomes). In some embodiments, the method comprises contacting the biological macromolecule with a peptoid polymer described herein, a peptoid-peptide hybrid described herein, a cryoprotectant solution described herein, or a combination thereof. In some instances, the biological macromolecule is an isolated protein. In particular instances, the isolated protein is a protease protein. In some instances, when a combination of compositions or solutions is used, contacting the one or more biological macromolecules with the compositions or solutions can be accomplished in multiple steps. As a non-limiting example, the one or more biological macromolecules can first be contacted with a peptoid polymer described herein, and then at a later point the biological sample can be contacted with a cryoprotectant solution described herein.

Cryoprotection of biological macromolecules is useful for any number of purposes. Non-limiting examples of such purposes include the preservation of DNA (e.g., genomic DNA) and RNA samples, the preservation of stem cell growth factors, and the preservation of antibodies. Other useful purposes and applications of the present invention will be readily known by one of skill in the art.

Biological samples and macromolecules suitable for cryoprotection according to the present invention can come from any biological kingdom (e.g., Animalia (including but not limited to humans and livestock animals), Plantae, Fungi (including but not limited to mushrooms), Protista, Archaea/Archaeabacteria, and Bacteria/Eubacteria).

E. Cryopreservation Protocols

The methods described herein are useful for cryopreservation during supercooling to high sub-zero temperatures (e.g., 0° C. to −20° C.). In the field of organ transplantation, organs are typically cooled on ice (e.g., to 0° C. to 4° C.), which limits the transplantation window to about ten hours. By using ex vivo machine perfusion with cryoprotectants containing standard small molecule CPAs, it has been possible to preserve organs for up to 96 hours at a temperature of −6° C. While it is desirable to further reduce the cryopreservation temperature below −6° C., which would extend the possible cryopreservation time, it has not been possible to do so because the high concentrations of standard CPAs necessary to further reduce the temperature result in irreversible organ damage owing to CPA-related toxicity. For more information, see, e.g., Uygun K, et. al. *Nat. Protoc.* 10(3):484-94 (2015). Employing ex vivo perfusion methods or otherwise contacting biological samples (e.g., organs and tissues) or macromolecules with peptoid polymers, peptoid-peptide hybrids, and/or cryoprotectant solutions described herein is useful for supercooling to high sub-zero temperatures, allowing cryopreservation for longer periods of time and at lower temperatures than is currently feasible. Other suitable applications of the present invention to high sub-zero temperature supercooling will readily be known to one of skill in the art.

One of skill in the art will readily appreciate that the concentrations and compositions of the peptoid polymers, peptoid-peptide hybrids, and cryoprotectant solutions described herein can be modified depending on the particular biological sample and/or macromolecule being cryopreserved and the particular cryopreservation protocol being employed.

F. Methods of Screening

In a related aspect, provided herein are methods for screening peptoid polymers, peptoid-peptide hybrids, and/or cryoprotectant solutions for activity.

In one embodiment, the peptoid polymer, peptoid-peptide hybrid, and/or cryoprotectant solution is screened for lowering the freezing point of water using a polarized light microscope to detect ice crystal formation. Polarized light microscopy is an optical microscopy technique that uses polarized light as the light source. Image contrast arises from the interaction of plane-polarized light with a birefringent (or doubly-refracting) species to produce two individual wave components that are each polarized in mutually perpendicular planes. The velocities of these components, which are termed the ordinary and the extraordinary wavefronts, are different and vary with the propagation direction through the specimen. After exiting the specimen, the light components become out of phase, but are recombined with constructive and destructive interference when they pass through the analyzer. This interference creates a detectable contrast in the sample. Ice crystal formation is easily detected using this technique because ice crystals are birefringent species. In a standard experiment, samples comprising the peptoid polymer, peptoid-peptide hybrid, and/or cryoprotectant solution are cooled to a desired temperature for a desired amount of time. One or more samples, while at the desired temperature, are placed under the polarized light microscope and visually inspected for formation of ice crystals.

In one embodiment, the peptoid polymer, peptoid-peptide hybrid, and/or cryoprotectant solution is screened for lowering the freezing point of an aqueous solution using differential scanning calorimetry to quantitate thermal hysteresis activity. Differential scanning calorimetry is a thermoanalytical technique in which the difference in the amount of heat required to increase the temperature of a sample and reference is measured as a function of temperature. When a physical transformation such as phase transition occurs, more or less heat will need to flow to the sample than the reference to maintain both at the same temperature. The difference in temperature between the phase transition of the reference and the sample reports on the sample's ability to reduce or inhibit ice crystal formation at sub 0° C. temperatures. In a standard experiment, a sample comprising the peptoid polymer, peptoid-peptide hybrid, and/or cryoprotectant solution is compared to a reference that lacks the peptoid polymer, peptoid-peptide hybrid, and/or cryoprotectant solution.

G. Cell Viability Assays to Test for Activity

In a related aspect, provided herein are cell viability assays to test for the ability of the peptoid polymer, peptoid-peptide hybrid, and/or cryoprotectant solution to maintain cell viability (e.g., after storage) at reduced temperatures.

In some embodiments, cell viability is tested using the alamarBlue® Cell Viability Assay Protocol provided by Thermo Fisher Scientific, Inc. Briefly, alamarBlue® is the trade name of resazurin (7-Hydroxy-3H-phenoxazin-3-one 10-oxide) which is a non-toxic cell permeable compound that is blue in color and virtually non-fluorescent. Upon entering cells, resazurin is reduced to resorufin, a compound that is red in color and highly fluorescent. Viable cells continuously convert resazurin to resorufin, increasing the overall fluorescence and color of the media surrounding cells. Non-viable cells do not convert resazurin to resorufin, thus the overall fluorescence and color of the media surrounding the cells is an indication of the relative amount of viable cells in the sample. In a standard experiment, cells and the peptoid polymer, peptoid-peptide hybrid, and/or cryoprotectant solution are mixed in any suitable container. The mixture is then cooled to the desired sub 0° C. temperature and held for the desired amount of time. Cells are then returned to ambient temperatures and the almarBlue® reagent is added, incubated, and measured following the Thermo Fisher protocol. Typically, direct readout of cell viability is determined by measuring the relative fluorescence of the samples at the wavelengths $\lambda_{Ex}$~560 nm/$\lambda_{Em}$~590 nm.

In some embodiments, cell viability is tested using the LIVE/DEAD® Viability/Cytotoxicity Kit, for mammal cells provided by Thermo Fisher Scientific, Inc. This kit uses two indicator molecules: calcein AM and Ethidium homodoimer-1 (EthD-1). Live cells are distinguished by the presence of ubiquitous intracellular esterase activity, determined by the enzymatic conversion of the virtually nonfluorescent cell-permeant calcein AM to the intensely fluorescent calcein. The polyanionic dye calcein is well retained within live cells, producing an intense uniform green fluorescence in live cells ($\lambda_{Ex}$~495 nm/$\lambda_{Ex}$~515 nm). Conversely, EthD-1 enters cells with damaged membranes and undergoes a 40-fold enhancement of fluorescence upon binding to nucleic acids, thereby producing a bright red fluorescence in dead cells ($\lambda_{Ex}$~495 nm/$\lambda_{Em}$~635 nm). Notably, EthD-1 is excluded by the intact plasma membrane of live cells, so the determination of live and dead cells is easily distinguishable. Calcein and EthD-1 can be viewed simultaneously with a conventional fluorescein longpass filter. Alternatively, the fluorescence from these dyes may also be observed separately; calcein can be viewed with a standard fluorescein bandpass filter, and EthD-1 can be viewed with filters for propidium iodide or Texas Red® dye. In a standard experiment, cells and the peptoid polymer, peptoid-peptide hybrid, and/or cryoprotectant solution are mixed in any suitable container. The mixture is then cooled to the desired sub 0° C. temperature, held at that temperature for the desired amount of time, and then returned to ambient temperatures. Subsequent steps involving the addition of the calcein AM and EthD-1 reagents and measuring the assay results are performed as described in the Thermo Fisher protocol. Typically, direct readout of cell viability is determined by measuring the relative fluorescence at the above indicated wavelengths for both reagents.

In some embodiments, cell viability is tested using the MTT assay. The MTT assay is a colorimetric cell viability and proliferation assay that relies upon the reduction of yellow tetrazolium MTT (3-(4,5-dimethylthiazolyl-2)-2,5-diphenyltetrazolium bromide) to the insoluble formazan, which has a purple color. Tetrazolium dye reduction is dependent on NAD(P)H-dependent oxidoreductase enzymes, primarily located in the cytosolic compartment of metabolically active cells. The MTT assay is available, for example, from ATCC (www.atcc.org) or Sigma-Aldrich (www.sigmaaldrich.com). In a standard experiment, cells and the peptoid polymer, peptoid-peptide hybrid, and/or cryoprotectant solution are mixed in any suitable container. The mixture is then cooled to the desired sub 0° C. temperature and held for the desired amount of time. Cells are then returned to ambient temperatures and the MTT reagent is added, incubated, and measured following the ATCC or Sigma-Aldrich protocol. Typically, absorbance of converted dye is measured at a wavelength of 570 nm with background subtraction at 630-690 nm.

IV. Examples

The following examples are offered to illustrate, but not to limit, the claimed invention.

Example 1. Peptoid-Mediated Inhibition of Ice Crystal Formation

This example illustrates the ice crystal inhibition properties of N-substituted peptoid polymers and peptoid-peptide hybrids at sub 0° C. temperatures.

Capillary Tube Assays

In this experiment, four water-based samples were prepared in capillary tubes containing MilliQ purified water. One sample contained only water, and another sample contained 160 mM ethylene glycol (EG). The other two samples each contained a peptoid polymer at 9 mM. One of the peptoid polymer samples contained the peptoid polymer called "Compound 1," while the other sample contained the peptoid polymer called "Compound 10." The sequences of the peptoid polymers are as follows:

```
Compound 1:
Nsb-Nsb-Nhp-Nsb-Nsb-Nhp-Nsb-Nsb-Nhp-Nsb;

Compound 10:
Nhp-Nhp-Nhp-Nhp-Nhp-Nhp-Nhp-Nhp-Nhp-Nhp.
```

The chemical structures for these compounds are provided in Table 2.

Figure 2A:
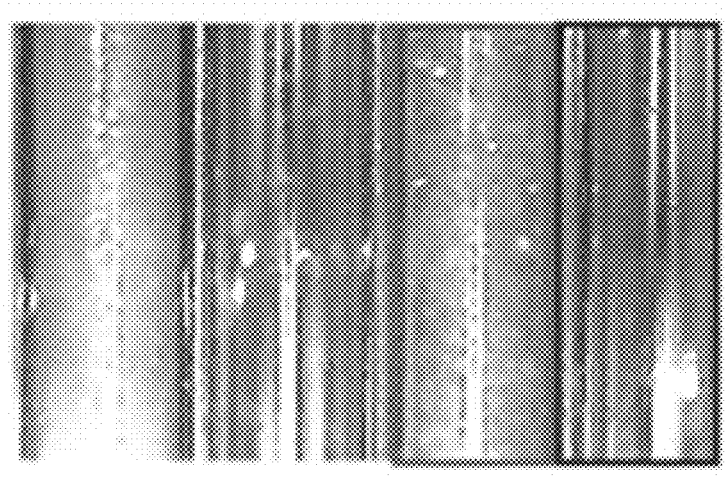
FIGS. 2A and 2B show the results of a capillary tube freeze assay that was performed at −20° C.
Figure 2B:
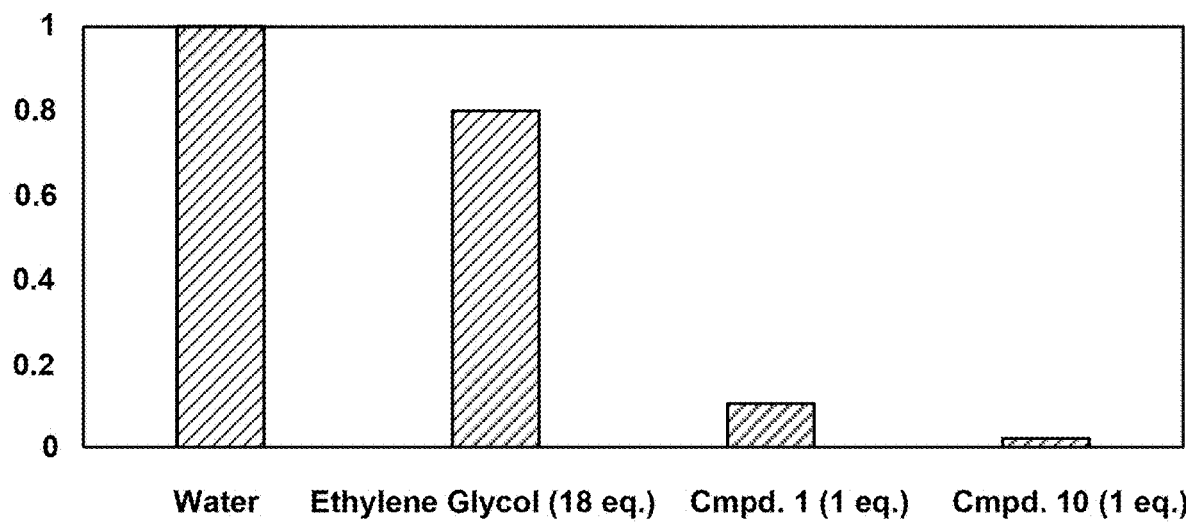
Figure 4E:
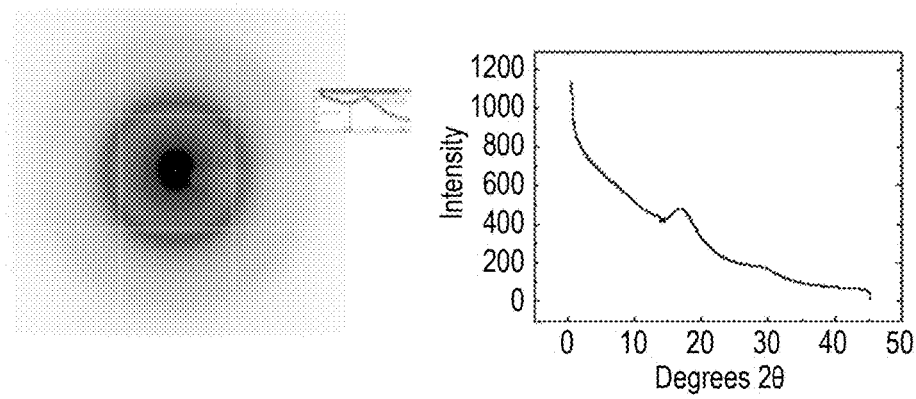
Figure 4F:
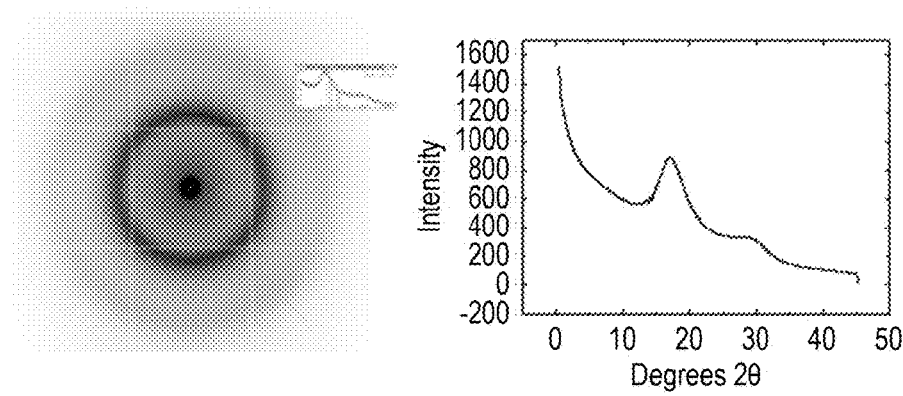
Figure 4G:
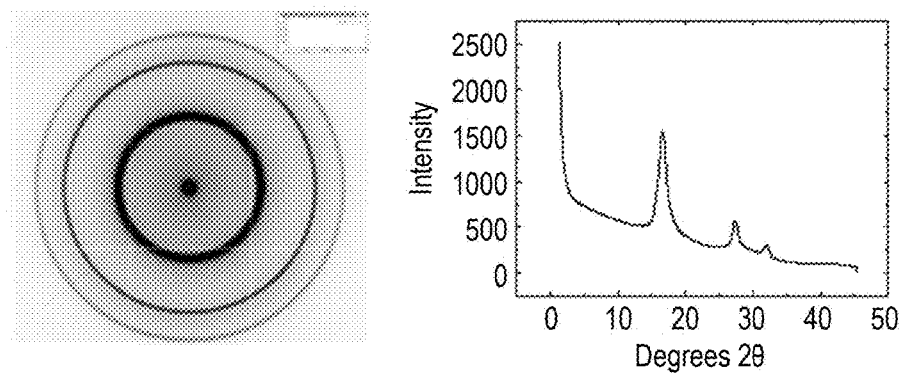
Figure 5E:
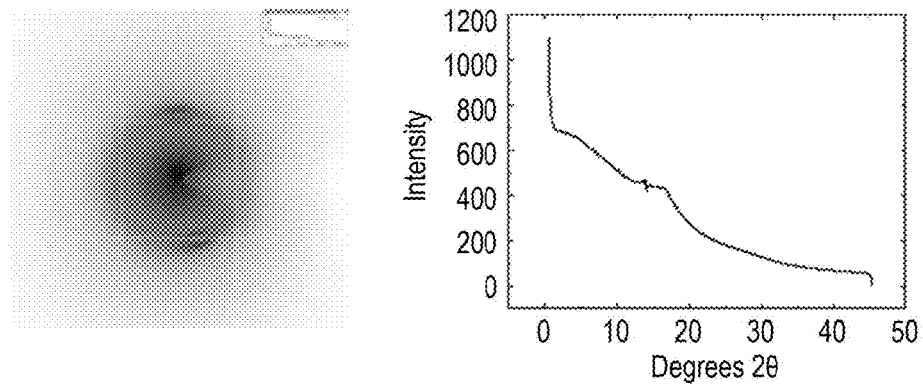
Figure 5F:
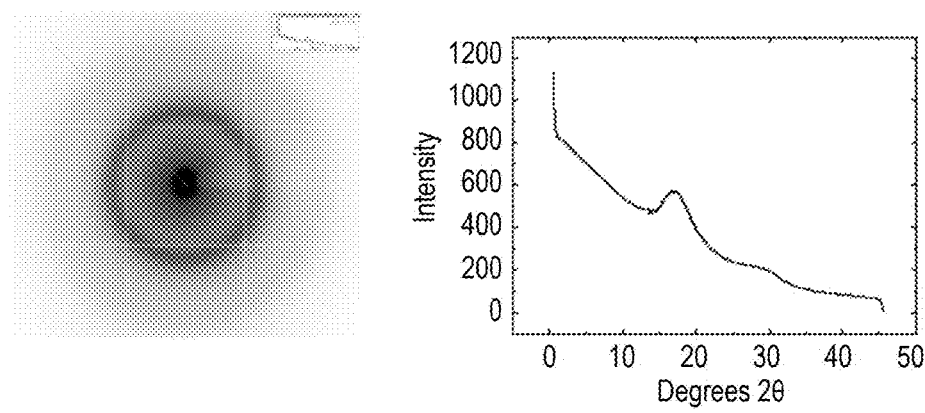
Figure 5G:
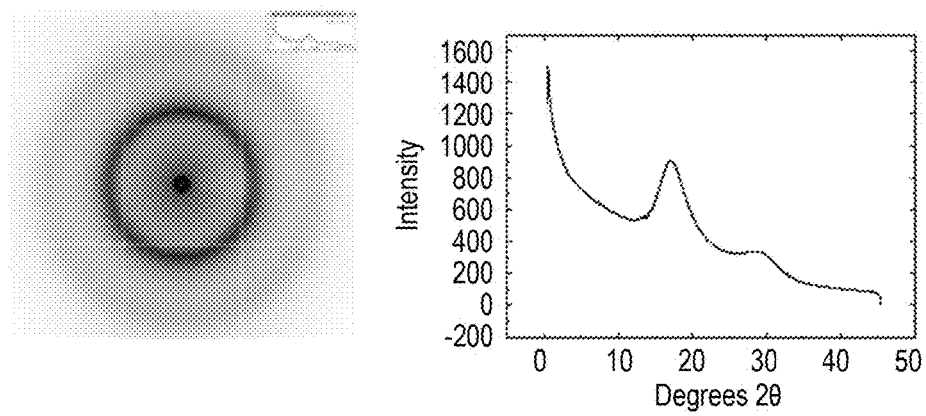

After sample preparation, all samples were slow cooled and incubated at −20° C. on a Peltier cooled plate. After one hour, samples were removed and immediately photographed using a digital camera attached to a 180× Stereo Zoom microscope (FIG. 2A). The water and EG samples showed significant ice crystal formation, although the EG sample showed less ice formation than the water-only sample. In contrast, neither of the samples containing the peptoid polymer compounds exhibited significant ice crystal formation. Normalized data is presented in FIG. 2B. Of note, the EG sample, containing a CPA concentration that was about 18 times higher than the peptoid sample concentrations, still exhibited significant ice formation whereas the peptoid samples did not.

Crystallographic x-Ray Diffraction Assays

In order to increase the throughput of library analysis, a crystallographic x-ray diffraction (XRD) technique was used to evaluate ice crystal formation. For these experiments, the compounds named "Compound 2," "Compound 8," "Compound 10," "Compound 11," "Compound 12," "Compound 13," and "Compound 58" were tested. Compounds 2, 8, 10, 11, 12, and 13 are peptoid polymers, the structures of which are provided in Table 2. Compound 58 is a peptoid-peptide hybrid, the structure of which is provided in Table 11. Compound 58 is similar to Compound 12, except that an arginine amino acid has been appended to the N-terminal end.

For these experiments, EG concentrations between 15% and 30% (v/v) were used. Typically, EG, DMSO, and other cryoprotectants are used during XRD sample analysis at concentrations of 35-40% (v/v) to vitrify solutions and avoid diffraction interference from ice crystals. Concentrations of 1 and 5 mg/mL of the peptoid and peptoid-peptide compounds were used. FIGS. 3A, 3B, and 3C illustrate exemplary XRD data under conditions of complete vitrification, partial vitrification with the presence of cubic ice, and freezing (cubic ice crystals), respectively. XRD data for Compounds 8, 10, 11, 12, 13, and 58 is provided in FIGS. 4A-4G and FIGS. 5A-5G. FIG. 3D provides ice rings scores for a variety of EG concentrations and two concentrations of Compounds 2, 8, and 12.

Several mixtures of the testing solution sample sets showed a strong anti-icing effect. FIG. 3D shows the experimental results of some peptoid polymer solutions compared to EG. "IceRing1" and "IceRing2" refer to ice formation scores, which range between 0 (no ice formation) and 15 (large ice formation). Compounds 2, 12, and 8 and others significantly reduced necessary EG concentrations while preventing ice formation.

The sample containing Compound 12 at a concentration of 5 mg/mL (0.5% (w/v)) and EG at a concentration of 17.5% (v/v) in water was ice-free after flash freezing. This particular mixture was found to completely eliminate all ice formation over multiple trials of flash freezing in a stream of liquid nitrogen vapor (FIG. 3A), and vastly outperformed a standard solution of 30% EG (FIG. 3B). In the figures, black spots and rings represent ice crystals. In comparison to EG at the same molar concentration, this anti-icing effect is 500 times stronger and, without being bound by any particular theory, suggests a non-colligative mechanism for anti-icing, which is the mechanism used by natural antifreeze proteins.

Larger Volume Assays

Figure 6A:
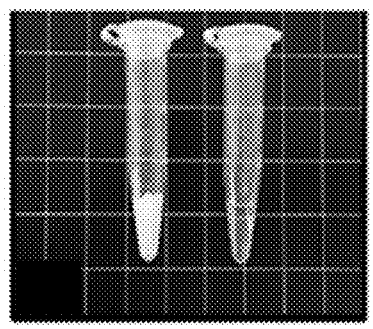
FIGS. 6A-6C show two solutions that were flash frozen, rewarmed, and subsequently refrozen. The control solution contained 22.5% (v/v) ethylene glycol (EG), while the test solution contained 22.5% EG and 5 mg/mL (0.5% (w/v)) Compound 12.
Figure 6B:
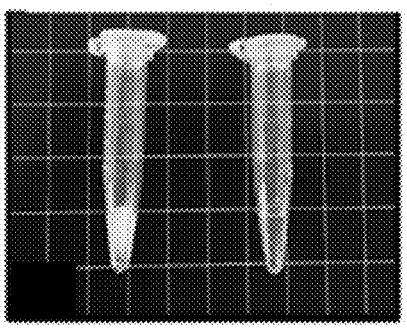

In order to test the usefulness of compositions of the present invention at larger scales, experiments were performed using solution volumes that are similar to volumes used for standard egg and stem cell preservation. For these experiments, two samples, one containing 22.5% EG and buffer only, and another containing 22.5% EG and 5 mg/ml (0.5% w/v) of Compound 12 and buffer, were flash frozen in liquid nitrogen. As shown in FIG. 6A, the Compound 12 solution showed complete vitrification with no ice formation immediately after removal from liquid nitrogen, while the control solution had clearly been frozen, yielding a mass of white ice crystals. The rewarming of the solutions in a 37° C. water bath led to an unexpected and beneficial result. The Compound 12 solution bypassed devitrification in less than 2 seconds upon rewarming (FIG. 6B, right), whereas chunks of ice were seen floating in the control sample (FIG. 6B, left) after 20 seconds. Condensation was seen on each of the tubes because the tubes were actually still much below room temperature. This result shows that Compound 12 acts as an active de-icer during thawing.

Figure 6C:
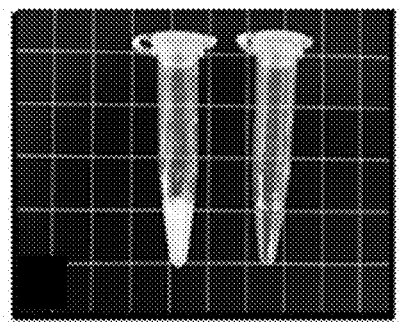

Furthermore, after leaving the 100 μL samples in a −20° C. freezer overnight, the Compound 12 solution was found to be unfrozen (FIG. 6C, right). This result shows that compositions of the present invention provide the ability to preserve samples at below 0° C. temperatures for long periods of time without any ice formation. Furthermore, these experiments show that ice-free conditions can be reached with hypothermic cryopreservation, or by the supercooling method, at −20° C. as well as near vitrification to −80° C. by incorporating compounds of the present invention to significantly reduce the critical concentration of penetrating CPAs and mitigate cryopreservation toxicity.

As shown here, a formulation of Compound 12 was found to prevent ice formation during vitrification in sub-milliliter volumes. In fact, the solutions were able to remain completely unfrozen at −20° C. and were also able to vitrify when flash frozen at −196° C. Currently, standard human egg cell preservation techniques for in vitro fertilization are limited to solution volumes of less than 5 uL (often 0.5 to 2.5 μL) while using 50% or greater cryoprotectant concentrations. Thus, Compound 12 was able to prevent ice formation in a practical volume, with exceedingly less cryoprotectant, which makes it useful, for example, for preserving human oocytes for in vitro fertilization.

Example 2. Cytotoxicity and Cryopreservation Screening

This example shows that compositions described herein have little to no cell toxicity and can achieve superior cryopreservation when compared to existing compounds, while reducing the necessary amount of CPAs and thus reducing CPA-associated toxicity.

Cytotoxicity Assays

In order to demonstrate the safety of cryoprotectant compositions of the present invention, a high-throughput cell-based cytotoxicity assay was developed utilizing the HEK 293 cell line, which is a sturdy and robust stem cell line grown from human embryonic kidney cells in tissue culture.

A Tecan Genesis Robotic Workstation was used to prepare solutions in 96- and 384-well plates. Solutions contained culture media, buffers, a cryoprotectant composition of the present invention (Compound 12) or DMSO. Solutions were adjusted to the desired pH. Serial dilutions were performed to obtain solutions containing various concentrations of Compound 12 and DMSO. Control experiments were performed using only culture media.

For these experiments, cells were seeded at low density (i.e., 10% confluence), exposed to solutions containing Compound 12 or DMSO, and placed in a 37° C. incubator. The cells were allowed to grow until control cells that were treated only with empty vehicle approached 70% confluence (typically about 3 to 5 days). Assessment for compound cytotoxicity was via MTT assay.

Figure 7:
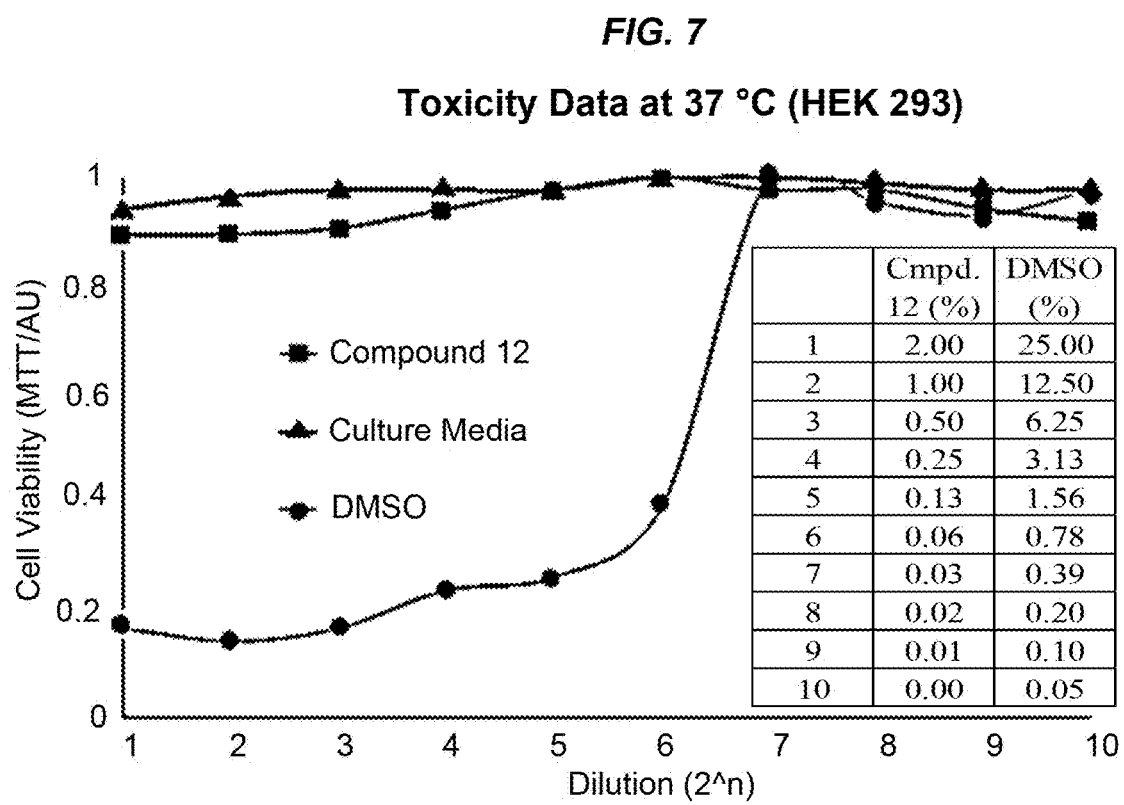
FIG. 7 shows the results of a cell toxicity study performed on HEK 293 cells in which Compound 12 (squares) or DMSO (circles) was added to cell culture media. A sample in which no Compound 12 or DMSO was added ("Culture Media" (triangles)) served as a control. Serial dilutions were performed in order to test different concentrations of Compound 12 and DMSO.

As can be seen in FIG. 7, the toxicity of Compound 12 did not significantly deviate from the that of culture media alone when analyzed by MTT assay. On the other hand, DMSO did not allow for warm survival for an extended period of time at any concentration above 0.5% (v/v). Notably, Compound 12 did not show toxicity at the concentrations in which it can prevent ice formation in a non-biological sample (0.5% w/v) and did not show significant toxicity at concentrations four times greater than this concentration, either.

These results show that compositions of the present invention were effective at ice-prevention even at concentrations where DMSO toxicity significantly reduced cell survival.

Cryopreservation Assays

Initial cryopreservation assays were performed using very simple solutions, with and without the addition of Compound 12, in order to minimize confounding outside factors. For this first set of experiments, two sample solutions were prepared. The first sample solution contained simple buffer and ethylene glycol (EG) at a concentration of 22.5% (v/v), and the second sample solution contained simple buffer, EG (22.5% (v/v)), and 5 mg/mL (0.5% (w/v)) of Compound 12.

HEK 293 cells were grown until 70% confluent, then treated with trypsin to remove adhesion proteins and yield free floating cells. Cells were counted using a hemocytometer and sample cell concentrations were adjusted to final concentrations of 10,000 cells per microliter. Cells were then compressed into tight pellets by centrifugation, and each sample was subsequently mixed with 20 μL of one of the sample solutions. Samples were then flash frozen by immersion in liquid nitrogen, followed by rewarming in a 37° C. water bath. After the freeze-thaw process, cells were suspended in a 400× volume of culture media for recovery. The positive control sample was treated with culture media at 37° C. and not subjected to the freeze-thaw process. The negative control sample was treated with culture media only during the freeze-thaw process. After recovery, cells were stained with Calcein AM for 30 minutes and cell viability was measured using a fluorescence plate reader.

Figure 8:
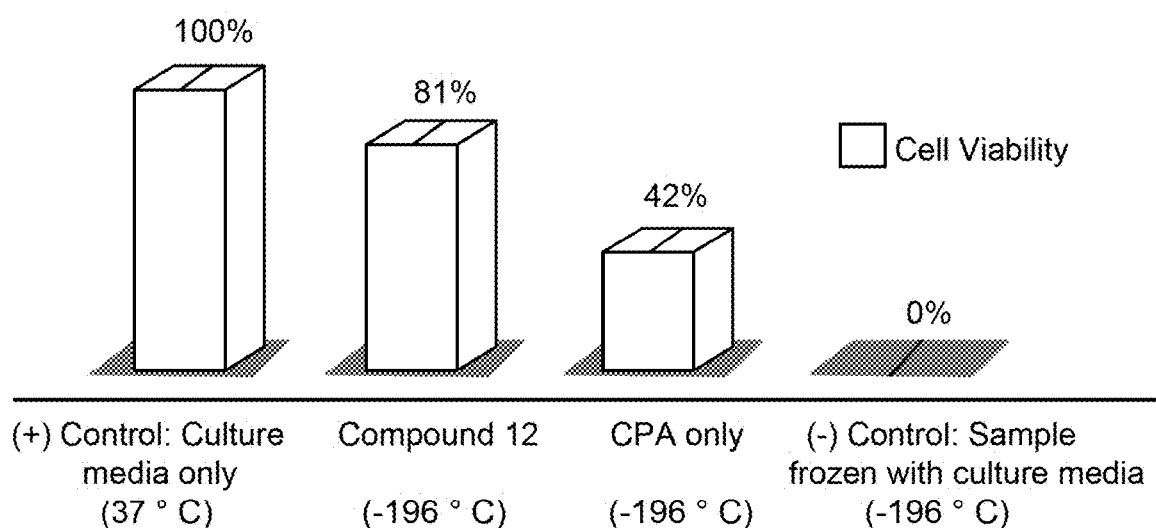
FIG. 8 shows the results of a cryopreservation assay performed on HEK 293 cells, comparing a solution containing ethylene glycol (EG) to a solution containing EG and Compound 12. Cell viability was measured 12 hours post-thaw.

As shown in FIG. 8, the addition of Compound 12 greatly improved cell survival and demonstrated the ability of this compound to cryopreserve cells. It was observed that the sample containing Compound 12 achieved complete vitrification without ice formation during the freezing process. In addition, the process of devitrification was bypassed much more rapidly compared to the sample lacking Compound 12.

Figure 9:
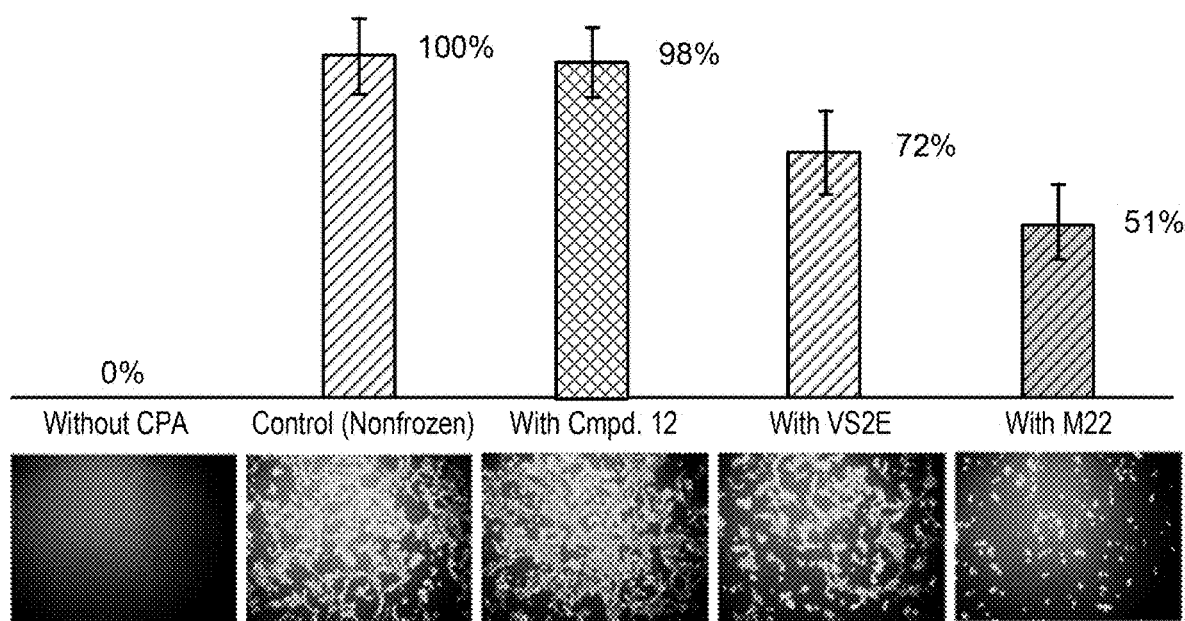
FIG. 9 shows the results of a cryopreservation assay performed on HEK 293 cells, comparing a solution containing 5 mg/mL of Compound 12 plus a mixture of glycols, disaccharides, and a general buffer to solutions containing VS2E or M22. Cell viability was measured 16 hours post-thaw. Cells were vitrified with liquid nitrogen (LN2).

A second set of experiments was performed to evaluate the cryopreservation potential of a formulation that contained 5 mg/mL of Compound 12 plus a mixture of glycols, disaccharides, and a general buffer. Post-thaw survival following vitrification in liquid nitrogen was evaluated as described above. As can be seen in FIG. 9, the formulation achieved near 100% (i.e., 98%) post-thaw survival of the cells, which was similar to the control group that was not exposed to freezing treatment. The cell morphologies and florescence signals looked identical to the non-frozen controls, which indicated that little damage occurred to the cells during the experiment.

As part of the second set of experiments, the cryopreservation potential of the formulation was compared to two known cryopreservation reagents. VS2E is a DMSO-free and serum-free solution containing non-chemically defined polymers (see, e.g., Nishigaki et al. *Int. J. Dev. Biol.* 55:3015-311 (2011)), and M22 is an organ vitrification solution available from 21$^{st}$ Century Medicine. FIG. 9 shows that the formulation containing Compound 12 achieved superior cryopreservation, as cell survival was 72% and 51% for VS2E and M22, respectively. It should be noted that for the M22 sample, background fluorescence may have skewed this result, as a count of live cells in the image suggested that far fewer than 51% of the cells had survived.

The compositions of the present invention were highly effective at preventing ice formation in solutions containing significantly reduced ethylene glycol. In particular, low concentrations of the compositions (e.g., 0.5% (w/v)) were sufficient to block ice growth during vitrification and to keep solutions in a liquid, ice-free state on the 20 uL scale, which is a scale that is useful for the preservation of various types of cells.

In summary, these results show that compositions of the present invention can achieve superior cryopreservation and reduce the necessary amount of CPAs, thus reducing cell toxicity that is associated with CPAs. The superior properties of the compositions of the present invention are especially useful for the treatment of particularly sensitive cell lines and/or when cells need to be cultured for longer time periods.

Example 3. Supercooling of Cells for Extended Time Periods

This example shows that successful cell preservation using the supercooling formulas and methods described herein is feasible for extended time periods.

Transporting preserved cells and tissue from lab to patient at high sub-zero temperature could result in: 1) increased cell survival and prolonged storage period (beyond 24 hrs) compared to 4° C. storage; (2) reduced transport cost compared to cryopreservation by avoiding the use of LN2; and (3) avoidance of ice damage that occurs during water phase transitions in deep cooling storage protocols (e.g., −80° C. and −196° C.). Traditional penetrating CPAs are not able to reach cooler temperatures beyond −6° C. during supercooled storage due to adverse toxicity. Storage at lower temperatures can provide longer metabolic suspension for longer cell storage periods and can also achieve the best practical use with integration in cold chain infrastructure for −20° C. cooling/shipping.

Supercooling Preservation Protocol

We compared various formulas using HEK293 and K562 cells. Briefly, 100 μL of cells (0.5×10$^6$ cells/mL) were suspended in test cryoprotectant (or in media for the non-frozen control) in replicates. Test tubes were placed on a shelf in the −20° C. freezer and removed at designated time points. Samples were warmed in a 37° C. water bath and 10 μL of each was aliquoted into recovery wells containing 500 uL DMEM+10% FBS and placed in an incubator (37° C., 5% CO$_2$) for 16 hours to allow cells undergoing apoptosis to pass. Cells were either stained with alamarBlue® or data was acquired by flow cytometry to improve comparison to non-frozen cells at the same growth stage as those that were subjected to cooling and warming protocols. Cell counts were normalized to non-frozen arms.

Samples were either placed directly in the −20° C. freezer in cryovials or more precisely controlled by placing into a Mr. Frosty, which is an isopropanol containing device used to control the rate of cooling a cryovial to ~1° C./min (when placed in a −80° C. freezer). The appearance of each tube at −20° C. was examined at each of the test intervals after cooling to −20° C. and noted as either liquid, semi-solid, or crystalline, which was designed to inform correlation between ice formation and cell survival.

Results

Cell survival was demonstrated with formulas for 1- and 3-day storage at −20° C. Increased cell survival was observed for formulas that exhibited comparatively less or no crystal formation. However, a better correlation for increased cell survival was noticed for formulas containing active peptoid. The formulas also provided consistent cell survival rates after day 1 and day 3, whereas DMSO and media show a drastic difference between time points.

The formulas were further tuned with cross experiments of various base buffers, small molecule CPA concentrations, and select cellular protection agents. Protocol improvements examined cells preservation at (−20° C.) after 3, 24, 48, 72, and 120 hours along with many other formulation comparisons. We also expanded our cell models to include K562 cells as a representative of a non-adherent blood cell and Jurkat cells.

Figure 10A:
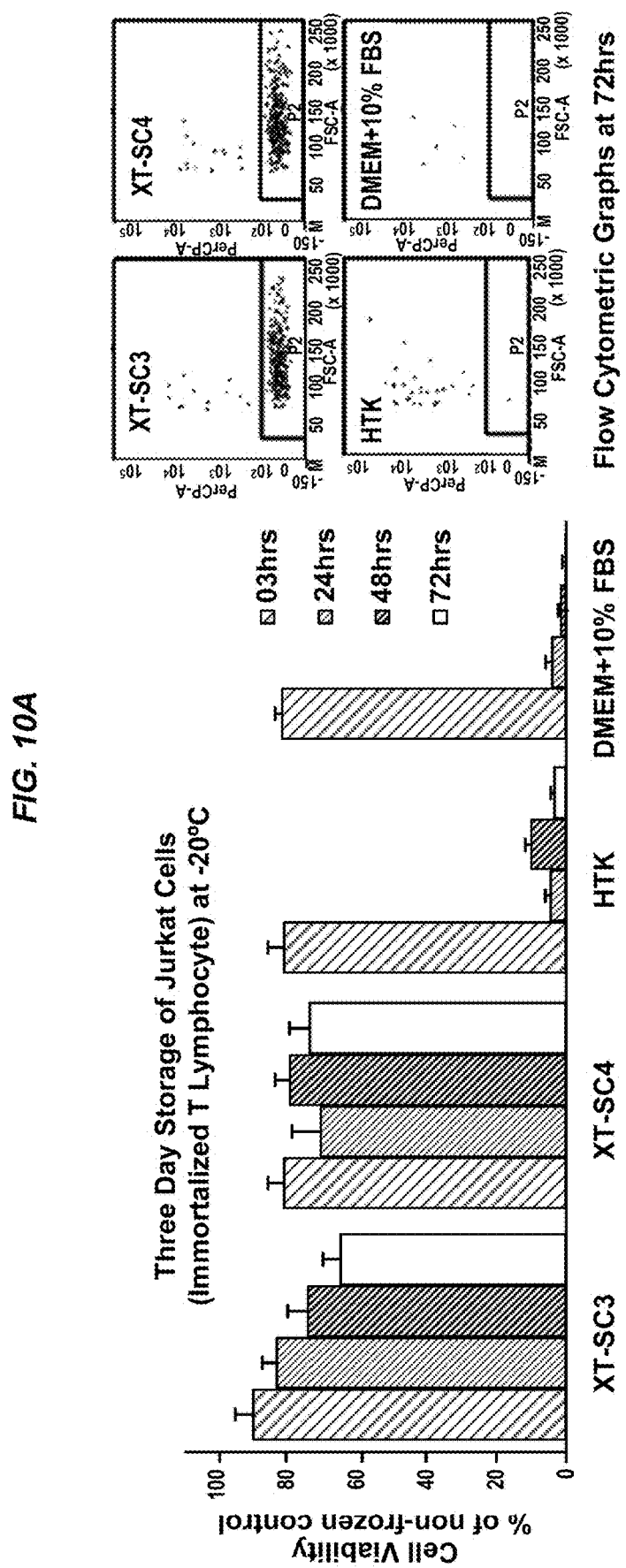
FIG. 10A shows an example of flow cytometric data collected after 72 hr storage of Jurkat cells at −20° C. Cell number was normalized to a non-frozen control for comparison. Formulas XT-SC3 and XT-SC4 contain HTK buffer, Compound 12, and other components. Both HTK buffer and DMEM+10% FBS showed little to no survival after 24 hr storage. XT-SC4 showed little to no cell death after 72 hrs and XT-SC3 showed only a slight decline in cell survival as time points extended.
Figure 10B:
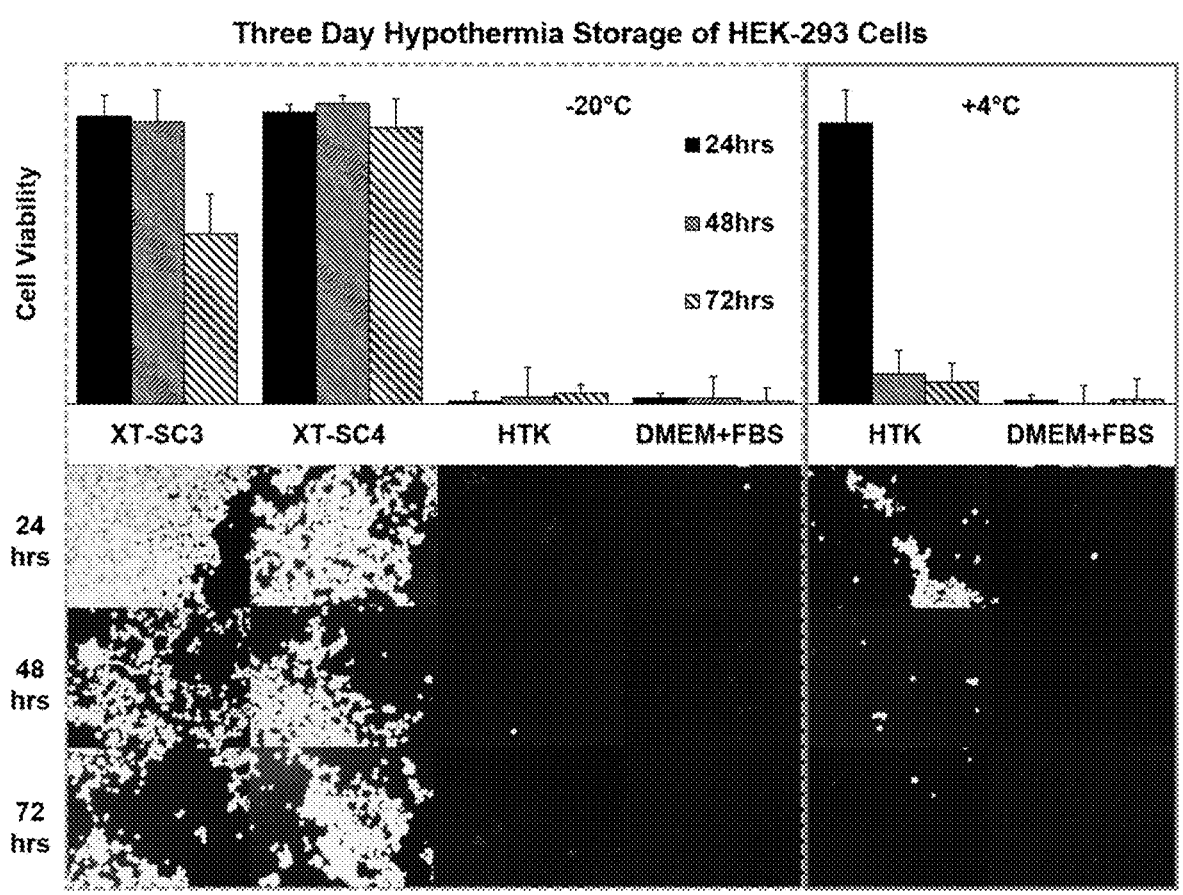
FIG. 10B shows a fluorescence viability assay after 72 hr storage of HEK293 cells at −20° C., corroborating flow cytometry results with Jurkat cells. Here, HTK and DMEM/FBS provided no survival at −20° C. and very poor survival at 4° C. after 24 hrs.

FIGS. 10A and 10B show that the methods of the present invention enabled supercooling of cells at −20° C. Formulas containing peptoid polymers such as Compound 12 had the unique ability to preserve cells at −20° C. with significant viability after 72 hrs under supercooled conditions. In contrast, HTK buffer at its proposed shipping/working temperature (4° C.), an FDA approved organ preservation solution designed to ship human organs for transplant, only maintained cell survival less than 24 hrs at 4° C.

Example 4. Supercooling of Primary Genitourinary Cells and Tissues for Transplant This example shows the successful preservation of primary genitourinary (GU) cells using the supercooling formulas and methods described herein.

Examples of human GU cell types include BJ (human fibroblast foreskin), PC-3 (human prostate adenocarcinoma), and SK-OV-3 (human ovary adenocarcinoma). Examples of primary GU cell types include primary corpus cavernosum (CC) cells such as smooth muscle and endothelial cells. In penile tissue, CC endothelial and smooth muscle cells provide the basic form and function. Cell preservation experiments can be performed using GU explants.

Endothelial Cells

Briefly, corpus cavernosum (CC) tissue was harvested, processed, digested and filtered to yield single endothelial cells which were then resuspended in cell medium followed by cultivation for 5 days. See, Chung et al., Korean Journal of Urology, 53(8):556-563 (2012). Confluent adherent endothelial cells were further processed, resuspended in RPMI medium and filtered through a 70 μm nylon mesh. The cells were then incubated with biotinylated anti-rat CD146 antibody at 20° C. for 30 min. After washing, cells were resuspended in buffer and were incubated with streptavidin coated magnetic beads. Magnetically labelled CD146 cells were isolated using a magnetic column. See, Weber et al., Pediatr Res, 70(3):236-41 (2011). The eluate was resuspended in EC medium and cultured.

Smooth Muscle Cells

Cavernosal tissue was washed, processed and placed in a minimal volume of supplemented DMEM at 37° C. in a humidified atmosphere of 95% air and 5% $CO_2$. See, Pilatz et al., European Urology, 47(5):710-719 (2005). After further processing, cells migrated out of the explants (4-10 days), the explants were removed, and the cells were allowed to achieve confluence with D-valine in culture medium to control the outgrowth of fibroblast cells without affecting smooth muscle cell morphology. Cells were examined for alpha smooth muscle actin (α-SMA) expression by immunostaining and fluorescence microscopy.

Supercooling Preservation Protocol

A small amount of CC endothelial and smooth muscle cells were used at approximately 70% average confluence. Smaller volumes were necessitated for this experiment, so 1 μL of a prepared cell slurry was suspended in 19 μL (250,000 cells/mL) of several formulas in a Biorad 96-well PCR plate. The well plate was placed in a −20° C. freezer equipped with a Peltier plate for temperature stability and cells were sampled at designated time points. A 24-well tissue culture plate containing 1 mL of either Medium 199 with 20% FBS (primary cells) or DMEM+10% FBS (HEK293 control) were pre-equilibrated at 37° C. with 5% $CO_2$ for 1 hour. The cryopreserved cell solutions (20 μL) were pipetted into 24-well tissue culture plate and allowed to recover overnight followed by survival assay with calcein AM 24 hours post-warm. HEK293 cells served as an external cell counting standard and quantitated in high fidelity ($R^2>98$).

Results

Figure 11:
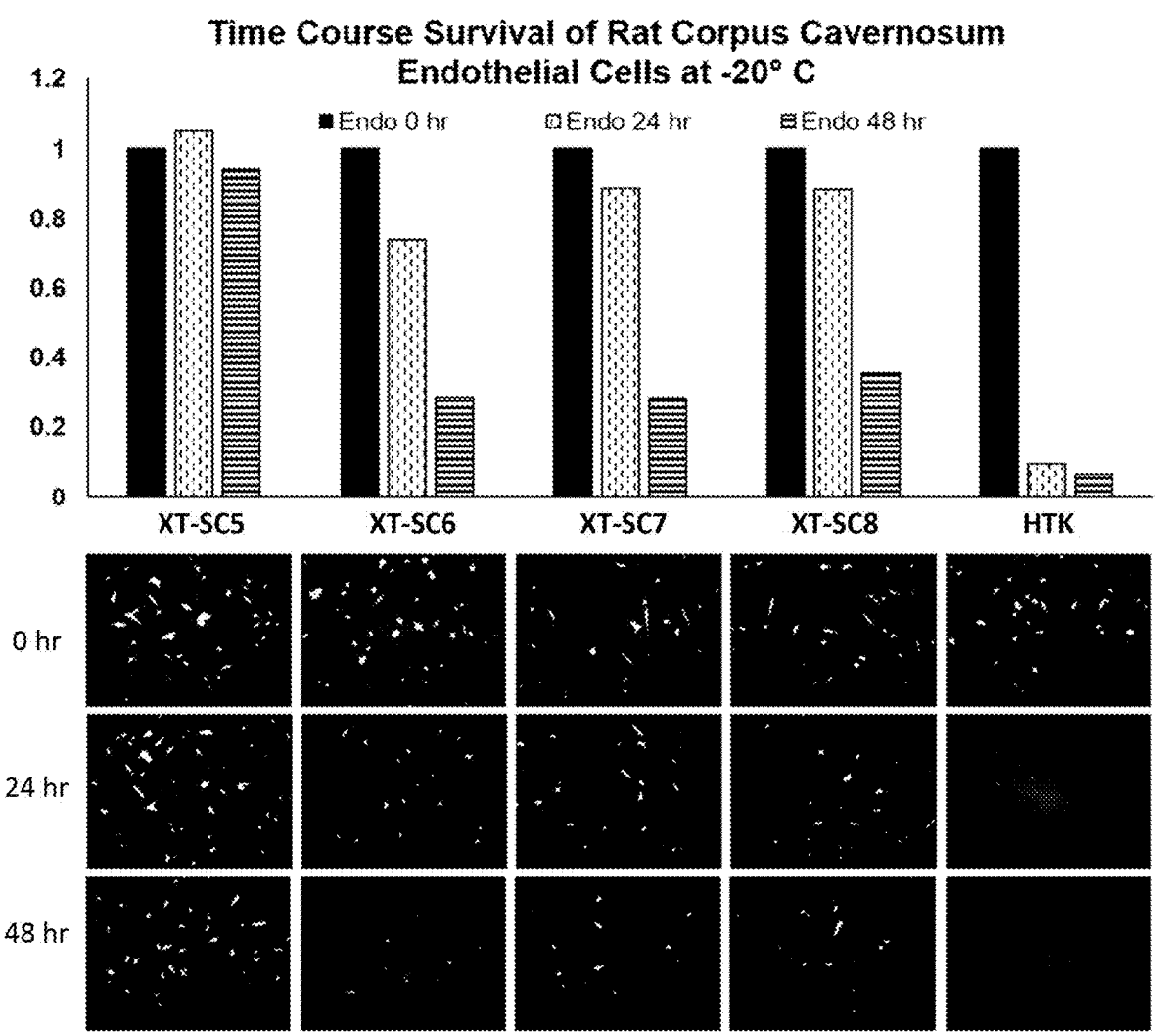
FIG. 11 shows a time course survival of rat corpus cavernosum (CC) endothelial cells stored in supercooling formula (XT-SC5 to 8) and HTK solution at −20° C. for up to 48 hrs. After treatment with supercooling media, the cells were recovered into culture media (50× dilution) at 37° C. for 24 hrs prior to staining with Calcein AM. Quantitative fluorescence signaling indicates cell survival in the bar chart and the correlated cell images are shown on the bottom.

Formulas mixed with primary cells stored at −20° C. appeared unfrozen at each time point after supercooling to −20° C. FIG. 11 shows that HTK solution failed to protect CC endothelial cells at −20° C., resulting in zero cell survival after 48 hrs, probably due to solid ice formation during the preservation. Similar results were obtained for CC smooth muscle cells. Importantly, the use of supercooling formula XT-SC5 resulted in higher survival of primary CC endothelial cells and smooth muscle cells after 48 hrs compared to formulas XT-SC6, XT-SC7, and XT-SC8. XT-SC5 shares the same basic buffer as XT-SC6, XT-SC7, and XT-SC8, but with the addition of 0.5% peptoid Compound 12. All four formulas contain different concentrations of small molecule CPAs (XT-SC5=XT-SC6, XT-SC7=1.25X, and XT-SC8=1.5X).

The preservation and time course survival study of endothelial cells reveals that XT-SC5 with peptoid polymer provides exceptional cell survival (94%) over a time course of 48 hrs, while formulas without peptoid polymer and with increased CPA concentration exhibit reduced survival of endothelial cells over 48 hrs (approximately 20%). The overall trend of smooth muscle cell survival is consistent with the result obtained from the endothelial cell preservation.

Example 5. Supercooling of Genitourinary Cells from Model Cell Line

This example shows the successful preservation of genitourinary (GU) cells from a model human GU cell line using the supercooling formulas and methods described herein.

Cryopreservation experiments were performed at −20° C. Survival, viability, and proliferation were examined. Cells were analyzed by fluorescence plate reading assays.

The cell line SK-OV-3 (human ovary adenocarcinoma) was preserved as a model human genitourinary cell type at −20° C. in various cryopreservation solutions containing a peptoid polymer (e.g., Compounds 1-8). Each solution had 4 identical replicas at 5 time points. At each time point, the cell numbers were quantitated with an external standard.

Briefly, 100 μL of cells (0.5×10$^6$ cells/mL) were suspended in test cryoprotectant (or in media for the non-frozen control) in replicates. Test tubes were placed on a shelf in the −20° C. freezer and removed at designated time points. Samples were warmed in a 37° C. water bath and 10 IA of each was aliquoted into recovery wells containing 500 μL DMEM+10% FBS and placed in an incubator (37° C., 5% $CO_2$) for 16 hours to allow cells undergoing apoptosis to pass. Cells were stained and cell counts were normalized.

We compared the survival of cells in formulas that were forced to freeze versus unfrozen formulas. As set forth in Table 12, most of the formulas showed very high survival over 6 days when they remained unfrozen after supercooling to −20° C. ("Liquid") compared to formulas that were forced frozen by crystal seeding with ice crystals ("Frozen"). These results demonstrate that cells which remain in liquid at −20° C. for 6 days have a much higher survival rate and establish that supercooled, non-frozen solutions enhance cell survival under conditions of reduced temperature and metabolism.

TABLE 12

Day 6 Survival

| Compound | Frozen | Liquid |
|---|---|---|
| 1 | 18% | 83% |
| 2 | 15% | 82% |
| 3 | 7% | 20% |
| 4 | 3% | 83% |
| 5 | 20% | 86% |
| 6 | 16% | 91% |
| 7 | 18% | 50% |
| 8 | 18% | 73% |

Example 6. Survival and Proliferation Studies on Supercooled Cells

This example shows that cells preserved in accordance with the supercooling formulas and methods described herein are viable and demonstrate enhanced survival and proliferation compared to control samples without peptoid polymers.

SK-OV-3 Cells

We evaluated cell survival and proliferation following supercooled preservation of SK-OV-3 cells at −20° C. in several formulas for 3 days in a solution containing significantly reduced small molecule cryoprotectant (about 5× lower concentration). A comparison was made between a cryopreservation formula with 1% Compound 12 ("XT Formula+1% Compound 12") and XT Formula only, a 10% DMSO formula (standard for cryopreservation), and/or DMEM (base media, negative control). "XT Formula" contains HTK buffer and other components.

Figure 12:
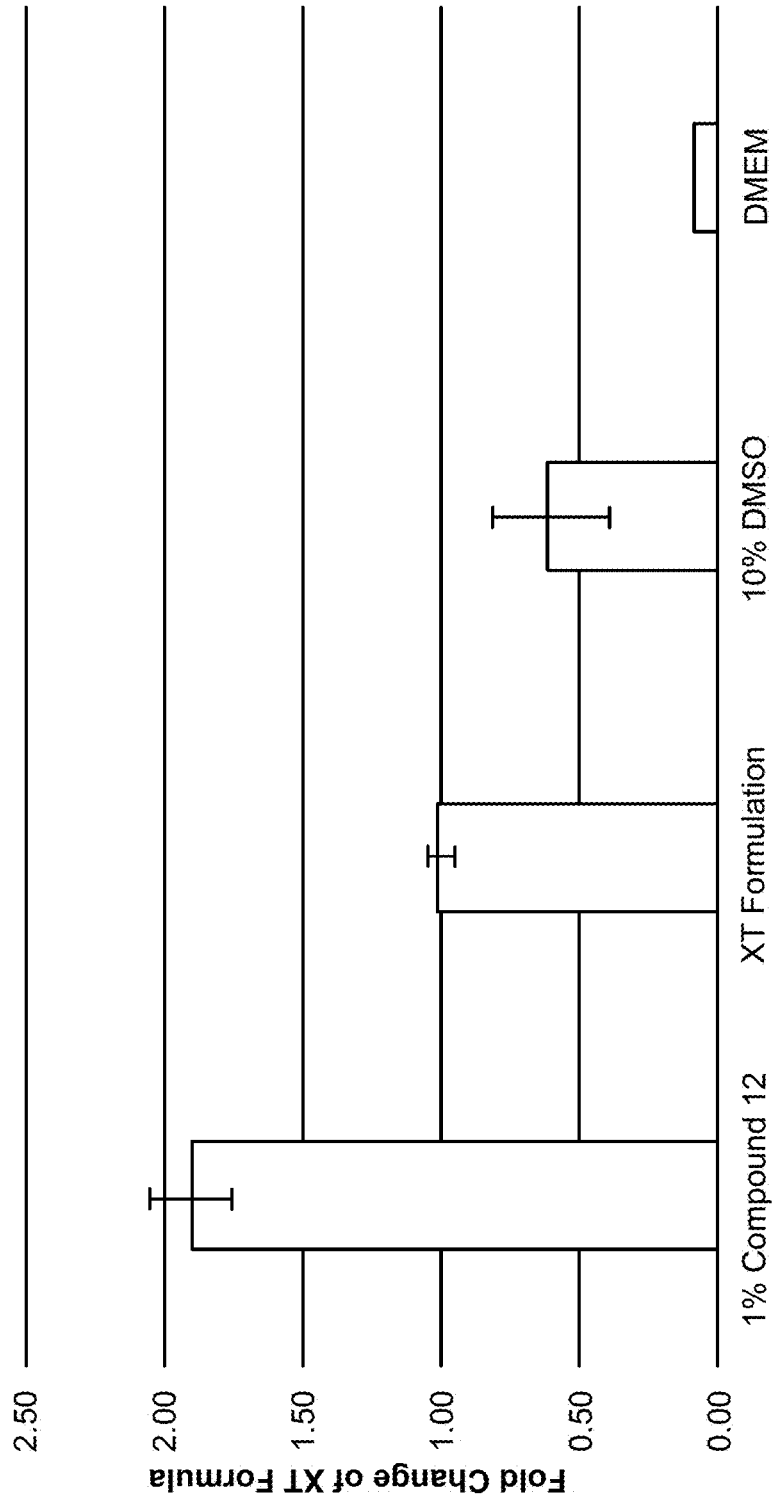
FIG. 12 shows the survival of SK-OV-3 cells cryopreserved for 3 days at −20° C. in either XT Formula with 1% Compound 12, XT Formula only, 10% DMSO formula, or DMEM cell media only. Cell survival was measured 1 day post-warming.

FIG. 12 shows that the formula containing a peptoid polymer was effective at enhancing SK-OV-3 cell survival following the supercooling preservation methods described herein. In particular, at least 50% of the supercooled cells in the peptoid formula survived at 1 day post-warming compared to the starting cell number and the number of cells in the peptoid formula at 1 day post-warming was at least about 2 to 4-fold greater compared to the formula without the peptoid polymer or the DMSO formula.

Figure 13:
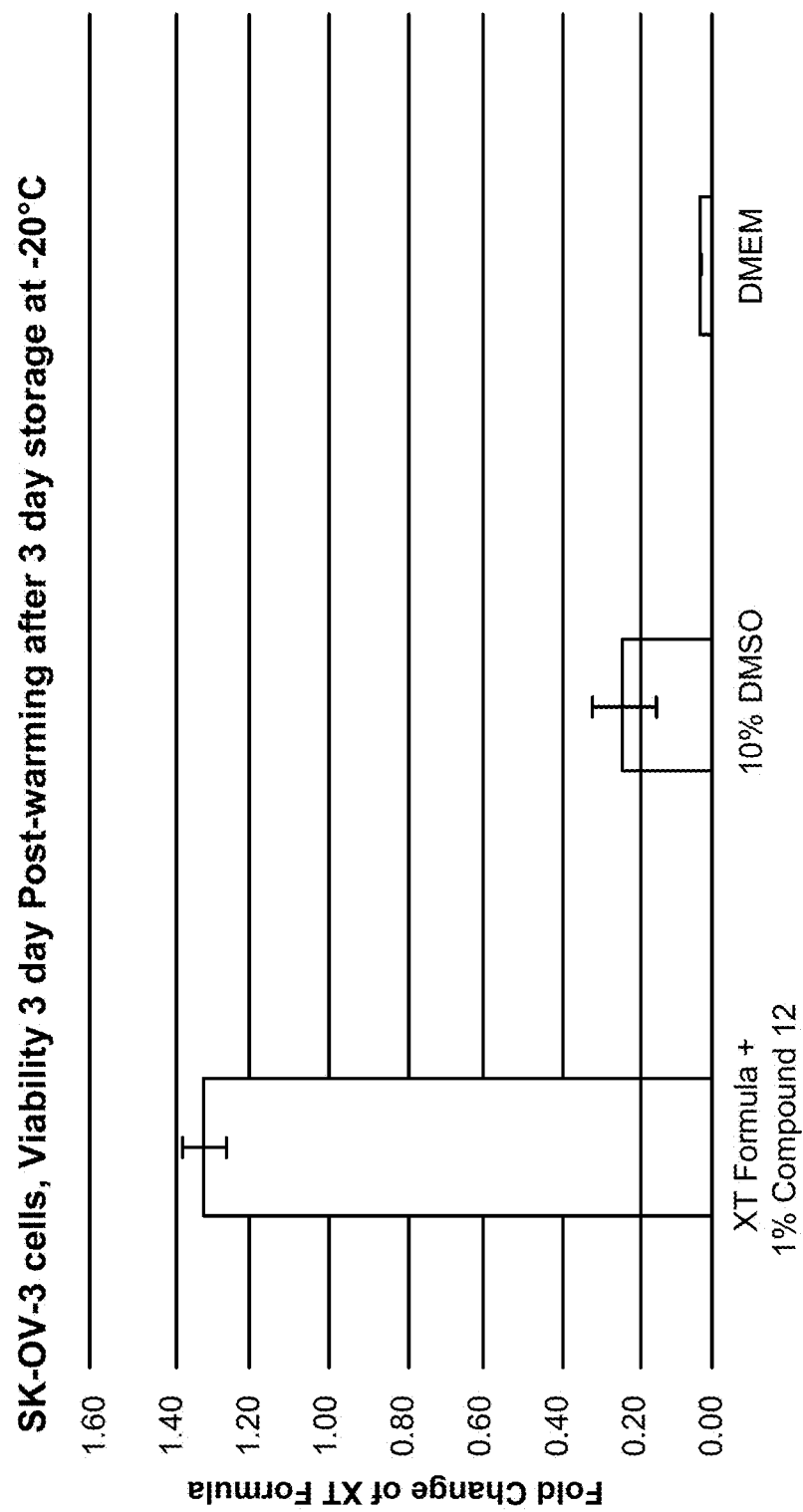
FIG. 13 shows the proliferation of SK-OV-3 cells cryopreserved for 3 days at −20° C. in either XT Formula with 1% Compound 12, 10% DMSO formula, or DMEM cell media only. Cell viability was measured 3 days post-warming.

FIG. 13 shows that the formula containing a peptoid polymer was effective at enhancing SK-OV-3 cell viability following the supercooling preservation methods described herein. In particular, the number of cells in the peptoid formula at 3 days post-warming was at least about 5 to 6-fold greater compared to the formula containing DMSO.

K562 Cells

We evaluated cell proliferation following supercooled preservation of K562 cells at −20° C. in several formulas after 3, 6, or 7 days of incubation post-warming. K562 cells were preserved by supercooling for 3 days at −20° C. comparing XT Formula with a peptoid polymer (e.g., Compound 12) to XT Formula only (i.e., no peptoid), 10% DMSO formula (standard for cryopreservation), and DMEM (base media, negative control). Briefly, 200 μL of cells (0.5×10$^6$ cells/mL) were suspended in test cryoprotectant (or in media for the non-frozen control) at 4° C. for 10 minutes in cryovials by using aluminum block in replicates. Test tubes were placed on a shelf in the −20° C. freezer and removed at designated time points. Samples were warmed in a 37° C. water bath with gentle swirling and 2 μL of each (10,000 cells) was aliquoted into recovery wells containing 200 μL DMEM+10% FBS and placed in an incubator (37° C., 5% $CO_2$). Cells were incubated for 3, 6, or 7 days, stained at various intervals, and analyzed by plate reader.

Figure 14:
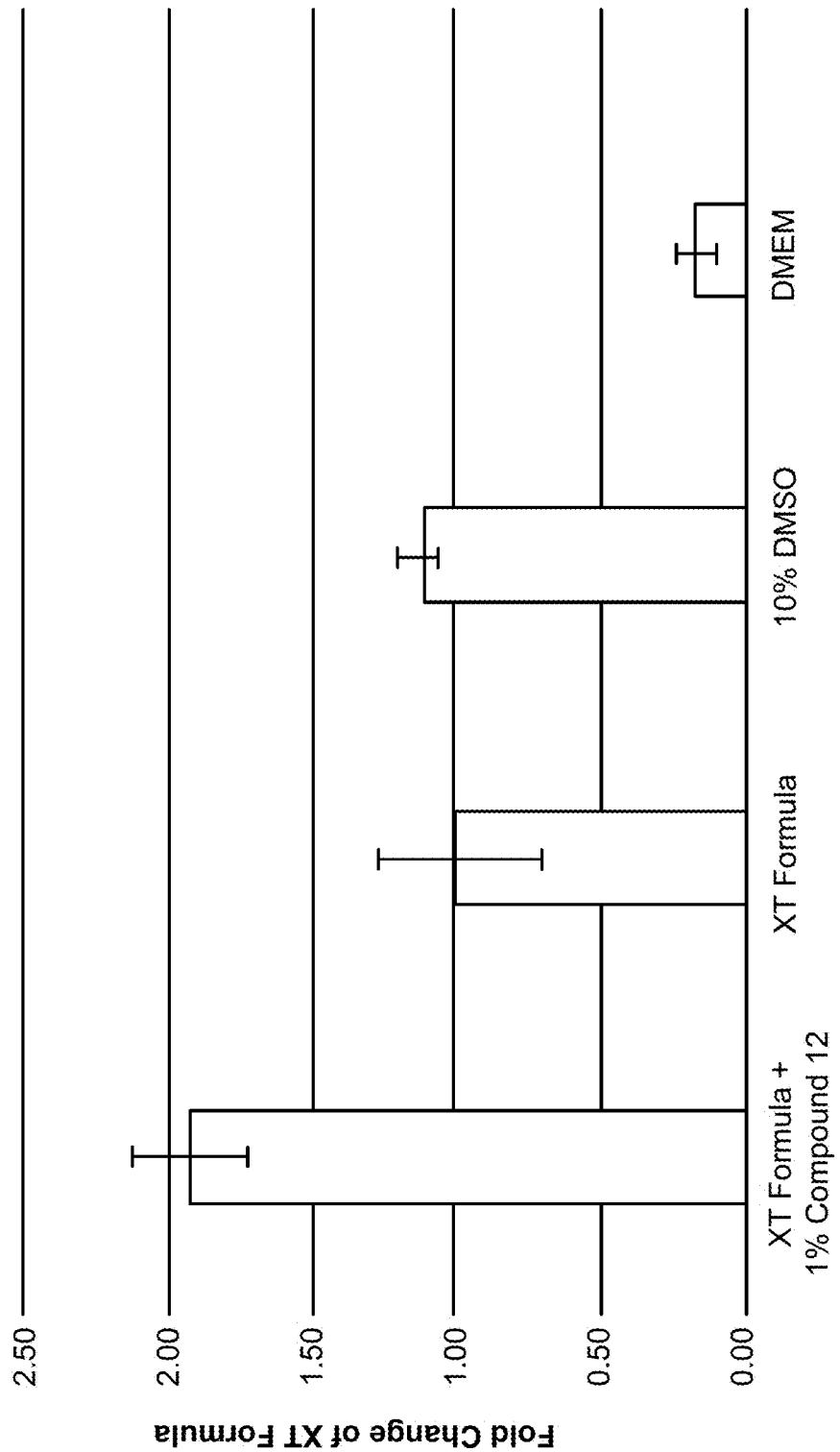
FIG. 14 shows the proliferation of K562 cells cryopreserved for 3 days at −20° C. in either XT Formula with 1% Compound 12, XT Formula only, 10% DMSO formula, or DMEM cell media only. Cell viability was measured 3 days post-warming.
Figure 15:
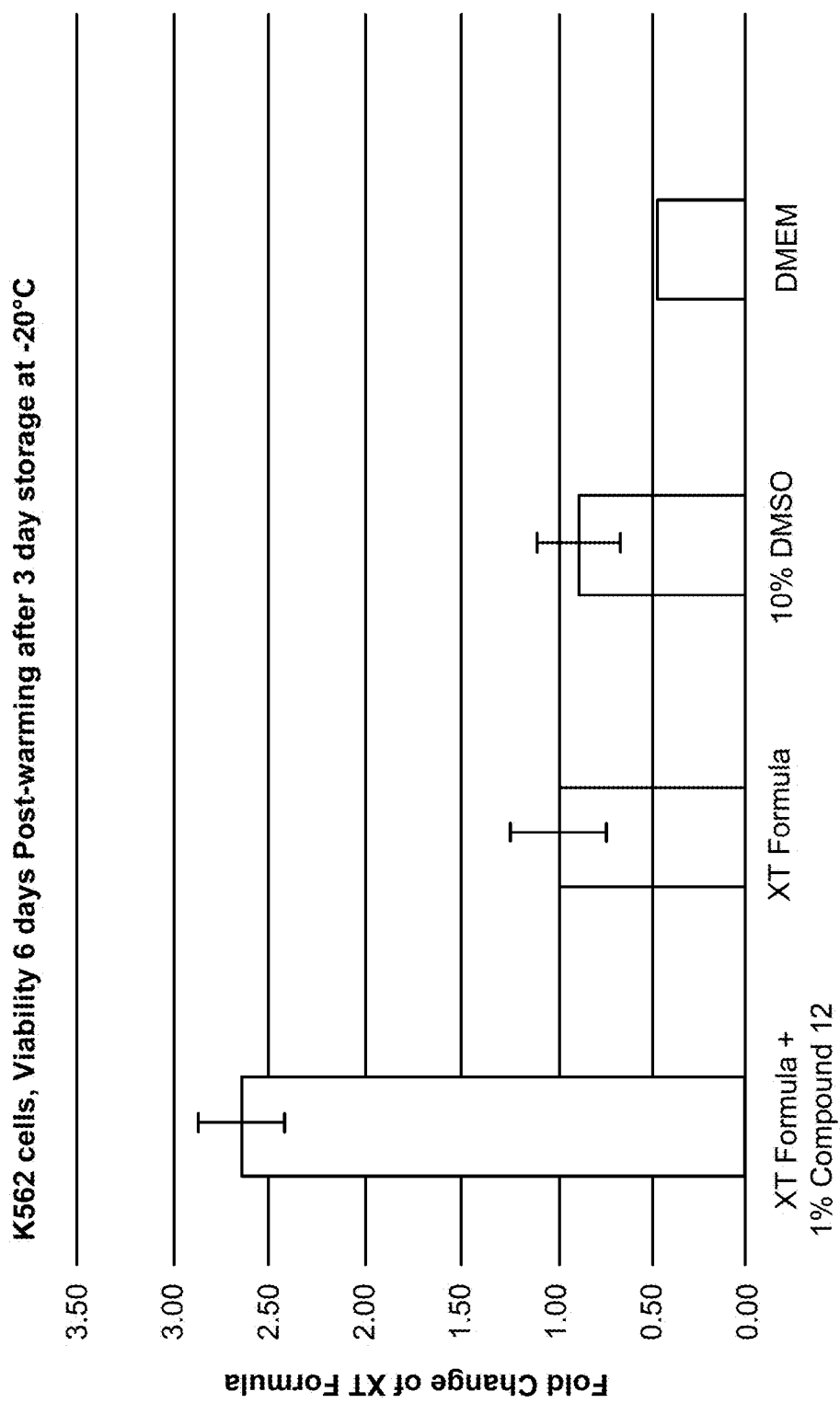
FIG. 15 shows the proliferation of K562 cells cryopreserved for 3 days at −20° C. in either XT Formula with 1% Compound 12, XT Formula only, 10% DMSO formula, or DMEM cell media only. Cell viability was measured 6 days post-warming.

FIGS. 14 and 15 show that the formula containing a peptoid polymer was effective at enhancing K562 cell viability following the supercooling preservation methods described herein. In particular, FIG. 14 shows that the number of cells in the peptoid formula with Compound 12 at 3 days post-warming was at least about 1 to 2-fold greater compared to the formula without the peptoid polymer or the DMSO formula. FIG. 15 shows that the number of cells in the peptoid formula with Compound 12 at 6 days post-warming was at least about 2 to 3-fold greater compared to the formula without the peptoid polymer or the DMSO formula.

Figure 16:
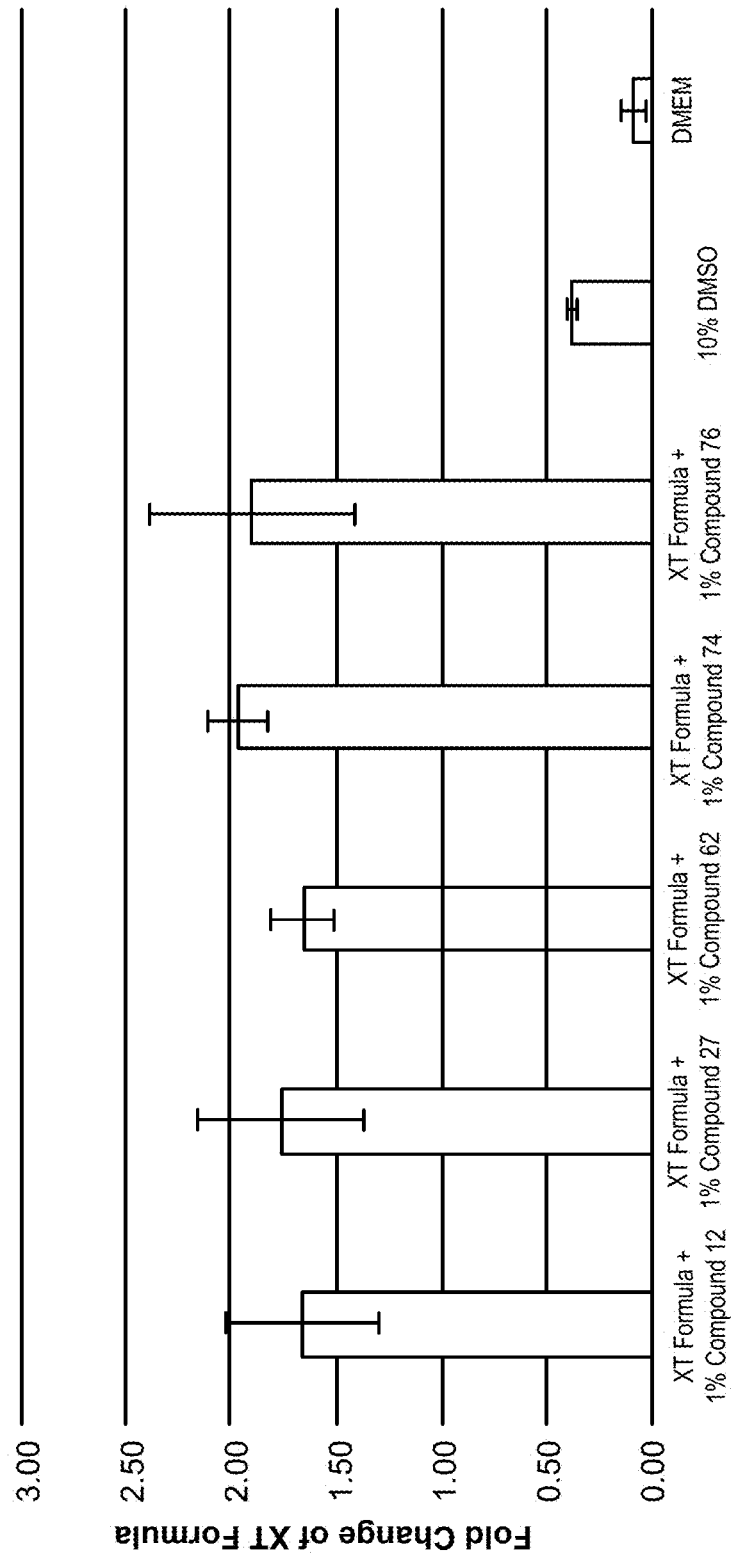
FIG. 16 shows the proliferation of K562 cells cryopreserved for 3 days at −20° C. in either XT Formula with 1% Compound 12, 27, 62, 74, or 76, 10% DMSO formula, or DMEM cell media only. Cell viability was measured 7 days post-warming.

FIG. 16 shows that numerous formulas containing various peptoid polymers were effective at enhancing K562 cell viability following the supercooling preservation methods described herein. In particular, the number of cells in the peptoid formula with Compound 12, 27, 62, 74, or 76 at 7 days post-warming was at least about 3 to 4-fold greater compared to the formula containing DMSO.

V. Exemplary Embodiments

Exemplary embodiments provided in accordance with the presently disclosed subject matter include, but are not limited to, the claims and the following embodiments:

1. A method for cryopreserving a population of cells with improved cell viability, the method comprising:
 (a) contacting a population of cells with a peptoid polymer or a salt thereof comprising one or more polar peptoid monomers; and
 (b) cooling the population of cells to a temperature of from 0° C. to about −20° C. for a time period of at least about 3 hours to produce a population of supercooled cells,
 wherein at least about 50% of the population of supercooled cells survive after warming to above 0° C.

2. The method of embodiment 1, wherein the temperature is from about −10° C. to about −20° C.

3. The method of embodiment 1 or 2, wherein the temperature is about −20° C.

4. The method of any one of embodiments 1 to 3, wherein the time period is at least about 8 or 16 hours.

5. The method of any one of embodiments 1 to 3, wherein the time period is from about 2 to about 5 days.

6. The method of embodiment 5, wherein the time period is about 2, 3, 4, or 5 days.

7. The method of any one of embodiments 1 to 3, wherein the time period is at least about 5 days.

8. The method of any one of embodiments 1 to 7, wherein at least about 50% of the population of supercooled cells survive after warming to 37° C.

9. The method of any one of embodiments 1 to 8, wherein at least about 60% of the population of supercooled cells survive after warming.

10. The method of any one of embodiments 1 to 8, wherein at least about 70% of the population of supercooled cells survive after warming.

11. The method of any one of embodiments 1 to 8, wherein at least about 80% of the population of supercooled cells survive after warming.

12. The method of any one of embodiments 1 to 8, wherein at least about 90% of the population of supercooled cells survive after warming.

13. The method of any one of embodiments 1 to 12, wherein the improved cell viability comprises enhanced proliferation of the population of supercooled cells that survive after warming compared to a control population of supercooled cells.

14. The method of embodiment 13, wherein the control population of supercooled cells has not been contacted with the peptoid polymer.

15. The method of embodiment 13 or 14, wherein the number of cells in the population of supercooled cells at about 3 days after warming is at least about 1-fold greater than the number of cells in the control population of supercooled cells.

16. The method of embodiment 13 or 14, wherein the number of cells in the population of supercooled cells at about 6 days after warming is at least about 2-fold greater than the number of cells in the control population of supercooled cells.

17. The method of any one of embodiments 1 to 16, wherein the peptoid polymer is present in an amount sufficient to reduce or inhibit ice crystal formation at the temperature.

18. The method of embodiment 17, wherein the peptoid polymer is present in amount between about 100 nM and about 1000 mM.

19. The method of any one of embodiments 1 to 18, wherein the population of cells comprises a tissue or an organ.

20. The method of any one of embodiments 1 to 19, wherein the population of cells is selected from the group consisting of primary cells, heart cells, liver cells, lung cells, kidney cells, pancreatic cells, gastric cells, intestinal cells, muscle cells, skin cells, neural cells, blood cells, immune cells, fibroblasts, genitourinary cells, bone cells, stem cells, sperm cells, oocytes, embryonic cells, epithelial cells, endothelial cells, and a combination thereof.

21. The method of any one of embodiments 1 to 20, wherein the method further comprises:
  (c) warming the population of supercooled cells to above 0° C.

22. The method of any one of embodiments 1 to 21, wherein the peptoid polymer comprises at least 2, 3, 4, 5, 6, 7, 8, 9, 10, 15, 20, 25, or more polar peptoid monomers.

23. The method of any one of embodiments 1 to 22, wherein the polar peptoid monomers have independently selected side chains comprising a hydroxyl group.

24. The method of embodiment 23, wherein the independently selected side chains are optionally substituted $C_{1-18}$ hydroxyalkyl groups.

25. The method of embodiment 24, wherein the $C_{1-18}$ hydroxyalkyl groups are independently selected optionally substituted $C_{1-6}$ hydroxyalkyl groups.

26. The method of any one of embodiments 1 to 25, wherein the peptoid polymer is a peptoid-peptide hybrid or a salt thereof comprising the peptoid polymer and one or more amino acids, wherein the one or more amino acids are located at one or both ends of the peptoid polymer and/or between one or more peptoid monomers.

27. The method of any one of embodiments 1 to 26, wherein the peptoid polymer has a structure according to formula (I):

$$\text{X} \overset{R^1}{\underset{R^2}{\left[ \begin{array}{c} \\ N \\ \end{array} \right]_n}} \overset{O}{Y} \quad (I)$$

a tautomer thereof or stereoisomer thereof,
wherein:
each $R^1$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted alkoxy, optionally substituted $C_{1-18}$ alkylamino, optionally substituted $C_{1-18}$ alkylthio, optionally substituted carboxyalkyl, $C_{3-10}$ cycloalkyl, heterocycloalkyl, aryl, heteroaryl, ($C_{3-10}$ cycloalkyl)alkyl, (heterocycloalkyl)alkyl, arylalkyl, and heteroarylalkyl,
wherein at least one instance of $R^1$ is an optionally substituted $C_{1-18}$ hydroxyalkyl group, and
wherein any of the cycloalkyl, heterocycloalkyl, aryl, and heteroaryl groups is optionally and independently substituted with one or more $R^3$ groups;
each $R^2$ is independently selected from the group consisting of H, optionally substituted $C_{1-18}$ alkyl, optionally substituted $C_{2-18}$ alkenyl, optionally substituted $C_{2-18}$ alkynyl, optionally substituted $C_{1-18}$ hydroxyalkyl, optionally substituted $C_{1-18}$ alkylamino, optionally substituted $C_{1-18}$ alkylthio, and optionally substituted carboxyalkyl;
each $R^3$ is independently selected from the group consisting of halogen, oxo, thioxo, —OH, —SH, amino, $C_{1-8}$ alkyl, $C_{1-8}$ hydroxyalkyl, $C_{1-8}$ alkylamino, and $C_{1-8}$ alkylthio;
X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, acetyl, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond; and the subscript n, representing the number of monomers in the polymer, is between 2 and 50.

28. The method of embodiment 27, wherein at least 2, 3, 4, 5, 6, 7, 8, 9, 10, 15, 20, 25, or more instances of $R^1$ are independently selected optionally substituted $C_{1-18}$ hydroxyalkyl groups.

29. The method of embodiment 28, wherein the $C_{1-18}$ hydroxyalkyl groups are independently selected optionally substituted $C_{1-6}$ hydroxyalkyl groups.

30. The method of embodiment 27, wherein each $R^1$ is independently selected from the group consisting of

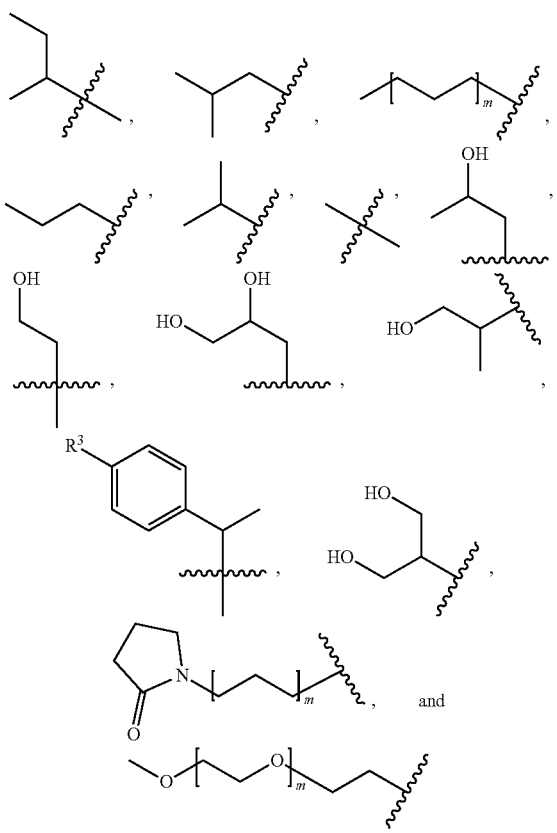

wherein:

m is between 1 and 8; and $R^3$ is selected from the group consisting of H, $C_{1-8}$ alkyl, halogen, hydroxyl, thiol, nitro, amine, oxo, and thioxo.

31. The method of embodiment 30, wherein one or more $R^1$ has a structure according to Rib:

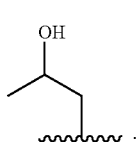

32. The method of embodiment 27, wherein each $R^1$ is independently selected from the group consisting of

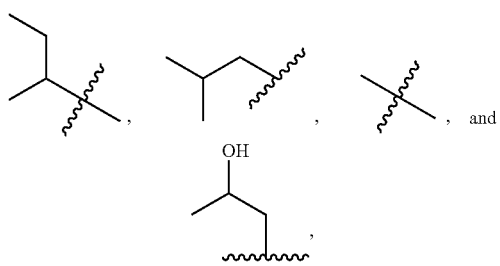

33. The method of any one of embodiments 27 to 32, wherein each instance of $R^2$ is H.

34. The method of any one of embodiments 27 to 33, wherein n is between 6 and 25.

35. The method of any one of embodiments 27 to 33, wherein n is between 6 and 20.

36. The method of any one of embodiments 27 to 33, wherein n is between 10 and 25.

37. The method of any one of embodiments 27 to 36, wherein X is selected from the group consisting of H, $C_{1-8}$ alkyl, and $C_{1-8}$ acyl; and Y is selected from the group consisting of —OH and amino.

38. The method of any one of embodiments 1 to 26, wherein the peptoid polymer comprises subunits comprising one or more first hydrophobic peptoid monomers H and one or more first polar peptoid monomers P arranged such that the peptoid polymer has the sequence $[H_aP_b]_n$ or $[P_bH_a]_n$, wherein:

the subscript a, representing the number of consecutive first hydrophobic peptoid monomers within a subunit, is between 1 and 10;

the subscript b, representing the number of consecutive first polar peptoid monomers within a subunit, is between 1 and 10; and the subscript n, representing the number of subunits within the peptoid polymer, is between 2 and 50.

39. The method of embodiment 38, further comprising substituents X and Y such that the peptoid polymer has the sequence X—$[H_aP_b]_n$—Y or X—$[P_bH_a]_n$—Y, wherein:

X and Y are independently selected from the group consisting of H, optionally substituted $C_{1-8}$ alkyl, optionally substituted $C_{1-8}$ acyl, optionally substituted $C_{1-8}$ alkylamino, —OH, —SH, —NH$_2$, carboxy, optionally substituted $C_{1-8}$ hydroxyalkyl, optionally substituted $C_{1-8}$ alkylamino, optionally substituted $C_{2-8}$ alkylthio, optionally substituted $C_{1-8}$ carboxyalkyl, and halogen, or alternatively X and Y are taken together to form a covalent bond.

40. The method of embodiment 38 or 39, wherein the subunits further comprise a second hydrophobic peptoid monomer and/or a second polar peptoid monomer such that the peptoid polymer has the sequence $[H_aP_bH_cP_d]_n$ or $[P_bH_aP_dH_c]_n$, wherein:

the subscript c, representing the number of consecutive second hydrophobic peptoid monomers within a subunit, is between 0 and 10;

the subscript d, representing the number of consecutive second polar peptoid monomers within a subunit, is between 0 and 10; and both c and d are not 0.

41. The method of embodiment 40, further comprising substituents X and Y such that the peptoid polymer has the sequence X—[H$_a$P$_b$H$_c$P$_d$]$_n$—Y or X—[P$_b$H$_a$P$_d$H$_c$]$_n$—Y, wherein:

X and Y are independently selected from the group consisting of H, optionally substituted C$_{1-8}$ alkyl, optionally substituted C$_{1-8}$ acyl, optionally substituted C$_{1-8}$ alkylamino, —OH, —SH, —NH$_2$, carboxy, optionally substituted C$_{1-8}$ hydroxyalkyl, optionally substituted C$_{1-8}$ alkylamino, optionally substituted C$_{2-8}$ alkylthio, optionally substituted C$_{1-8}$ carboxyalkyl, and halogen, or alternatively X and Y are taken together to form a covalent bond.

42. The method of any one of embodiments 38 to 41, further comprising a sequence Z that comprises one or more hydrophobic peptoid monomers and/or one or more polar peptoid monomers, wherein Z is located before the first subunit, after the last subunit, and/or between one or more subunits.

43. The method of any one of embodiments 1 to 26, wherein the peptoid polymer comprises:
   (a) subunits comprising two first hydrophobic peptoid monomers H and two first polar peptoid monomers P, and
   (b) two second hydrophobic peptoid monomers located at the C-terminal end of the peptoid polymer,
   arranged such that the peptoid polymer has the sequence [H$_2$P$_2$]$_n$H$_2$ or [P$_2$H$_2$]$_n$H$_2$, wherein the subscript n, representing the number of subunits within the peptoid polymer, is between 1 and 50.

44. The method of embodiment 43, wherein the peptoid polymer further comprises substituents X and Y such that the peptoid polymer has the sequence X—[H$_2$P$_2$]$_n$H$_2$—Y or X—[P$_2$H$_2$]$_n$H$_2$—Y, wherein:

X and Y are independently selected from the group consisting of H, optionally substituted C$_{1-8}$ alkyl, optionally substituted C$_{1-8}$ acyl, optionally substituted C$_{1-8}$ alkylamino, —OH, —SH, —NH$_2$, carboxy, optionally substituted C$_{1-8}$ hydroxyalkyl, optionally substituted C$_{1-8}$ alkylamino, optionally substituted C$_{2-8}$ alkylthio, optionally substituted C$_{1-8}$ carboxyalkyl, and halogen, or alternatively X and Y are taken together to form a covalent bond.

45. The method of embodiment 43 or 44, wherein n is between 1 and 10.

46. The method of any one of embodiments 38 to 45, wherein the first and/or second hydrophobic peptoid monomers are independently selected from the group consisting of

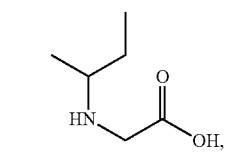
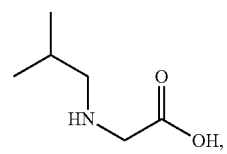

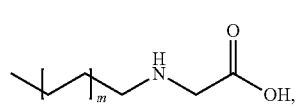

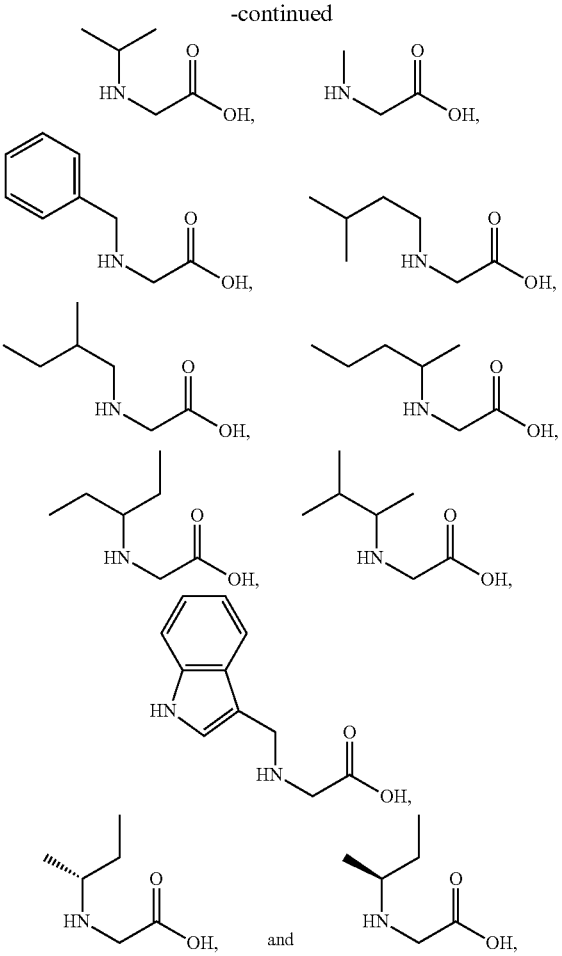

wherein the subscript m is the number of repeat units and is between 1 and 10.

47. The method of any one of embodiments 38 to 46, wherein the peptoid polymer comprises a polar peptoid monomer having a side chain that comprises a hydroxyl group.

48. The method of any one of embodiments 38 to 47, wherein the first and/or second polar peptoid monomers are independently selected from the group consisting of

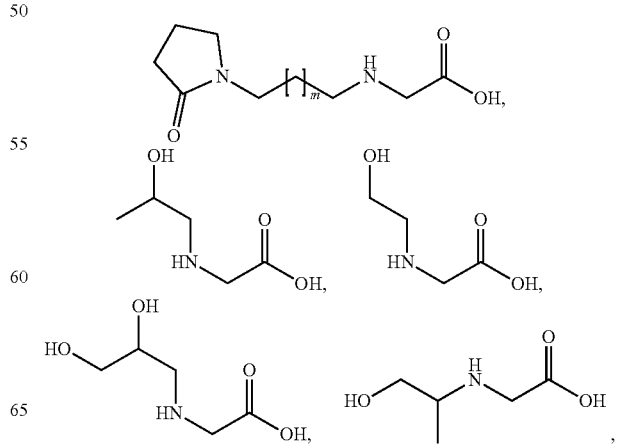

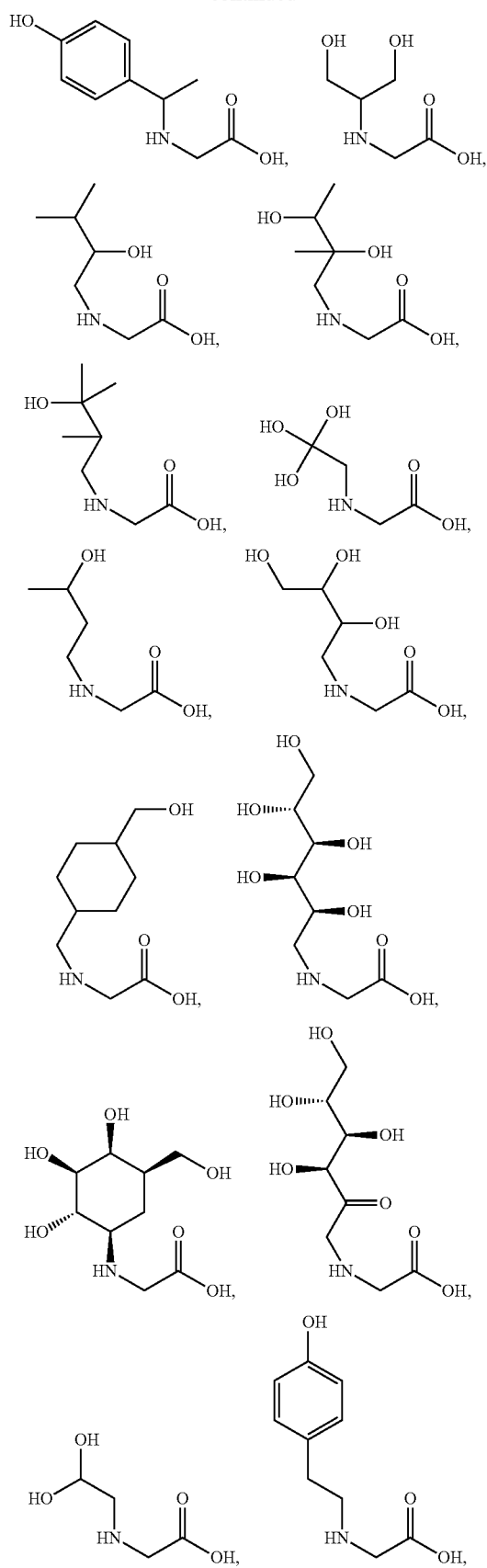
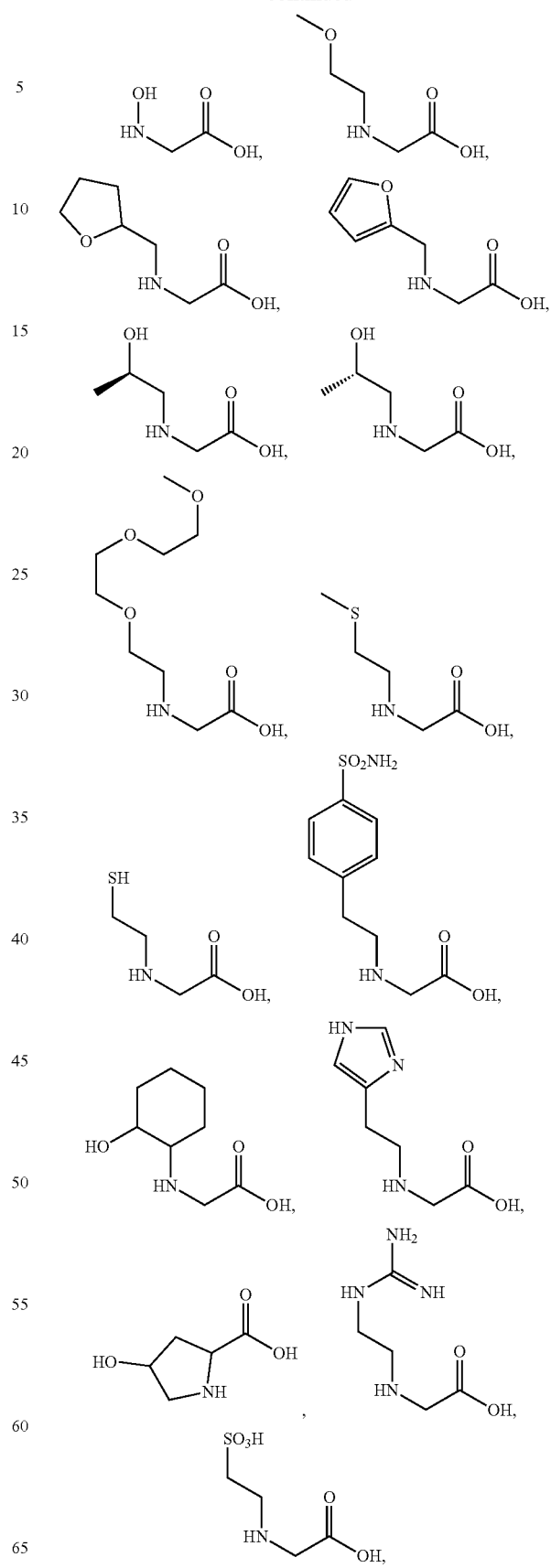

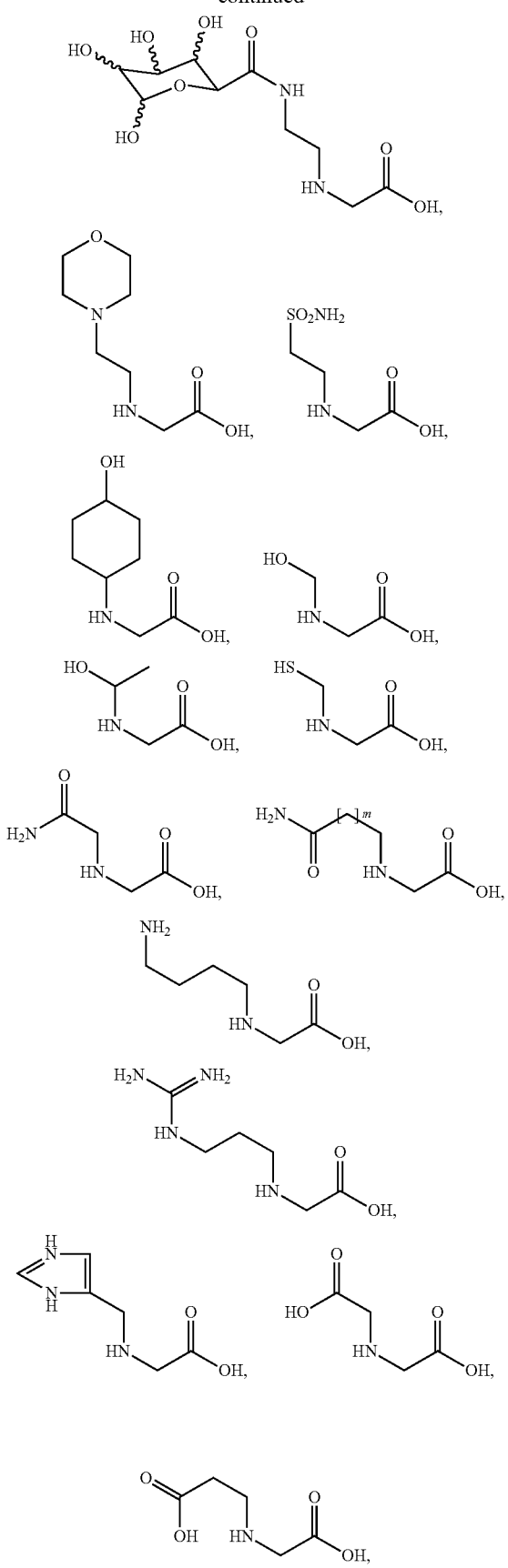
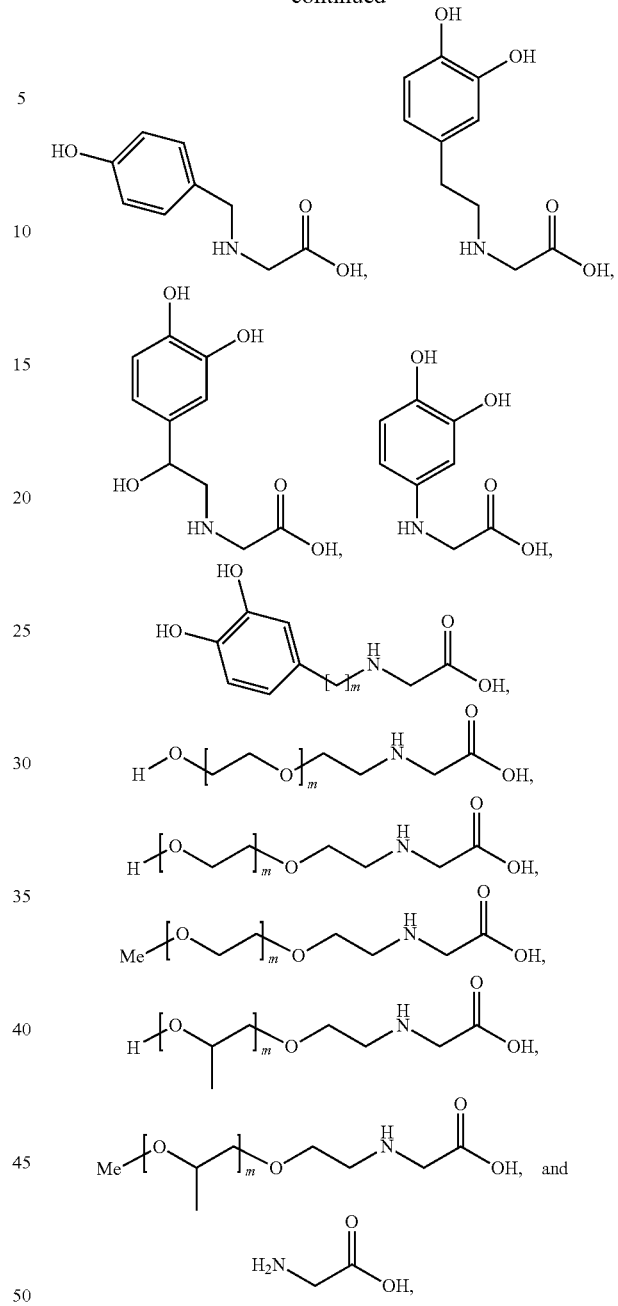

wherein the subscript m is the number of repeat units and is between 1 and 10.

49. The method of any one of embodiments 38 to 48, wherein each of the first and/or second polar peptoid monomers comprise a side chain that is independently selected from the group consisting of ($C_{1-6}$ alkoxy)($C_{1-6}$ alkylene), oligo(ethylene glycol), (4- to 10-membered heterocycloalkyl)($C_{1-6}$ alkylene), and (5- to 10-membered heteroaryl) ($C_{1-6}$ alkylene).

50. The method of embodiment 49, wherein (4- to 10-membered heterocycloalkyl)($C_{1-6}$ alkylene) comprises a 4-6 membered heterocyclic ring, wherein at least one member is selected from the group consisting of O and N.

51. The method of embodiment 49 or 50, wherein (4- to 10-membered heterocycloalkyl)($C_{1-6}$ alkylene) comprises a tetrahydrofuranyl or oxopyrrolidinyl moiety.

52. The method of embodiment 51, wherein the peptoid polymer comprises

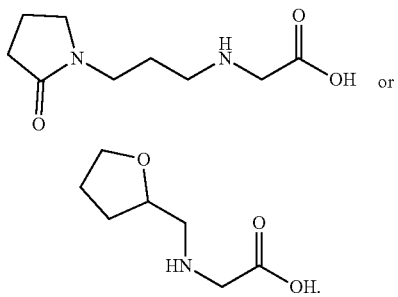 or

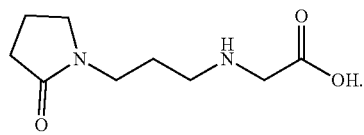 [SMILES: O=C(O)CNCCCN1CCCC1=O]

53. The method of embodiment 52, wherein all of the polar peptoid monomers are

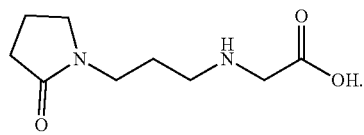 [SMILES: O=C(O)CNCCCN1CCCC1=O]

54. The method of embodiment 49, wherein (5- to 10-membered heteroaryl)($C_{1-6}$ alkylene) comprises a 5-6 membered aromatic ring, wherein at least one ring member is selected from the group consisting of O and N.

55. The method of embodiment 49 or 54, wherein (5- to 10-membered heteroaryl)($C_{1-6}$ alkylene) comprises a furanyl moiety.

56. The method of embodiment 55, wherein the peptoid polymer comprises

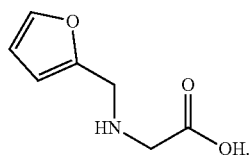 [SMILES: O=C(O)CNCc1ccco1]

57. The method of embodiment 49, wherein the side chain comprises a methoxyethyl group.

58. The method of embodiment 57, wherein the peptoid polymer comprises

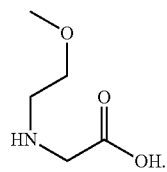

59. The method of embodiment 49, wherein the side chain comprises an oligo(ethylene glycol) moiety.

60. The method of embodiment 59, wherein the oligo (ethylene glycol) moiety is a 2-(2-(2-methoxyethoxy) ethoxy)ethyl moiety.

61. The method of embodiment 60, wherein the peptoid polymer comprises

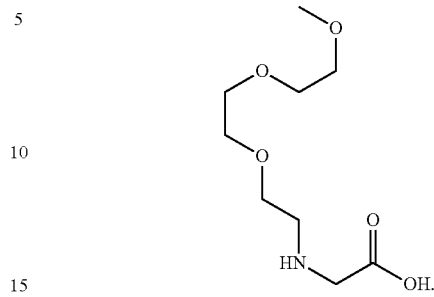

62. The method of any one of embodiments 38 to 42 or 46 to 61, wherein n is between 2 and 10.

63. The method of any one of embodiments 38 to 42 or 46 to 62, where a is between 1 and 5.

64. The method of any one of embodiments 38 to 42 or 46 to 63, wherein b is between 1 and 5.

65. The method of embodiment 63 or 64, wherein a is between 1 and 3 and b is between 1 and 3.

66. The method of any one of embodiments 40 to 42 or 46 to 65, wherein c is between 0 and 5.

67. The method of any one of embodiments 40 to 42 or 46 to 66, wherein d is between 0 and 5.

68. The method of any one of embodiments 38 to 67, wherein about 10, 20, 30, 40, 50, 60, 70, 80, or 90 percent of the peptoid monomers are hydrophobic.

69. The method of any one of embodiments 1 to 68, wherein the peptoid polymer salt is selected from the group consisting of a hydrochloride salt, acetate salt, sulfate salt, phosphate salt, maleate salt, citrate salt, mesylate salt, nitrate salt, tartrate salt, gluconate salt, and a combination thereof.

70. The method of any one of embodiments 1 to 69, wherein the peptoid polymer is formulated in a cryoprotectant solution.

71. The method of embodiment 70, wherein the cryoprotectant solution further comprises a compound selected from the group consisting of an ionic species, a penetrating cryoprotectant, a non-penetrating cryoprotectant, an antioxidant, a cell membrane stabilizing compound, an aquaporin or other channel forming compound, an alcohol, a sugar, a sugar derivative, a nonionic surfactant, a protein, dimethyl sulfoxide (DMSO), polyethylene glycol (PEG), polypropylene glycol (PPG), Ficoll®, polyvinylpyrrolidone, polyvinyl alcohol, hyaluronan, formamide, a natural or synthetic hydrogel, and a combination thereof.

72. A population of supercooled cells with improved cell viability produced by the method of any one of embodiments 1 to 71.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. All publications, patents, and patent applications cited in this specification are herein incorporated by reference as if each individual publication, patent, or patent application were specifically and individually indicated to be incorporated by reference.

VI. Informal Sequence Listing

| Sequence | Notes |
|---|---|
| Nsb-Nsb-Nhp-Nsb-Nsb-Nhp-Nsb-Nsb-Nhp-Nsb | Compound 1 |
| Nhp-Nhp-Nhp-Nhp-Nhp-Nhp-Nhp-Nhp-Nhp-Nhp | Compound 10 |
| Nep-Nep-Xaa-Xaa-Xaa-Nep-Nep-Nep-Nep-Nme-Nme | Peptoid-Peptide Hybrid |
| Nme-Nme-Xaa-Nme-Nme-Nme-Nme-Nhp-Nhp-Nsb-Xaa-Nme-Nme-Xaa-Nme-Nme-Nme | Peptoid-Peptide Hybrid |
| Nme-Nme-Xaa-Nme-Nme-Nme-Nme-Nme-Nme-Xaa-Xaa | Peptoid-Peptide Hybrid |
| Arg-Nsb-Nsb-Nhp-Nhp-Nsb-Nsb-Nhp-Nhp-Nsb-Nsb | Peptoid-Peptide Hybrid (Compound 58) |
| Nsb-Nhp-Nhp-Nhp-Nsb-Nhp-Nhp-Nhp-Nsb-Nhp | Compound 6 |
| Nsb-Nsb-Nhp-Nhp-Nsb-Nsb-Nhp-Nhp-Nsb-Nsb | Compound 12 |
| Nsb-Nhp-Nhp-Nhp-Nhp-Nhp-Nsb-Nhp-Nhp-Nhp | Compound 8 |
| Nsb-Nsb-Nsb-Nhp-Nhp-Nhp-Nsb-Nsb-Nsb-Nhp | Compound 2 |
| Nib-Nib-Nhp-Nhp-Nib-Nib-Nhp-Nhp-Nib-Nib | Compound 25 |
| Nbu-Nbu-Nhp-Nhp-Nbu-Nbu-Nhp-Nhp-Nbu-Nbu | Compound 26 |
| Npr-Npr-Nhp-Nhp-Npr-Npr-Nhp-Nhp-Npr-Npr | Compound 27 |
| Nip-Nip-Nhp-Nhp-Nip-Nip-Nhp-Nhp-Nip-Nip | Compound 28 |
| Nmb-Nmb-Nhp-Nhp-Nmb-Nmb-Nhp-Nhp-Nmb-Nmb | Compound 59 |
| Ac-Nsb-Nsb-Nhp-Nhp-Nsb-Nsb-Nhp-Nhp-Nsb-Nsb | Compound 60 (Compound 12 with acetylated N-terminus) |
| Nsb-Nsb-Nhp-Nhp-Nsb-Nsb-Nhp-Nhp-Nsb-Nsb-COOH | Compound 61 (Compound 12 with carboxy C-terminus) |
| Nsb-Nsb-Nmo-Nmo-Nsb-Nsb-Nmo-Nmo-Nsb-Nsb | Compound 62 |
| Nsb-Nsb-Ntf-Ntf-Nsb-Nsb-Ntf-Ntf-Nsb-Nsb | Compound 63 |
| Nme-Nme-Nhp-Nhp-Nme-Nme-Nhp-Nhp-Nme-Nme | Compound 64 |
| Nbr-Nbr-Nhe-Nhe-Nbr-Nbr-Nhe-Nhe-Nbr-Nbr | Compound 65 |
| Npr-Npr-Nrh-Nrh-Npr-Npr-Nrh-Nrh-Npr-Npr | Compound 66 |
| Nsb-Nsb-N3p-N3p-Nsb-Nsb-N3p-N3p-Nsb-Nsb | Compound 67 |
| Nsb-Nsb-Ndh-Ndh-Nsb-Nsb-Ndh-Ndh-Nsb-Nsb | Compound 68 |
| Nsb-Nsb-Nhp-Nhp-Nsb-Nsb-Nhp-Nsb-Nsb-Nsb | Compound 69 |
| Nsb-Nsb-Nhp-Nhp-Nsb-Nsb-Nsb-Nhp-Nsb-Nsb | Compound 70 |
| Nsb-Nsb-Nhp-Nsb-Nsb-Nsb-Nhp-Nhp-Nsb-Nsb | Compound 71 |
| Nsb-Nsb-Nsb-Nhp-Nsb-Nsb-Nhp-Nhp-Nsb-Nsb | Compound 72 |
| Nsb-Nsb-Nff-Nff-Nsb-Nsb-Nff-Nff-Nsb-Nsb | Compound 73 |
| Nsb-Nsb-Nhe-Nhe-Nsb-Nsb-Nhe-Nhe-Nsb-Nsb | Compound 74 |
| Nsb-Nsb-Nyp-Nyp-Nsb-Nsb-Nyp-Nyp-Nsb-Nsb | Compound 75 |
| Nsb-Nsb-Nop-Nop-Nsb-Nsb-Nop-Nop-Nsb-Nsb | Compound 76 |
| Nbr-Nbr-Nrh-Nrh-Nbr-Nbr-Nrh-Nrh-Nbr-Nbr | Compound 77 |
| Nbr-Nbr-Nsh-Nsh-Nbr-Nbr-Nsh-Nsh-Nbr-Nbr | Compound 78 |
| Nsb-Nsb-Ndp-Ndp-Nsb-Nsb-Ndp-Ndp-Nsb-Nsb | Compound 79 |

| VI. Informal Sequence Listing | |
|---|---|
| Sequence | Notes |
| Nrh-Nrh-Nrh-Nrh-Nrh-Nrh-Nrh-Nrh-Nrh-Nrh | Compound 80 |
| Nsb-Nsb-Nhp-Nhp-Nsb-Nsb | Compound 81 |
| Nhp-Nhp-Nsb-Nsb-Nhp-Nhp-Nsb | Compound 82 |
| Nsb-Nsb-Nhp-Nhp-Nsb-Nsb-Nhp-Nhp-Nsb-Nsb-Nhp-Nhp-Nsb-Nsb | Compound 83 |
| Nsb-Nsb-Nhp-Nhp-Nsb-Nsb-Nhp-Nhp-Nsb-Nsb-Nhp-Nhp-Nsb-Nsb-Nhp-Nhp-Nsb-Nsb | Compound 84 |
| Nsb-Nsb-Nhp-Nhp-Nsb-Nsb-Nhp-Nhp-Nsb-Nsb-Nhp-Nhp-Nsb-Nsb-Nhp-Nhp-Nsb-Nsb-Nhp-Nhp-Nsb-Nsb | Compound 85 |
| Nbr-Nbr-Nop-Nop-Nbr-Nbr-Nop-Nop-Nbr-Nbr | Compound 86 |
| Nbs-Nbs-Nop-Nop-Nbs-Nbs-Nop-Nop-Nbs-Nbs | Compound 87 |
| Nbs-Nbs-Nrh-Nrh-Nbs-Nbs-Nrh-Nrh-Nbs-Nbs | Compound 88 |
| Nbs-Nbs-Nsh-Nsh-Nbs-Nbs-Nsh-Nsh-Nbs-Nbs | Compound 89 |
| Nbr-Nbs-Nrh-Nrh-Nbr-Nbs-Nrh-Nrh-Nbr-Nbs | Compound 90 |
| Nbs-Nbr-Nrh-Nrh-Nbs-Nbr-Nrh-Nrh-Nbs-Nbr | Compound 91 |
| Nbr-Nbs-Nsh-Nsh-Nbr-Nbs-Nsh-Nsh-Nbr-Nbs | Compound 92 |
| Nbs-Nbr-Nsh-Nsh-Nbs-Nbr-Nsh-Nsh-Nbs-Nbr | Compound 93 |
| Nbr-Nbr-Nrh-Nsh-Nbr-Nbr-Nrh-Nsh-Nbr-Nbr | Compound 94 |
| Nbr-Nbr-Nsh-Nrh-Nbr-Nbr-Nsh-Nrh-Nbr-Nbr | Compound 95 |
| Nbs-Nbs-Nrh-Nsh-Nbs-Nbs-Nrh-Nsh-Nbs-Nbs | Compound 96 |
| Nbs-Nbs-Nsh-Nrh-Nbs-Nbs-Nsh-Nrh-Nbs-Nbs | Compound 97 |
| Nbr-Nbs-Nrh-Nsh-Nbr-Nbs-Nrh-Nsh-Nbr-Nbs | Compound 98 |
| Nbr-Nbs-Nsh-Nrh-Nbr-Nbs-Nsh-Nrh-Nbr-Nbs | Compound 99 |
| Nbs-Nbr-Nrh-Nsh-Nbs-Nbr-Nrh-Nsh-Nbs-Nbr | Compound 100 |
| Nbs-Nbr-Nsh-Nrh-Nbs-Nbr-Nsh-Nrh-Nbs-Nbr | Compound 101 |

What is claimed is:

1. A method for preserving a biological sample or biological macromolecule, the method comprising:
   (a) contacting a biological sample or biological macromolecule with a solution comprising a peptoid polymer or a salt thereof comprising one or more polar peptoid monomers; and
   (b) cooling the solution to a temperature of from 0° C. to about −20° C. for a time period of at least about 3 hours to produce a preserved biological sample or preserved biological macromolecule,
   wherein the peptoid polymer is present in an amount sufficient to reduce or inhibit ice crystal formation at the temperature, and
   wherein the solution comprising the preserved biological sample or preserved biological macromolecule is unfrozen at the temperature.

2. The method of claim 1, wherein the biological sample comprises a tissue, organ, or cells.

3. The method of claim 2, wherein the tissue is a bioengineered tissue.

4. The method of claim 2, wherein the tissue or organ is selected from the group consisting of heart, liver, lung, kidney, pancreas, intestine, thymus, cornea, bone marrow, organoids, and a combination thereof.

5. The method of claim 2, wherein the cells are selected from the group consisting of primary cells, heart cells, liver cells, lung cells, kidney cells, pancreatic cells, gastric cells, intestinal cells, muscle cells, skin cells, neural cells, blood cells, immune cells, fibroblasts, genitourinary cells, bone cells, stem cells, sperm cells, oocytes, embryonic cells, epithelial cells, endothelial cells, and a combination thereof.

6. The method of claim 1, wherein the biological macromolecule is selected from the group consisting of a nucleic acid, an amino acid, a protein, an isolated protein, a peptide, a lipid, a composite structure, and a combination thereof.

7. The method of claim 6, wherein the biological macromolecule is a nucleic acid.

8. The method of claim 7, wherein the nucleic acid is DNA or RNA.

9. The method of claim 1, wherein the preserved biological sample or preserved biological macromolecule is in a liquid, ice-free suspension at the temperature.

10. The method of claim 1, wherein the temperature is from about −5° C. to about −20° C.

11. The method of claim 1, wherein the time period is at least about 8 or 16 hours.

12. The method of claim 1, wherein the time period is from about 2 to about 5 days.

13. The method of claim 1, wherein the time period is at least about 72 hours.

14. The method of claim 1, wherein the peptoid polymer comprises at least 2, 3, 4, 5, 6, 7, 8, 9, 10, 15, 20, 25, or more polar peptoid monomers.

15. The method of claim 1, wherein the one or more polar peptoid monomers have independently selected side chains comprising a hydroxyl group.

16. The method of claim 15, wherein the independently selected side chains are optionally substituted $C_{1-18}$ hydroxyalkyl groups.

17. The method of claim 16, wherein the $C_{1-18}$ hydroxyalkyl groups are independently selected optionally substituted $C_{1-6}$ hydroxyalkyl groups.

18. The method of claim 1, wherein at least 2 of the polar peptoid monomers have a side chain that comprises an independently selected optionally substituted $C_{1-18}$ hydroxyalkyl group.

19. The method of claim 18, wherein the $C_{1-18}$ hydroxyalkyl group is an independently selected optionally substituted $C_{1-6}$ hydroxyalkyl group.

20. The method of claim 1, wherein the peptoid polymer is a peptoid-peptide hybrid or a salt thereof comprising the peptoid polymer and one or more amino acids, wherein the one or more amino acids are located at one or both ends of the peptoid polymer and/or between one or more peptoid monomers.

21. The method of claim 1, wherein the peptoid polymer salt is selected from the group consisting of a hydrochloride salt, acetate salt, sulfate salt, phosphate salt, maleate salt, citrate salt, mesylate salt, nitrate salt, tartrate salt, gluconate salt, and a combination thereof.

* * * * *